US009822381B2

(12) United States Patent
Jantz et al.

(10) Patent No.: US 9,822,381 B2
(45) Date of Patent: Nov. 21, 2017

(54) METHODS AND PRODUCTS FOR PRODUCING ENGINEERED MAMMALIAN CELL LINES WITH AMPLIFIED TRANSGENES

(71) Applicant: Precision Biosciences, Inc., Research Triangle Park, NC (US)

(72) Inventors: Derek Jantz, Durham, NC (US); James Jefferson Smith, Durham, NC (US); Michael G. Nicholson, Chapel Hill, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 14/806,175

(22) Filed: Jul. 22, 2015

(65) Prior Publication Data

US 2016/0017372 A1 Jan. 21, 2016

Related U.S. Application Data

(63) Continuation of application No. 14/091,572, filed on Nov. 27, 2013, now abandoned, which is a continuation of application No. PCT/US2012/040599, filed on Jun. 1, 2012.

(60) Provisional application No. 61/492,174, filed on Jun. 1, 2011.

(51) Int. Cl.
| | |
|---|---|
| *C12N 15/90* | (2006.01) |
| *C12N 9/22* | (2006.01) |
| *C12N 9/06* | (2006.01) |
| *C12N 9/00* | (2006.01) |
| *C12N 15/87* | (2006.01) |
| *C12N 9/16* | (2006.01) |

(52) U.S. Cl.
CPC ........... *C12N 15/907* (2013.01); *C12N 9/003* (2013.01); *C12N 9/22* (2013.01); *C12N 9/93* (2013.01); *C12Y 105/01003* (2013.01); *C12Y 603/01002* (2013.01); *C12Y 301/04* (2013.01)

(58) Field of Classification Search
None
See application file for complete search history.

(56) References Cited

U.S. PATENT DOCUMENTS

| | | | |
|---|---|---|---|
| 5,384,253 | A | 1/1995 | Krzyzek et al. |
| 7,037,492 | B2 | 5/2006 | Glorioso et al. |
| 2003/0224481 | A1 | 12/2003 | Elledge et al. |
| 2006/0206949 | A1 | 9/2006 | Arnould et al. |

FOREIGN PATENT DOCUMENTS

| | | |
|---|---|---|
| CA | 2671825 A1 | 8/2008 |
| WO | WO-2007047859 A2 | 4/2007 |
| WO | WO-2007049156 A2 | 5/2007 |
| WO | WO-2007137267 A2 | 11/2007 |
| WO | WO-2008059317 A1 | 5/2008 |
| WO | WO-2008096070 A2 | 8/2008 |
| WO | WO-2009059195 A2 | 5/2009 |
| WO | WO-2009076292 A2 | 6/2009 |
| WO | WO-2009095742 A1 | 8/2009 |
| WO | WO-2009114321 A2 | 9/2009 |

OTHER PUBLICATIONS

Anachkova et al., "Replication in the Amplified Dihydrofolate Reductase Domain in CHO Cells May Initiate at Two Distinct Sites, One of Which is a Repetitive Sequence Element," Molecular and Cellular Biology, vol. 9, No. Feb. 2, 1989 (pp. 532-540).
Andersen et al., "Recombinant Protein Expression for Therapeutic Applications," Current Opinion in Biotechnology, vol. 13, No. 2, Apr. 2002 (pp. 117-123).
Arnould et al., "Engineering of Large Numbers of Highly Specific Homing Endonucleases that Induce Recombination on Novel DNA Targets," Journal of Molecular Biology, Oct. 24, 2005 (16 pages).
Cabaniols et al., "Meganuclease-Driven Targeted Integration in CHO-K1 Cells for the Fast Generation of HTS-Compatible Cell-Based Assays," Journal of Biomolecular Screening, vol. 15, No. 8, No Month Listed 2010 (pp. 956-967).
Cahill et al., "Mechanisms of Eukaryotic DNA Double Strand Break Repair," Frontiers in Bioscience, vol. 11, May 2006 (pp. 1958-1976).
Chames et al., "In Vivo Selection of Engineered Homing Endonucleases Using Double-Strand Break Induced Homologous Recombination," Nucleic Acids Research, vol. 33, No. 20, Oct. 21, 2005 (10 pages).
Chevalier et al., "Homing Endonucleases: Structural and Functional Insight into the Catalysts of Intron/Intein Mobility," Nucleic Acids Research, vol. 29, No. 18, No Month Listed 2001 (pp. 3757-3774).
Chilton et al., "Targeted Integration of T-DNA into the Tobacco Genome at Double-Strand Breaks: New Insights on the Mechanism of T-DNA Integration," Plant Physiology, vol. 133, Nov. 2003 (pp. 956-965).
Clapp, "Somatic Gene Therapy into Hematopoietic Cells. Current Status and Future Implications," Clinics in Perinatology, vol. 20, No. 1, Mar. 1993 (pp. 155-168).
Curiel et al., "Adenovirus Enhancement of Transferrin-Polylysine-Mediated Gene Delivery," Proceedings of the National Academy of Sciences of the United States of America, vol. 88, No. 19, Oct. 1991 (pp. 8850-8854).
Curiel et al., "High-Efficiency Gene Transfer Mediated by Adenovirus Coupled to DNA-Polylysine Complexes," Human Gene Therapy, vol. 3, No. 2, Apr. 1992 (pp. 147-154).

(Continued)

*Primary Examiner* — Nancy J Leith
(74) *Attorney, Agent, or Firm* — Wolf, Greenfield & Sacks, P.C.

(57) ABSTRACT

Methods of inserting genes into defined locations in the chromosomal DNA of cultured mammalian cell lines which are subject to gene amplification are disclosed. In particular, sequences of interest (e.g., genes encoding biotherapeutic proteins) are inserted proximal to selectable genes in amplifiable loci, and the transformed cells are subjected to selection to induce co-amplification of the selectable gene and the sequence of interest. The invention also relates to meganucleases, vectors and engineered cell lines necessary for performing the methods, to cell lines resulting from the application of the methods, and use of the cell lines to produce protein products of interest.

11 Claims, 11 Drawing Sheets

(56) References Cited

OTHER PUBLICATIONS

Dingermann et al., "Establishment of a System for Conditional Gene Expression Using an Inducible tRNA Suppressor Gene," Molecular and Cellular Biology, vol. 12, No. 9, Sep. 1992 (pp. 4038-4045).
Eglitis et al., "Retroviral Vectors for Introduction of Genes into Mammalian Cells," Biotechniques, vol. 6, No. 7, Jul.-Aug. 1988 (pp. 608-614).
Eglitis et al., "Retroviral-Mediated Gene Transfer into Hemopoietic Cells," Advances in Experimental Medicine and Biology, vol. 241, 1988 (pp. 19-27).
Epinat et al., "A Novel Engineered Meganuclease Induces Homologous Recombination in Yeast and Mammalian Cells," Nucleic Acids Research, vol. 31, No. 11, Jun. 2003 (pp. 2952-2962).
Fromm et al., "Expression of Genes Transferred into Monocot and Dicot Plant Cells by Electroporation," Proceedings of the National Academy of Sciences of the United States of America, vol. 82, No. 17, Sep. 1985 (pp. 5824-5828).
Fynan et al., "DNA Vaccines: Protective Immunizations by Parenteral, Mucosal, and Gene-Gun Inoculations," Proceedings of the National Academy of Sciences of the United States of America, vol. 90, No. 24, Dec. 1993 (pp. 11478-11482).
Gao et al., "Heritable Targeted Mutagenesis in Maize Using a Designed Endonuclease," The Plant Journal, vol. 61, No. 1 Jan. 2010 (pp. 176-187).
Gouble et al., "Efficient in Toto Targeted Recombination in Mouse Liver by Meganuclease-Induced Double-Strand Break," The Journal of Gene Medicine, vol. 8, No. 5, May 2006 (pp. 616-622).
Graham et al., "Transformation of Rat Cells by DNA of Human Adenovirus 5," Virology, vol. 54, No. 2, Aug. 1973 (pp. 536-539).
Hudecz et al., "Medium-Sized Peptides as Built in Carriers for Biologically Active Compounds," Medicinal Research Review, vol. 25, No. 6, Nov. 2005 (pp. 679-736).
International Search Report and Written Opinion issued by the U.S. Patent and Trademark Office as International Searching Authority for International Application No. PCT/US2012/040599 dated Jan. 10, 2013 (13 pages).
Johnston et al., "Gene Gun Transfection of Animal Cells and Genetic Immunization," Methods in Cell Biology, vol. 43, No Month Listed 1994 (pp. 353-365).
Lasic et al., "Liposomes revisited," Science, vol. 267, No. 5202, Mar. 3, 1995 (pp. 1275-1276).
Li et al., "TAL Nucleases (TALNs): Hybrid Proteins Composed of TAL Effectors and FokI DNA-Cleavage Domain," Nucleic Acids Research, vol. 39, No. 1, Jan. 2011 (pp. 359-372).
Looney et al., "Isolation of the Amplified Dihydrofolate Reductase Domain from Methotrexate-Resistant Chinese Hamster Ovary Cells," Molecular and Cellular Biology, vol. 7, No. 2, Feb. 1987 (pp. 569-577).
Lu et al., "High Efficiency Retroviral Mediated Gene Transduction into Single Isolated Immature and Replatable CB343+ Hematopoietic Stem/Progenitor Cells from Human Umbilical Cord Blood," Journal of Experimental Medicine, vol. 178, No. 6 Dec. 1, 1993 (pp. 2089-2096).
Ma et al., "Organization and Genesis of Dihydrofolate Reductase Amplicons in the Genome of a Methotrexate-Resistant Chinese Hamster Ovary Cell Line," Molecular and Cellular Biology, vol. 8, No. 6, Jun. 1988 (pp. 2316-2327).
McDaniel et al., "Advances in Synthetic Biology: On the Path from Prototypes to Applications," Current Opinions in Biotechnology, vol. 16, Jul. 12, 2005 (pp. 476-483).
Milbrandt et al., "Methotrexate-Resistant Chinese Hamster Ovary Cells Have Amplified a 135-Kilobase-Pair Region That Includes the Dihydrofolate Reductase Gene," Proceedings of the National Academy of Sciences of the United States of America, vol. 78, No. 10, Oct. 1981 (pp. 6043-6047).
Monnat et al., "Generation of Highly Site-Specific DNA Double-Strand Breaks in Human Cells by the Homing Endonucleases I-Ppol and I-CreI," Biochemical and Biophysical Research Communications, vol. 255, No. 1, No Month Listed 1999 (pp. 88-93).
Morales et al., "Dihydrofolate Reductase Amplification and Sensitization to Methotrexate of Methotrexate-Resistant Colon Cancer Cells," Molecular Cancer Therapeutics, vol. 8, No. 2, Feb. 2009 (pp. 424-432).
Partial Supplementary European Search Report issued by the European Patent office for European Application No. 12792301.9 dated Apr. 21, 2015 (6 pages).
Porteus et al., "Gene Targeting Using Zinc Finger Nucleases," Nature Biotechnology, vol. 23, No. 8, Aug. 2005 (pp. 967-973).
Porteus, "Mammalian Gene Targeting with Designed Zinc Finger Nucleases," Molecular Therapy, vol. 13, No. 2, Feb. 2006 (pp. 438-446).
Puchta et al., "Two Different but Related Mechanisms are Used in Plants for the Repair of Genomic Double-Strand Breaks by Homologous Recombination," Proceedings of the National Academy of Sciences of the United States of America, vol. 93, May 1996 (pp. 5055-5060).
Reichert, "Monoclonal Antibodies as Innovative Therapeutics," Current Pharmaceutical Biotechnology, vol. 9, No. 6, Dec. 2008 (pp. 423-430).
Rong et al., "Targeted Mutagenesis by Homologous Recombination in D. Melanogaster," Genes & Development, vol. 16, No Month Listed 2002 (pp. 1568-1581).
Rouet et al., "Introduction of Double-Strand Breaks into the Genome of Mouse Cells by Expression of a Rare-Cutting Endonuclease," Molecular and Cellular Biology, vol. 14, No. 12, Dec. 1994 (pp. 8096-8106).
Rui et al., "Transfer of Anti-TFAR19 Monoclonal Antibody into HeLa Cells by in Situ Electroporation Can Inhibit the Apoptosis," Life Sciences, vol. 71, No Month Listed 2002 (pp. 1771-1778).
Salomon et al., "Capture of Genomic and T-DNA Sequences During Double-Strand Break Repair in Somatic Plant Cells," The Embo Journal, vol. 17, No. 20, Oct. 15, 1998 (pp. 6086-6095).
Sasaki et al., "The Chinese Hamster Dihydrofolate Reductase Repulication Origin Decision Point Follows Activation of Transcription and Suppressess Initiation of Replication Within Transcription Units," Molecular and Cellular Biology, vol. 26, No. 3, No Month Listed 2006 (pp. 1051-1062).
Seligman et al., "Mutations Altering the Cleavage Specificity of a Homing Endonuclease," Nucleic Acids Research, vol. 30, No. 17, No Month Listed 2002 (pp. 3870-3879).
Stoddard, "Homing Endonuclease Structure and Function," Quarterly Reviews of Biophysics, vol. 38, No Month Listed 2006 (pp. 49-95).
Sussman et al., "Isolation and Characterization of New Homing Endonuclease Specificities at Individual Target Site Positions," Journal of Molecular Biology, vol. 342, No. 1, Sep. 2004 (pp. 31-41).
Thomsen et al., "Promoter-Regulatory Region of the Major Immediate Early Gene of Human Cytomegalovirus," Proceedings of the National Academy of Sciences of the United States of America, vol. 81, No. 3, Feb. 1984 (pp. 659-663).
Tzfira et al., "Towards Targeted Mutagenesis and Gene Replacement in Plants," Trends in Biotechnology, vol. 23, No. 12, Dec. 2005 (pp. 567-569).
Urnov et al., "Highly Efficient Endogenous Human Gene Correction Using Designed Zinc-Finger Nucleases," Nature, vol. 435, vol. 7042, Jun. 2, 2005 (pp. 646-651).
Wagner et al., "Coupling of Adenovirus to Transferrin-Polylysine/DNA Complexes Greatly Enhances Receptor-Mediated Gene Delivery and Expression of Transfected Genes," Proceedings of the National Academy of Sciences of the United States of America, vol. 89, Jul. 1992 (pp. 6099-6103).
Wong et al., "Electric Field Mediated Gene Transfer," Biochemical and Biophysical Research Communications, vol. 107, No. 2, Jul. 30, 1982 (pp. 584-587).
Wright et al., "High-Frequency Homologous Recombination in Plants Mediated by Zinc-Finger Nucleases," The Plant Journal, vol. 44, No Month Listed 2005 (pp. 693-705).
Xu et al., "The Genomic Sequence of the Chinese Hamster Ovary (CHO)-K1 Cell Line," Nature Biotechnology, vol. 29, No. 8, Jul. 2011 (pp. 735-741).

(56) References Cited

OTHER PUBLICATIONS

Yoshikawa et al., "Amplified Gene Location in Chromosomal DNA Affected Recombinant Protein Production and Stability of Amplified Genes," Biotechnology Progress, vol. 16, No. 5, Sep.-Oct. 2000 (pp. 710-715).
Yoshikawa et al., "Evaluation of Stable and Highly Productive Gene Amplified CHO Cell Line Based on the Location of Amplified Genes," Ctyotechnology, vol. 33, No. 1-3, Jul. 2000 (pp. 37-46).
Zatloukal et al., "Transferrinfection: A Highly Efficient Way to Express Gene Constructs in Eukaryotic Cells," Annals New York Academy of Sciences, vol. 660, Oct. 1992 (pp. 136-153).

SEQUENCE LISTING

```
<160> NUMBER OF SEQ ID NOS: 65

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 50001
<212> TYPE: DNA
<213> ORGANISM: Cricetulus griseus
<220> FEATURE:
<221> NAME/KEY: modified_base
<222> LOCATION: (36646)..(36646)
<223> OTHER INFORMATION: a, c, t, g, unknown or other
<220> FEATURE:
<221> NAME/KEY: modified_base
<222> LOCATION: (38354)..(38354)
<223> OTHER INFORMATION: a, c, t, g, unknown or other

<400> SEQUENCE: 2
taaaactcaa gatgccagct ttgtagctag cttaggaaac aaagtagtaa aaataataa      60 tgggtgggtg aaggtctgaa gcatttacag agttctctca agacaaagca cagaggctgg    120
tggccacata acttggcaac tgatttgggg gaacagaata caagaaagga aatttaaata    180
ctgttttcct caatgttgaa ctatatgggc atagtcacag ctgcctaacc tatagagact    240
ggaagctgga acctcggcta tctaagatag aataatcaag aaatgtcaat tatttgagaa    300
aaacatcagg aataaatagc tgctaagtta caagttggtg cttagacat ttggagagga    360 taggatgggg gctcccagac ctggggctcc ctaataaagc tgtgctggcc tacaagttcc    420
agggatcctc cagtccatgc ctcccactgt tgggactgcg ggcgatggtt tctgacgtgg    480
gtactgaggg cctgaactgt ccacacactt aagccacacg cctttactg agtcatctcc    540 tcatctcaga acattttcct ttaatctttc ttaatgaaaa ggtcgcattt cttccgaggg    600
ctagcctcct gttactctct atacatgtca cataaaacta catgaaaact tgaaggcac     660 tatatgtcca tactcagatg aaaagccatt agctgtggtc atacaaaacc ccacagacca    720
actgttggga aacatcagac ttttttcctg cagcgcctgc cctgatcttc cacagagaat    780
tcagtctcac ttttccagg atgacttctg aactatcacc gtaagatgag aatttgaaac     840
aaagatgtaa gtaatgaact tcatgtgttc tgaacacaca gcttagtgca ttgaaattac    900
gtaacacccg cttccttata agccatttct caaaatgttc ccattacacc tgcatcgggg    960
atgggtccca gaatcttcct tttaaataaa cacccccagag gattctgaag ctagaacacc   1020
aaggactgac agagagaagc atgcctgtgg gcgactccag acacctggga gctgcctgct   1080
ttcttgctac tgatttagaa ggcatttgcc cccgaatggg gctgggggac tgtcactatt   1140
tctcattctc gggactttga aaggaagcaa aacagaaaac catgcaaagt ataagccacc   1200
atggaataat ggcagacgat ccggttgtgc agattagatt ttacatattg ctgattttga   1260
agctaaagac ctttcacttc ttaaatatat aataaaattc atacaagagt attttgtgta   1320
ggtaactcag tcagatacaa ggtaagcaaa gtaaatgata ggtgcccctt aacaaaatgc   1380
```

```
attctcatag ttcatttatc aattatagaa atggtggact ggagggaagg cttgaggtca    1440
ggagaatgtg ctgctcttcc agacagcccg ggttcttttc cccagcaatc tgggactcac    1500
gtctgcctgt agctccaggc ccaggggatc tggcaccttc ttctggcctc tgcaggcacc    1560
catacacaca tggcatacac acacatacac aaattctaaa attaaatagt aggttgtagg    1620
cctacacaaa aacatgcata cattaactaa ataattaata gttaataaat aaaaatcaac    1680
caaacacata cactgattaa gtaacatgac tctgtaaggt caaaggcggc tgaccagctg    1740
tgggaagggt taaataataa caatcacctt tgaaagactg gacctggtga ttaaggatgt    1800
tccagctgtg tcgtggatga gaaatcaaat gcataattga atgagtgcca ggaatagaac    1860
tggagacttt ctggtgagaa tgcttttact ggcagtagag tccctgtcta aacaggagag    1920
agacctgcag tagccctgtg gcggccctgc agtggccctg tgatggctct gcagttgtac    1980
tcttcctgag ataggagaca cactagagag tgtttctaat gagcagctcc tgtactttct    2040
gttcccctgg agaccgcacg tgtttctccg ataatacatt gacatttctg ttaaaccatt    2100
ttcttcttgg aacaaaaatg gagaacaaat cagattggtg tgtggtcttt taaataactt    2160
ggtacttaat aacacaaaac aaaattatca gaggctggat tttaggtgct ctcagcatct    2220
gccacccctg agccatcagt caggtcttgg aggaacaatc tccaaggaga aaacagttct    2280
gtcctcagaa aagctggagg aatatgagat tttctacagc actcatagca aaatcattta    2340
cggaagggat cctgagtaag atggcctctt cttcatcaca tggtcatagt ctgcttcaat    2400
ggggagaata gttcaatcta gcatcgagaa atcgaaggtt ccctttgac tggcaatgcc    2460 ccatagatag atagatatag attatgtata tattgtgtaa aacacacgta tgtatatata    2520
atacacatac atgtatgtgt atacatacat acatacatac atacatacat acatacatac    2580
atacatagat acgtgtgtgt gtgtgtgtgt gtgtgtgtgt gtgtgtgtgt gtgtgtgtgt    2640
ttgagactga gtttctctac tatgtagctc tggctgtcct gaaagttgct aagtagacca    2700
gactggccag accagatcca ccctcctctg cctcctaagt gctgagatta aaggcctgca    2760
cccaccccca cccagcccat cttatatttt gcttcatttc aaagtaagct ctatgcatca    2820
tttattcctg catattatta gccatggttc agtcttgttt gtgttttgga atatttactt    2880
aacaaaactt gaaaaacatt tttcaagatt tgtttgtttt taagatttat ttatttatta    2940
tgtataataa taaatattat tatgaaaaac ggtgttctgc ctgcagggca gaagagggca    3000
ccagattgaa ttacagatgg ttgtgagcca ccatgtggtt gctgggactt gaactcagga    3060
cctctggaag agcagccagt acttttaact gctgagccat ctccccaggc ccaaaataca    3120
catcttaagt gtattgccac aagcatacat cttcatggcc caatcttctg tccatcactt    3180
cagacagctc tccttctttc cctggccagt cacaacaccc tcagctatca ggaaaggccc    3240
tatgggggtt gttttgtttt cccactccag ttcccttgcc tgctctgacc tcatgagtag    3300
actcatacag gatgtgctca cttcacttgg gatgatttct ttttcaccca ttgttgctct    3360
gcccagaatt tgttccttt tattgtctta gtgttaatca actatcaaag ccagcaacaa    3420
aaaatagtag ggaaacttt ttgatagggt aaacctgatt gattgcaggc tttggttgcc    3480
ttgtttggtc tatccccttg agagtccctt acaatgtgag ttagttagtg gctgctaact    3540
agttgaatct caacttcctt tttctttaat gtgggtattt gtaaggaata gccccttaa    3600 atctagattc tgttctcaaa tcaagcaagc tcaaggctgt aagcatggat tcaccaactt    3660
tcctgctcaa ggaatttaaa tgtctggtct ccatcatatt actttaatag taatagttta    3720
```

```
ttatacacat gtgccagctg tatatccctt tcttcttga tggacctatg aactctgttg    3780
aggtgagatt tgaacccctt agaaggtgct agagaagagg tacctgatgg tcaaggcaag    3840
gctgatactt attcatgggt cccacatctg ctaatgtaag caataacaga taatatgctt    3900
tgtgtttaga cccacagtgg ttgcatgtac actaagtatg tatcatcatt gtcttatcgt    3960
tcctttagaa tacagctaat aattatgacc gctattctca tagcatttat attatatgag    4020
cattgtaaat tattttgaaa tgctttaaga tatacttgag aactatgcat atcatgcgta    4080
tgttgttcta ccagctggga ccttgaaatg agatcccttg aggccagcat aaagagaaag    4140
ttttcatctc aaacaaacaa aagatacact tgataataga tgagggataa atgtcatact    4200
ttttatatag tgattgagaa tctacagatt tgggtatcct ggtcacttag agaccaagg     4260
gaggactatt agctctagag ctatgaactt tatctccaga ttccaaagcc aatacaaact    4320
ctagccaagt tggggtgctg ttacctgtat ccctctgtca aattccaagt gttttcacca    4380
cctttactgt atctttccaa ctgttctctt ttataaccac acatagttca tggtctttcc    4440
ttctctcact tgactgtgga gtaacctaac ttgcgtgttt ccagttttcg atctcttcct    4500
taaatctaca ctagttaacc acaaagaccc tcttttctga gctgtgtcta ttctatcact    4560
gtcaccattc cttaatgctc tcccagatgc agccaaactt cactttgggc ttgagagtct    4620
tctccaggtg acagtgacta atgtctccag attgagcatc taccatctac cctgtgtatt    4680
acacatgaat agccttagct tttcagcaat agacagatag atccatagtt agccatgtca    4740
acacccttct tcatgctgtt ctcacagtaa taagtcctaa ttcctgtttt ctcccatcta    4800
aactcaaccc tgtcctaaat accttactca aatcctaatt gtatctcttc cacaaacatt    4860
tcccccttct ctccattaca aggtggaaac tcagagatcc aggtgtcttg catgttgttg    4920
attctgtcct caacaaggaa ttccccaggt tcctgcacga aggaaagcat ggaggaccat    4980
acttgaggct actggtgtag tgggaagaca ggcccaaacc atgtcacaga aacccatcac    5040
cagaaagttg gggaggcag cccagttgtg gagcaggaga aggagaaaac aggcttgggg      5100
aactgctagc tatgctttgt cacagtcaca agaaaaaagg gccctagcct ggcctacata    5160
ttctacaact tcctgaatct ttgctctgaa atgaagaggt ttggatggct gtctgggaat    5220
tcatcttgct tgcagtgaag ctccttgggg tatttgaaac caggaagttt gaaggagttg    5280
atgctaattg ttttctaaag tgtgtgagga gtactggcag agttcaggcc ttgtgaggaa    5340
agaatcctat atctagtctg cactcctggg cacatgagac attcagctat ctcccttata    5400
aagcatagaa agtactcttg tacttgacac agaaataatt tcagtatgta gagcattaaa    5460
aaaaagtatg aatgacttag agagatggct catcagttaa aagcacatac tgctcttcca    5520
gaggtcctga gttcaattcc caacaaccac aaaaactcac acatatgcat gtgattaaaa    5580
ataaaatctc tctctctctc tctctctgtg tgtgtgtgtg tgtgtgtgtg tgtgtgtgag    5640
tgtgtgtgtg tgtgtgtgag tgtgtgagtg tgtgtgtgtg tgtgtgtgtg tgtgtgtgtg    5700
tgtgtgtgtg tgtgtgtgtg tgtgtgatgg tgggcttgtg tttgcaagcc cagcactagg    5760
gagttaaggc ctcactcaca gtgccaggcc agtctaggtt acagtgagtt ctagacagcc    5820
caagctacag agtaaggtac tgacaaagaa agaaagaaag aaaaaaagaa agaaagaaag    5880
aagaaagaa agaaagaaag aaagaaagaa agaaagaaag aaagaaagga gagaggtgag     5940
agggagggaa ggaactggaa gggggaagga gggaagaaa agaaaaagaa acaaccaaag     6000
gaacaaacca ctgtatgcca ttatacatta gctttgggct ttacaggtta tacactctat    6060
attgtcatag ccaatgtctc aatattccat aagaggtgtc tagttgtggg tatgttcttt    6120
```

```
cttagtcctt ttatttagac tacatgacct gttttttgcct aataggccat tagtaatact    6180
gacttctcca catgctgccc tcaaaactta ctcctggaag atctttattt aagctatgaa    6240
cgaaaatctt aaccctgtga cctgccaccc agaatgcctc tgggaacaac ctcaggcaac    6300
ctatcaagcc gcttttccaa catttggggc aacaggatt aaaattatga ttgttgtctg    6360
cctgctgagt tcaaactcac agagggacca gaagctgact cactgatatc aagcagttct    6420
aaattttcag tttaaaactc taattattaa acagggatg tcctcagacc agcactcaag    6480
agaaggagat aggcagagct ctatgagttg agttataggc cagcctggtt ttcatagtga    6540
gttttagctc tccagagagt taccagcaag accctgtcac aaacaaataa aaacaaacaa    6600
acaattaggg gatatacata taactaaatg ataaagcctt acctagcaca ttcaagtccc    6660
caggttcaat tgctagccct gggtggggat ttggacaaat ttaaaaagac ctttttttgta    6720 tcacacataa atatgactgc actggttgtt gtttttccatg gaaacagaat caatgtggca    6780
tgtattttac ggcattagct catatagttg tgcaggctgg caagtgtgga atgtataggg    6840
caggccagga atcagaaatt gatacaaaat tcaggaaaga cctctgggtg caatggtgca    6900 caccttttaat tcaagcactt gaaaggcaga ggcaggtgat ctttgtgagt tccaggccag    6960
cctggtctac atagtgaatt ccgggacagc cagggcttca tagaaagaac ctgtctcaaa    7020
acacacaaac aatcagaggg aagggcttat tttgtttttg agacagggtc ttctatgtag    7080
cccaggctgg cctcaaactc atgctcttga tatgcccacc tcacaagtgc atgttaagat    7140
tacaggtgcc tgacacacac cacttttgtg aagtgctgaa gagtaagccc agggcttcat    7200
ggacgctggg caagcactgt gccagctgag ccacactccc cagtgtgcac gatactttgc    7260
aaagatagat ccatatggat gctgtgcttc tatctaaaca gaatgacaac cacactctgg    7320
caggttctgg ttcataactg agtcttattg gtcacctcct tctccatttt tcgctggtat    7380
ttctcaagga gagaccacaa atgagaagtg aagcctaact tttaatgcgg tctctcctat    7440
gtcacctaaa ttctagctca aacagggttt ctggctctta ccttttcctc gggtttctgg    7500
atacttgaag tgttaacggg catttctctt aaagaccaaa tctggccaga ttcaaatggc    7560
tggccttcaa ctcggcaaac taggaacaat aatgtccgct gcatgtggct tgtagcactc    7620
tgtttctatt catggacttg tgagtgattt ctgggaaaca cgaattataa gataagtcct    7680
tttcagtgga cttcacaagt tcaccctcag gtagtatact gtcaggtaga aacgtctttc    7740
agagaagcga gaggtgacaa gccctctggg ctggccattg tccctgctgg cattgaacag    7800
cctgttcagc acatgaaagc atcgcctgat gctcccaaag ctggagcact ggcagccccc    7860
tgcagtcagg tgtgtagggt gggttagcag gggtgcttag gcgggttttg tagttacctt    7920
ttcaacacaa atgcaaaagc cagagagaga gagagagaga gagagagaga gagagagaga    7980
gagagggaga gagagagaga gagagagaga gagagagaga gagagagaga gcaggaaagc    8040
atccaggctt tgaagcaagc cagccttcag ctctgtcctt gagccattct gagtggaatg    8100
gagtaattgt ctgcttggag aactgaagaa tagcacatgg caaagaacaa tttgtacctg    8160
gaatatattc attagcttgc atgtcaaaag gccacatgca gatagaaacc attatcttgg    8220
cattctttaa aaccttgcag ccttgagact tgaggtgcag aaaccacat gcccatgtga    8280 ctgactacct gtcgatctct ccagccctgc ctggctaaca gggacaatat aggggatgg    8340 tgggaggga cagcttagac tcctgtggac ttggattgaa agaagaacag ggaagacagg    8400
ggactgtgca aataagcact ctattaggac ctatttttgg tgtcttggga ccctcctact    8460
```

```
ggtttagctt aaattgagag gggatttggt ttgcctcact agctgtttct tcccactcaa    8520
ttcacaatta cagcttttctt cattgtcatt aaaatacatt aaatgtgtac ttgttggggt   8580
aaggctttct gttgaaatct gcataaagac aatgtccaca gcccccagtc agtggaaaga   8640
gcagtaggac cagaaggcat gtgtttccat cccgagtcta tattggaatg tttgttaaaa   8700
cctgcacttg taagagacaa acactagaac catcagcttg caggtctaca ggccagtgtt   8760
gccagtgcag ataatgccca aactggaacc taaagatgaa ggcctttggg agctgaggtg   8820
gaagagtcag ctgtgatctc ccagatgtcc tcctcatgcc ccattgccac tctagcctcc   8880
cacctccaag cacatttggg atccaactgc taacccctgg tgttctttc ttagttgaaa    8940
ttctcaggga ataacctaag agtctctgtc actcagtcta tggcatccta tgataacagc   9000
caaggctaaa tagccatcat tgttcttttt ccagatgctc agcaatgagg atgcagaggt   9060
gaacaaaggt ggttcagggc tgccctgatg atgaatttga caagccagaa tctaacaaga   9120
tcagtcggta aacagaatcc tccttcctat ccagagatgt tggcttgttc tgtcactgga   9180
tgggcatcat ttactataag tcatacaggc accagacact cagagataaa taacatgaag   9240
tttccagtct tatgcagtcc tgtctagttg acttgccagt attctcaagg aagttccacc   9300
ccagcccctg gcatccatag accaaggact ctggaatgtt ctgggaaagc tccacctgag   9360
ctcctagcac ccatatatcc aaagagtctg gaacgttatg gtggaagccc cacctctctc   9420
tccccagacc tcgcccccctc aaaaagtcca ccaaagactc ccaccccccc acacacccc   9480
agatgctcaa gaccacttcc atagagtatt taaactgcct cccagaaaac agaattcatt   9540
ttttcagtct ctcttcccca tgtcctctca gggtggggggg cagggggtatt agtattcaag  9600
cacctatact ggcctgtcct tggggttctg acaagatatg acctcagcta cagccactaa   9660
gatcaccacc tgtgtatatc cactatgctc ccttttaaaa gggccctgtc cacctcccat   9720
tctctctgtc tctctctctg tctctgtctc tgtgtgtgtg tgtctctgtc tctctctctc   9780
tttctctctc tctctgtctc tctctctctc tccttctctg cctgactctc cctccctccc   9840
ctgctctctt ctttcctgct gcttttgtcc ctagaggcta gtctcctctc tccccttccc   9900
ccttttccca ttcactttcc cccaataaaa aactctccac ccaagctcta tcacatggca   9960
tcattctctt gctccatgat tttaaaatca caatgaggag gggagcatgg aaaaattatc   10020
caggaagact ttatccatta aacctgggtg ctttttcttt cttccttcct tcctttcttt   10080
ccttctttct ttcttccttt cttttttcct ttcttccttt cttttttcct tttttccttt   10140
cttttttgttt tgttttgttt tgagacagcg tttctctgta gctttggaga ctgccctgaa   10200
actcaatctg tagagcaggc tggccttgag ctcacagaga tccacctgcc tctgcctccc   10260
atgtgcttga attaaaggtg tgcaccacca ctgcctggct taaaactggg cttttttctaa  10320
gtcagtttga tttggattgc tgcattggca gagaggttta ttggggtgca gaaacctttc   10380
aaccagcttt tgagctaatg atagagagaa gctcaaggaa ttggagcaat gcttgactag   10440
ggatgtcaga gggaggctat ccagaggagc ttacaactga ggtaaactta aaagttaggg   10500
agtttgtcaa cttcaaccca cagaatagag cagagccagg aggagctgag gcttctgagt   10560
gttatggtgg aagcatcacc ccaacccttg acatccatat gcctgaagag tctggaatgt   10620
tatggtggaa gttccaccca agcctccctt cccggtcgcc ctccaaaccc tgctacatct   10680
cagaaatccc accaaatgat gactccctcc cccagagata ttcaagacca ctcccacagg   10740
gtatttaaac tgccccccaa cccccagaaa atagatgtgt ggttttccaa tctctctttc   10800
ctatcacgtc tctggggagc tggcaggcca tttgggagca ttgtatccat taaacgactt   10860
```

```
ctcagtggag actctgaaag ccagaagagc ctagacagat agatgtcttg catactctag    10920
agactacaga tgccggccca gactattata tccagcaaaa gtttcaaaca ccatacaaag    10980
tcaaatttaa acagtatcta tctacaaatc caatattaca gaaggtgcta gtaggaaaac    11040
tccaaactaa gattaactat acctgtgaag acacaggaaa taatctcaca ctggcaaaag    11100
aagaaaaacc tctctctctc tctcctctct ctctctctct ctctctctct ctctctctct    11160
ctctctctct ctctctcaca cacacacaca cacacacaca cacacaccaa caccaatacc    11220
atgaacaaca aaataacagg aattaacaat aattgatgtg tgtgtatgtc cctgtgtgtg    11280
tgtccttgtg tgtgtctgtt tgtgtgtctg tgtatatgtt tgtcacctga ggggtggctc    11340
ttccttggtt tgtgaggttt ctacccaatc tataactccc ttttcttcat tcacttcctc    11400
atgtccttac tagtctctat tgtggattaa ggaaactgtg tggagaacag ttttcttcta    11460
gaaaagaaca ctagccatct catgtaatca aattggtgac tatcctaatt attatgagag    11520
agcttccgtc cagtaagtgc tagaagtaga tgcagagatc cacagacaag cactgagcca    11580
agctccagga gtcctgttga aaagagagag gaaggattgt aggagccaaa gagtcaagag    11640
catgacaggg aaacccacag agacagctga cctgggcttg tgggtgggag ctcatggact    11700
cttgaccaac aattagggaa cctgcatgag gccaacctag gaactctgca tgtgtgtgac    11760
agttgtatag catggtctgt ttgtgaggct tctagcagtg ggatcagggc ctgtccttgg    11820
cgcttgagct ggcttttggg aacctgttcc gcatgctgga ttaccacacc cagccttgat    11880
gctgggggaa gcacttggtc ctgcctcaac ttgatgcgcc ttgcattgtt ggattctcat    11940
gggaggactg ccccttctg aaaaagaaca aggagaagtg aataggggag gggattggga    12000
ggagaggaag gagaggaaac tgtgataggg atgtaaaata aattaaaaaa ttaattaatt    12060
aaaaaagaac acttgtactg gtagattggc taaaatgaaa caaagataaa agtacacagg    12120
aaaaagagag gagaaacctg gggaggggggg ctccaaagag aggtgagggg gggatgggaa    12180
tggcagctta gtggaggaag gaagacatga cctacacgaa tcgagctgta gttttatct     12240 ggagcatagg gtaaagatgt ttgaggagaa ggaggaacac atgcttgtaa acatggtct     12300 tcagaaccag caacaatcat acagagtgtc cagggtccat gggcacatga aggacagacc    12360
aacacatatt taacagtaaa gtgtccatat ttggtatgaa agtgatgggt aaattgtcct    12420
gggactgtaa tttagttgta aaggacttgt ctggcatgtg gtattcttg ggttccctcc     12480 ttagcactga aaaaaaaaaa aaacacacac acacacacac atatattcta gtgttttgta    12540
gaaaaggatt caaagaaagc catgatttct cttttgataa atccagaata atgtaataag    12600
aacacacagt ggtgtgattt cagcaatcaa gtacaggttg cttgtctgtt tgttgtatgg    12660
gatggttggg tggttgtttg cttggttgt aagatgggtg ggtgggttgg tgggtggttg     12720
cttggttggg tagttggttg ggtgattggg tgggtgggta tttggttggg tgggtggtgg    12780
gttggttggt cgtttggttg ggtggggtgg gttttgtttt gagacaggga tttactctat    12840
atctcagttt gtctcaaact cactatgtgc acatgagtat gtgatgagat tatctaagac    12900
catagtgtct gtgttcatgg aatgtctctc tagcttagag aatttaaaaa atggccatgt    12960
agggaaaccc ctcagaaaag gagtttctat ggcctccaag aataagaatg gatcctccta    13020
gctcggagtc agcaaggaac tgaagccctt aattttatag acacaaagga atccattgtg    13080
tggctccttc ccagccaagt ctcagatgag tcacagacct gcatggcacc ttatgcagtc    13140
ttttgaggtc ccaagaatag gatgcagata agccatgcca gaatcccaac acacaaagcc    13200
```

```
ttagtgatat agtaaatatg tattgtgtct aggctgctgc atttctggtt atgctactgt    13260
gcagtaatac acaactaata cagatgtgat ggttaatatt atgtgacaac ttgagtgggg    13320
cacagaggta cagacacttg gtaaaccatt ctgggtgcac gtaaggatag ttttggatga    13380
cataaacatt tagattagta tgctgggtaa aatacattgt ccatcccaat gggcatgggc    13440
tttgtccaac tagatgacag ctggaataga aaagtctgcc tctctcatag ttctcaggcc    13500
tttgagctca gactagacag aactcacagg ttctctgagc tttccagctt gatgaatgtc    13560
catggcagtc ttcacactta acacctgaca gacttaatga tcatatgaac caattcaaat    13620
ctgaccatca ctcgggtcat tcttttgatt ctgtcacttt ggagaactaa taccgaggac    13680
ataaaatgcc atcacatcgt tatttcttc ctgtctgtga atattttct tttttttctt      13740
ggttttttt ttttttttt ttttttttt tttgttttc tctgtgtagc tttggagcct        13800
atcctggcac ttgctctgga gaccaggctg accttgaact ctcagagatc cgcctgcctc    13860
tgcctcccga gtgctgggat taaaggcgtg taccaccaac gctcggcctg tctgtgaata    13920
tttaaaatga aaactttgga aatgttctga accagctgg tgtcagatag tcagagaact      13980
ttcgtaaggt aggtgtgggt tatagcataa tcccacacaa gaggctgaag caggaggatt    14040
ttgtgtttga gggcagctag agccacatgg tgagtccctg cctcaaaaca caaaagcaag    14100
acaaaaacaa gctccaaata agattcactg ggccctttct ttccttcctt ctcagtgagt    14160
ccacttgctt taaaatcagg tcttaaagac gcactagatg ctgaacttaa cagtaataat    14220
aaatatcttc tcttacagta cagattatgc tctataaaca ctgcactgat aaagttcagc    14280
cttaaccttt gttctgtaaa tgtttcctag tttttctact gccgtattat aagacaaatg    14340
tcagcatgaa ggcaggtttt tcagaaaaca cagcagctcc acagatggcc tctaatccat    14400
aatcattaaa gacaagactg caacttttc aactggaaat cattcaagat gtttttctga      14460
agtccctacc aggacacaag ccaccctggt tgctgtgtga catcagttag gtagactctg    14520
aactggcttc ccaagaaatt atacaaaagc aaggtgtcac ctagtattag cataacttct    14580
gataactact gtcttagctg gggtttctat tgctgtgaag agacaccatg accacagaaa    14640
ctcttataaa ggaaagcaat tattgggtcc agcttacagt tcagaggttt aatccattgt    14700
catgattgca ggaagtatgg tggcccacag gcagacatgg tgctggagaa gtagatgaga    14760
gttctatatc agattgacac acttcttcca acaaggccac acctccactc actctgagcc    14820
tatggggcca ttttcattca aaccaccaaa gctacaaggt agcttatacc ccagcttgct    14880
atttctgatg agacttagta aatagtctta aaagcccata aaatgactca aaactagttt    14940
ttttattatt attattagtt caaattagga agaagcttgc tttacatgtc aatcccttct    15000
ccctctccct catcaaaact agttttttgt ttttaggtt tttttcaag acagggtttc       15060
tctgtgtagc tttggagcct atcctggcac tcgctctgga gaccaggctg gcctcgaact    15120
cacagagatc tgcctgcctt tgcctcccga gtgctgggat taaaggcatg caccaccaac    15180
acctggccaa aattagtttt aagtccagtt ctaggagctc caatgccctc ttttggcttc    15240
catgggaacc aggaacacta tatatatata tatatatata tatatatata tatatatata    15300
tatatattca ggcaaatatt tatgcatata aaaataaaat aaatcttttt tccttttttt    15360
tttaaagaag tgacattgtc ttggaatttt tgtggctgct ctgcccttat gtgtaactgg    15420
acactaccag catctaaaca ctggcctgaa accagccaaa gaaaaccttt gtgccaggtc    15480
ctgtgtcaaa gtattatgtt ccttttagga tatcctatat cctaaaggat ttatttact    15540
gatagcatct taacttcctt tgaaaggttg gtcttctcaa gcagtcctcg tggagctggc    15600
```

```
tcctcagcta atgccagggg acaataatga tcccctccca aaaccaaaca gaaaaccatg   15660
gcaactctgg tttccttggg cagcacctgc tttaagaatg agcaaatgac caatcagctc   15720
atgaaactaa atactctatt attactaaaa tatttttttg agacagggca tggaattcat   15780
cacatagttc aggttggcct tgaactcaga gagactcact tacctttgcc tcccacgtgc   15840
tggaattaaa ggcatgaacc accacaccaa acataacact tgaattttgg aagagtcctt   15900
cttccaatag atttgaggtt ttgaaaatgt ggcacagaaa atatgaattc aaatataatg   15960
aaaacaagag ataactttca actaagtttc tataggttct tgctaggaat cctaagcttg   16020
tctgaaactc tagagcttct gtttctagct tctgagtgtt agtattgtag gtatgtgccc   16080
tgcctcagtg tgatgttttt gataatctta agaaatcaa agaaatttta taaaagacta    16140
gactgtgcta cacaaaaaga atattcagat gccaagaaag agttcttaga aattaagaaa   16200
tatgctacta gtataaatcc tttataaagt ggaatgacaa atctgatgaa atcttactaa   16260
aagtagaaaa acataaacat caaagacatg aataataaga aaatcatatt gtgcatatga   16320
ttaacctaaa acattaactt gcaaaaatag aatagtccca aaaagtaaac aaaataaata   16380
aatcaccaag aacatgatac aaggacaatt cctaggatga taaaacaaga atattcatta   16440
taaaaggccc tatcactaaa gcacaacaga aacagactca aaagataaat cttcattgtc   16500
actggagaga agtccatact atcatagcac tcagaaggaa ataaaaatca aaatgtcaaa   16560
aaggacctca gcctctgaaa cacaaataca aaatatgtcc cgccttcttg acacgcatta   16620
ctcttcaatt aacattttaa gaaaactata aactgttaaa gagagcttag tattttaaga   16680
aatctgtagc tatttctttt ataagcatga caactaagtt tccctgattt aaacagacct   16740
aaaaaaccgg tgaagtgagt ggagaaaggg gatacgaaga cagcatccca catgactgct   16800
cccagtaaag gcaaggtctt catccatttt atcctgaact ctgggaaatt tataaagaac   16860
agaaatgtat ttctctcagt tctggagcct cagtccagga cactaagtct aggtactaca   16920
ctctcacatg gtggaaagta gaaagcaagc tcacttgtca ctcactacct gatgcctctt   16980
tcatcaatcc cattgataag gaagagacct ggcatctcag tttcctaagg actcagctct   17040
tactaacatt agctgtcatt tctgggtcac tgtaacagaa agcctgacag aagcaaccca   17100
ggggaagaag gatgtatttt ggctcactgt ctctgaggat ttcaacttat cccagcaata   17160
aagggataaa ggcattgcag caggaatatg tgtggcagaa gctgtttatg tcacaataaa   17220
caaataaaca cacgctagcg cgcgcgcaca cacacacaca cacacacaca cacacacaca   17280
cacagagaga gagagagaga gagagagaga gagaggggg ggggcagaca               17340 gacagacaga gagggagaga ggcagagagg gagagagaga gagagagaga gagagagaga   17400
gagagagaga gagagagaga gagagaaatc aaaggcccac ctccatcaga ctggtcccat   17460
atcccaaatt tctagaacct cctaaaacaa caccatcaac tgagggagac attttggat    17520 tgaaagcata atgccattac ccaggcagaa tctgcctgtc tgggggagtc acatttaagc   17580
catggtatca attgacctca tgtaatttca gaatactaca taaaactatc agatattttt   17640
catgatgaat ttctaaagct tgaaattccc tttgaataaa ggaccaacta cagaattttg   17700
ctgagtctac aattacatac atgaaaatgt aactacgaag tggccagcca caatgaaaat   17760
taaagtgttt gggtggtctg tctctattga tgctcttctt tgccctgttt tttttaata    17820 ttgttgatgg tttgttttc ttttaagata cttggcccca agaaaaaaaa tgacagcctt   17880
aattaatttt gtttactctc ctgacatttt aaaagacaaa tttatgaaga cctgactgtt   17940
```

-continued

```
ccatgtagta ttagaaagat gtaaaattaa gggttgctta agctgtgtag aattgaagag   18000
cacagcattt gagtgacagg gtacaattag agatcatcag ggatgtggca caaagtgtac   18060
tcaacctcac cttttcctgc ttagcagaga acagggtgcc tcggtgagat aggaaattaa   18120
tcaaatagaa gaagaaatag taattttaga aggatcaaat tttcctggtt agaatgatca   18180
aaactacaag acttgtaact aaaatatagt caaacccatt tcaactggaa tctgtgctat   18240
tcatgtatag attaactaga atctaatttt taaatttttca tcttacttcc aaaaatattt   18300
gtccaaatac tctgtgaatg cattagtttc ttatgggaaa acatcatatc ttttgtacaa   18360
tgtgtttctt agcttgaggt tctctccaaa caggaccaag acgaggccag gaccatgtga   18420
tacaacccat agtcctcaag aaatagttgt cattttctta ttccaattgc atcccaaggt   18480
ctcatctcat tttgcgtgtg cctttgacac cccatacccca cataaactaa ggtggtgtta   18540
tttttttgagg ccctgaaggt atcttcagga atccataagt gagccttaag ctgcatctgg   18600
atataggaat ctgaaagtgt cccttctctg catgatctct tctttcagtt tttcaagtca   18660
gtgtgccaca ggaatcagga acgataaatg gagaggggaa gtgcagttgc ttggtataga   18720
cacccccagag ggctatttgc atcctgtcct tcaaaatctc tctgagcctt cctgcctaag   18780
ctgttttgag ttgggtttgt ggtaccagaa ccccctgcccc cgccccattc tgactaatga   18840
gagagagaga gagagagaga gagagagaga gagagagaga gcagcagagc atagaatgaa   18900
agtaggttag aagggcaggt aaaagcactt tagacaagag caggtataag ggccttggac   18960
tccctccccca gaacacacac atgaaggtaa acgatggtta aaggatacag ataggatgtc   19020
gaagctggac gatcacttgc ttttgtgtgc ttgaagtgac aggctgtggc tttcgggttc   19080
atggggtctg ttgttgagtt cacagtctca ccatgttagc aagcatgtca ctattaagct   19140
ctatccccgc cccccttttt tgagacatgg tcttgctaac ataccccagac cggcctagga   19200
agcactttgc agtctcagct cccctgagtg ctatgatcac tcgtgtgagc tacagtaccc   19260
aaaccagaat atgtgtgttg ggtgttatga gagtttacac attgctgcct tgaatgctgc   19320
tctgcttgag ttcctgtagg aagctgagct gggaacctaa gcttcctcct cccagatagc   19380
agtaaccctg cagagacctc ccaccaagac tagctaaccc ctccttcttg tgctgtactt   19440
agcaagaacc ccaaggttct gggtccttgt gctacagttc cagaagagta tgaacaatct   19500
tagcttttct gtatatgtgt ctgtgtctgt cctgtcagat caagtcccag cctcactgta   19560
tgcaacatga aaggctgtga aaactgtgca ttttgagaat gaacatcatt agtctccagt   19620
aagttcaaaa acaaatgaag gcagccactc ataagggtct ttaatgaggc aaggggggcaa   19680
aagggtggtt tctgtttgtt caaagaagcc tgtcatacat tttcagaaaa tttagaaaca   19740
cgtatcatgt catttcacgt tagtatgaag tccttataat tcatttcata ttaaatgatt   19800
tcctttggtt agaagcaaaa ttatgcataa aatgtgttcc tttgtgtttg gagcaaaatt   19860
acaagttaca ttattagtta atattctagt tcttattttt cccaatctcc aagaagcaaa   19920
atattcccct aaaccctaaa gcatcaaatt atcctatcac acagtgacca gtcatcgtaa   19980
cctaaatatt aaagcatcag attatcctgt ctatggtgac cagtcattgt aacctaaata   20040
ttattgtaat gtggattaga gttaactata ccttttcatc acactataat gtaaacactc   20100
tccaaatctt tcaaagtctt gaaaacacaa tttataaata ctgtgttctg tttgttttga   20160
gacctgatcc ggttaggaat ttcaggctgt cctcaaactc atcatcttcc tgcctcactc   20220
aggtcctaag tgctgagatt aaaggtctat gctaccacag ccatacgaat gccatgtctc   20280
catcagctta tcacttctta acttttttct tttcttcttc tacatactgc tgagtaggag   20340
```

```
catcgatgac ctcagcctag taggaatggt tcccatgtga acccttaatc tgtaggaaga   20400
tgctggactt cttccattaa gactgatctc catttgaact tgacttgtct ctctcttgtg   20460
tggagctacc atcccatata taatcttctg gtttataaac agattgcttt accctcaaga   20520
tcctttgcta gcgcagcaat gtaagtttta atacaaacag taaggtctct gattggagtg   20580
tcatggtttg gttaagtgcc ctttccaagg gcccatatag ttaagggctc aaccaccaag   20640
tgatgcttgt ggataggagg cagggcctag tggacagtct ttaggtcatg gagctatgct   20700 gttgagggg  actgtgggt cctggtcttt ttcccactcc tttttaggtc ctagctatga   20760
ggtgagtggt tttgtcctat caagcacctc tgtcctgcca tggtgtaatt gattataact   20820
acaacctctg aaactaagcc agtataacct atttatctca agatgtaact tacaggtaat   20880
ggtaagataa agctaacaaa agacaaattg ttataatcca ggcaagcctg ccccatccc    20940 ttgggggcat ggcacagagt gtgtcaccca tctgtgcatg gcaagcagta ccctgactct   21000
gtatgctgat tcaaaggtcc cttaaagcaa actcctccca cttcctctct ttttctgcca   21060
tttctctgag gagggaggcc actgtctctc tgtctctctc tgtgtctctt tttctatctt   21120
cctctccctc tcttcccttt ccccaataaa cttttccacat taagtttttgt ctgaaggtat  21180 ctgtttgtct ctcacccgcc ttttaggccc cacctaccat gggatctgcc aaaggtctca   21240
cctcgagctg tattcataac acaaatgaca gacaaagatc aaccctgaag actagtagga   21300
tgtagaaggc ctggagctga cctgaagaac actgctgact tcaacattgc ccatccgtca   21360
gttatgtagc attaaagtta tagtggttcc tcagaaagca gtctcctttg aaaacttctc   21420
gttttgtgtc taaatggaat taaataccttt gttcccgaat aattgttttta gttctcttga   21480 aagatcccgt atacttacta ttaagatgta tataaacctc aagctgaaag aatgacttcc   21540
cctatggcca gatcacaaga ctctccactg atgtgcccgt tgcaacctga ttagaggaag   21600
agggtcaaag ttccccaaga ttcagctgag ttcatgcaag ttttagaaaa aaaacaagat   21660
gttcctccac agttagaaag gagtgggct  ggagggatga ctcactgaga aaggttattg    21720
tcgtacaagc atgaagacct gagctcgaag cctggcaccc atgtaaaaag aaaccatgca   21780
tggtagtgtg catcttcaat cccagcattg gggagacaga gaaagagaaa gggacatccc   21840
tagagcttcc tggtcagcca gccttggcaa gccagtgaac tccaggttca gtgagagacc   21900
tgtctgggga ggaaaaaggg agggagggag ggagagagag agagacacac acacacacac   21960
acacacacag agagagagag agagagagag agagagagag agagagagag agagattgag   22020
gaagatacct gatatcaacc tcacacactc atgtacccat gtatgtaggt accttcacac   22080
acacacacac acacacacac acacacacac acacacacac acacacacac acacacacac   22140
acggatggtt ttgaattcta aggctcttat ccacacatat atggagacaa atagaagaat   22200
tacagtcgtc cctgccttttg acgctactct gtttctccaa ccctgcttcc cagatatttt   22260
tcaacatcta ctcagccttg agtggttgca ctctgacccc aggacctctt tctgtgactt   22320
ccttggcctc ctgttttgtt tttctgatgc taaaaactga atctgggcc  tcatgcacac   22380 aggaagatgc tataccaatg agctacaatt ttgttgccct ttttaatttt tgagatggtc   22440
tcactaaatt gttcaggatg gcccacttgt aattctcctg ccttagcttc ccaagtagct   22500
gggcttttat acagatctgt gcttccacac ctggctgagc agacactcat gatttcattt   22560
ctgctaatca ggtagttttc ttgccctcg  ctgccatttc ctacctgcct ttccttgcca   22620
actaaactgg ttcccacaag cgacaggcta tcatttctca gctcttccac aggttagctg   22680
```

```
tgcaatttgg tatgaatcat ttagcaagcc cagttctcct ctttgtaaaa cagatgattt   22740
agatgaaatt ttttcaaagt tctctttgaa ttaaaactat cactgccttg cttgctctct   22800
gactcttgga gaccatggcc tatccctgat tagtccttgg tccacagaag gatgggtggc   22860
attggatgtg ctgaacaatc aggtactttc atgtcacttg gagtcttaca gtaactgcat   22920
gtttcaaatg aatcctttct ggctctatta gtttcttttt tgtcactgtg aaaaaaacac   22980
ctgaaagaaa caaggcacgg tttgttctga ctctcggttc agaggatata gttcaccatg   23040
gaggcaggag cttctcacag ctgtaacagc catggagtca ggtggctagt tacagtcagc   23100
tggccttagc agtcagagag ccaagagagc tcagttgagg agagtccagc caggctgtag   23160
cccttaggac ctgctcccca gagatccact ttctacagta tcttctaaac agtgtcacta   23220
gatggtgacc aggtagtcaa gcacatgagc ctgagggata atatcattca aaccatagga   23280
ttagtctaga actgaaccag atcaagaacc aggttttctt ctcacataat agataccaca   23340
catcatgttc tcatatagag tgtgatctag gtattgtttc tccaaatgga gaagccaaca   23400
ctggatgact tacatagaaa gaaagagagg gaggaaacaa gcaagggagg gggaagagtg   23460
agaattattg gaacagtacc agtgcctcaa aatccttggt ggactagaga attagcctca   23520
ggaagaagcg actaggcttc ttacagcata gacatacagt tcttaccaga ggcacagcca   23580
tcatgggtgc catggggagc atgaagttca gctccatcca gccattccta gcgatttctg   23640
gcaacctctg tcctttgaga cacttcctga agatataaga gtccaggag agacatctga    23700 ttgctttgat cccaggatct tgggatggaa ttggtgttgt ctctgctcca gctccagggt   23760
caggaaggtg aaactggaaa cacaagctag cttttcttac ttagcaaaaa cccacaggtg   23820
acataaaaga cagattgaca cgagaacagc atggcagatt tatttagtca aagttttacc    23880
agacacaagc accttcagaa aggtaaagtc agagaccttta ggggaatttt cttgccagaa   23940
tttttccaga agaatcaaca gccgtgtaac aataggacta gataaacaag taagactgga   24000
cctgcagcac aaatgtgaca ataggagttg gaatccccag gactcacata aagccatggg   24060
agccgaatgt aatggtcact tgtagtttca gcctcagatg ggggtgggga ttctccagaa   24120
taagcaggct agcaagacta gccatgttgc caagctctgg gttatattga gacactctgc   24180
ctcaatgagt aagtggaaga atgatggagg ccaacttcaa ccttggactt ccacatgaac   24240
acacatacac aatgcaacca tgcatccaca gtgtatgtac acacacacac acacacacac   24300
acacacacac acacacacac acgcaaatgg acaaagaaag aggtaaaacc tacaaggaat   24360
caactgaaca gaagccaact ggtctgcctg ttcagatcct ttttggcctc tctgtgtgct   24420 tcccttctc ctgggcatgg ggcaggcagg atctgtatgg ggtgagggtc ttcagagaag    24480
cgaacagcct tcctaggttt tatggctcag tttggtggag aggggatcta gtttctctta   24540
atcatctttt taaaaattta ttaatttatt ttttatattc caatcccagt tttccctccc   24600
tcctctcttc ccctccccca cctcccatct gttccttaga gagggtaaga cctcctctag   24660
gaagtctact aagtctgccc catcatctca ttgaggcagg accaaggcac ctctccaccc   24720
ctacactctg gtgtctaggc agaacaaggt atctctccat atagaatggg ctccactaag   24780
tcagtttgtg cattagtgtt agatcttgga cccacttcca gtggcctcat atattgtccc   24840
agtcacatcg ttgtcaccta tattaaggga gtctagttcg gtcttatgca ggttccccat   24900
ttgtcagact ggagtcagtg atctctcact agctctggtc agctgattct gtggtttccc   24960
catcatgatc ttgactcctt tgttcatatt gtcactcttg cctcacttca attgtactcc   25020
aggagcttgc ccattggtta gttgtggatt tctgcatctg cttccatcta tttctggaag   25080
```

```
agggttctat cttctctggg gttgtgaatt gtagactggg tatcttttgc tttatgtctg   25140
gtatatgctt atgagtgagt acatacaaca tttgtccttc tgggtctggg ttaccccact   25200
caggatgttt ttttctagt tctgtccatt tgcctgcaaa ttttagaatg tcattgtttc    25260
ttactgctga gtagtactgc attgtgtaaa tgtaccacat tttctttatc cattcttcag   25320
ttgaggggca tctaggttgt ttccaagttc tggttattac aaataatgtt cctatgaata   25380
tagttgagca aatgtccttg tggtatgaat gtgcctcctt tgggtatatg cacaaaagtg   25440
atatttcagg gtcttgaggt aggttgattc ctaattttct gagaaatcga catactaatt   25500
tccatggagg ctgtacaagt ttgcactccc accagcaatg gaggagtgtt ctctttactc   25560
cacatcctct ccaccataag ctgtcatcag tgttttgat cttagccttt ctgatcagct    25620
taaaatggta tctcagggtt gttttgttaa tcatcttgag aaaaaggaat tctattttct   25680
gtgactggct ctgagagaga gagaagaggg aaggtggga ggaatgtgtg ctttcaagac    25740
cttgtgttct cccttagctc aaagtactca ccatgaaaaa ccaccagcct ttggaggagc   25800
atgctcttgc agaggcaaga tcctggcttc ctcccatctt gaatttgcca aaatagcaaa   25860
gatgtttggg tgctggacag ccaaaaatga cagctgctca cttcacagct tcctcacgta   25920
tgattacaac tccactcatc atcaagcttt aattacatca tgagcaggct tatggctgag   25980
ccgttatcct cgcatccctt cgtctcatca ctgattcaca caaatcacta ggtgctccgg   26040
ttaatgaaaa catattcatc agtacagtga ctaattcatc aggccaacat ttacatggct   26100
cctctgcatg acaaaaatga atgtttagaa tgaataatga gtcaccagag gtgggggaca   26160
tcttctgagc acaggttgcc cttgtctttc ctggtactca atcccggctg aagagctgaa   26220
caaagctgag gttattttc ccatgacagt gcattgtggt ttagagatct gtaagcggct    26280
tatcttgatt ggcagtttga ttggttctgg gatgtactaa gagacgtgcc tcatgggcat   26340
ttccagaaag aattaactga gggggaagct cctcgcccg agaatgggta ggagcatctg    26400
gtggggtaca gatgtaaagt ggtccaaggg agaagccgca tggcctgcct gccttcactc   26460
cttgctgctg agtgtgttta tcccatctat cccgttgttg cttctgttgc agttgcaatc   26520
ctgcttctcc aggccccagc gtagactgaa cagtggctgc ccagaaattc caattgaag    26580 cagccgaatg gtggactgag cacctctcag tcttcagtct ctctagtttg taggcaacca   26640
ttgttggacc caactcttag tagtaagcca atctactaaa tacagaaagg ccagtgagat   26700
ggctcagtat aggtgcttac caccaagctt ggtgacccga gttcaatccc caagactcat   26760
aaggaaagaa ctaactaccg agagttgttc tctgagctcc acacatgctg aaacatgggc   26820
ctccacatgt catgaacatg ttcacacaat acatatttat ctctatatat tcatttctta   26880 taattttag aaaatttcat tttatgtata tgagtgtttt atctgtttgt atgtctgtgt    26940
accacatgca tgcctggtgc ctgaagaagt cataagaacg tatcagattc cctctaactg   27000
gagctaaaag aagattgaga ggtacctacc atctgagtgc taggaaccaa acctgtgtct   27060
tctggaagat cagtaagcat gcttaaccac tgagccatca tgccacttat ttgtaacaca   27120
tatccatcct attggttaca gtcctgactc atacagttag atagctgagg aacctagaat   27180
tcttctgctt tttattaca aaacaaagaa ttttatctga cttacagttc tggccttagt    27240
cagggagctg cattgggaga tggcttctct actgtcagag tccagaggtg gccgtaaagt   27300
atcatatgac atgaggcaga aagtctaact tacttgagag ttaacttgga aatgtccaaa   27360
gagacagggg gctaagtccc tcttattgaa gagaccttcc atagaagtta gcctgacaga   27420
```

```
tggccttgcc tgaactgcat tgacagtctt acttggaagg cctgttttgg ttcctaagaa    27480
attcaaggat ccaccagaga agtgtgcagc cagcaagctg gactccctat cccaagcccc    27540
agctcctcct cagggacctc agcagtcctg tgtctagctt acctcagcga tgggggaaa     27600 gatgctgttt tcctgctaag agcacactat tttatattat tgttgacaca ggttggactg    27660
catgtaacag actctccaac aacacagtga agatacaagt gtgttttgct gcatttaaat    27720
gtctccccat ctgtccctgc taagacacct actgtccttc acatgtcact gaaaactcca    27780
ccccttatga aagtcttcc ctgatgccat ctagacaagc taagagtgct ctgctctgca     27840
ctgagcagct tctcaactct ggggttatca ttgctctgca tcacaattag cacacgtggt    27900
agtggctgtg tttgtgtttt tccacaccat gagtccagac agcatccctc tcaccagcac    27960
gccataggca caagtgctca agagtagcag gacttgaaca tgtgtggttt atcatacaga    28020
cagctgctgc tcagagacca gatcaaattc aaagcaaaat agagagatga tggttcctgc    28080
catgagcgta ctgaacaagg acaaacatca ccatcataag gaactcagct gacagggagc    28140
ggtcaccaaa cttttttttc tgtaaagtga caaaaatagt taagtatttt gccctagaca    28200
tagtgggtgg tacacatgta atctcagcat ttgtcagagt gaggcagaga gttgaatgct    28260
gggctacgta gatagtctca aaaaataaat aaataagtaa ataaataaat aaataaataa    28320
aaggaagaaa taaaaaaaag aatttgttac tcaactctgc acaatggtgc aaaagaaaca    28380
ataagcatta tgtaacctag tgggtattgg ctgtttcact ttactaacag gcattgaaat    28440
ttcaattttg caaattttc atgttccata ttacccttat ttttattctc ccctataaat     28500
ggtgactcac caatacgcaa ctggataaga ttagggtatt tttattaggg aatatgcctt    28560
acttacagag cacctaacca gccagcagga aacatagtaa agtagcgcat gccgatgaaa    28620
caaggaaaaa gaagaactac catgtgtgac ccctaacccct taaaacctct cccacatcac   28680
cctgaccatg cccattaggc gtggtcacct agccagcccc taggaggcat ggttacggtg    28740 tcccctaca ctcccctaat catttaaaga tgcaaatgca tgcttggtga tgggctaacc     28800
ttggctcatg ggctaatctt ggctcatggg ctaaccttag ctcatgggct aataatcaag    28860
gtttactaat ctctgtcaga cagccatttt tttttgcag agaagaatcc ccatctttgg    28920
atcatttatt tattcctttt gtatatttga tgcaatttat aaccacaaga acctactatg    28980
tgactgcact gtgccagatg gcagagaaag ctaagccccg attcttgtgg catggactca    29040
cacaactcca gtacaggact gttagtgaca atctccttaa ggcataagca tactgcagtg    29100
gcagcctctg ggttaggaga caaggataca gtttatgaca cctggtatct ggaaggcatg    29160
aaacatgtca aatgctggct acacctaaga atcagcaaca tctagtctgg ccatagccta    29220
ggatgaatgt cacagggtct taggccagaa atgtatggcc gagctgtagc agggtcctct    29280
ctagggccag aattaattcc agtgtgatgg acagccaaga ccacagggat aacaaatgag    29340
cagtgccaat gacacgtgct tctccttatt attgctgcac agtgtttgtt acacatagca    29400
ttttcgcaca gtaatataat gtgcttgggt catcttgctt catatcccat cactccctcc    29460
atctccctag tgcctcccct gttacctttg cttctcagtt ttgtttctgc tttgatgtca    29520
acagcacata caagatttta tgcaatacat cacttcctga atggctctat ttggaaatca    29580
ctaaaaggta atttatggaa catttggggt cttttttgatt ttctaattta ccaaaaaatc   29640
cacctgggga aagacaatgg agttcaagga cttctaagag gggaatgtac catggtatgc    29700
tccagccagg ggaaccagtg cttcccagga gctatggctt acaaagtggg ttatcacatg    29760
aaagcaagac taaaataatc atctcaaata ttcattagat gtgggactcc taaccatctc    29820
```

```
acaatgcctc cctcggtcta cattaaataa gaaacctcca ttttgtgctt tgcgagaaaa   29880
tgactgaaga ttatacattt ggccttgaag tggaagtatt tttgaaaatc atgaatagga   29940
aaataataaa tctctcattt caacataaaa tataagggac aaggacatct actcatgctc   30000
caaggacgga cactgaattt tccatcaggt agttgcagaa cgctgtgtcg ctcaatcaaa   30060
aattcaggat gcattgctca gagtgcatta tattaaaaga tagcatcttg gaacacagga   30120
tgctcaggaa atgggaggga cattaatctg catgcagtga tcatctcctg caaagcgggc   30180
atgagagcct gatgggagac aagccatcca gatgcccata cccaggggag ctgtactggg   30240
ctgcagccct cgccattca gccatgcacc aggctactcc ctcctcttcc agctttctcc   30300
ttctgatggc cataggatta aagataagg gactctagtg caggtcaact gctgaccagt   30360
gtgaaaatgc acagactaca tgctggtaga tcagcacttc aaactactgt tcaccatcat   30420
ctctggaata agcactacat ttacagggtt caaacctcaa tgaatataaa caaacaaaac   30480
acacctccct tccttcactg tctcccattt ctttggttcc catctccaca tagaatttat   30540
aattaaaatt tctaagtatc tttccagaaa tacttcacac atgttataag caaatgtgct   30600
tttaaagata ctattttaaa ttatgaaaat ggttatatta gttgagataa aagaatagaa   30660
tgggaagttc cagaatttaa ggcctcatat gaaaatataa agcgctttct cttttaagtc   30720
tagggtaggt gtactagatc agcgctcagc tccataccat gaagccatcc aggagtcaga   30780
cctctctgac agccctgcca ttgtcacaga gaagtttctg tcaccagtgc tcatgctgtc   30840
agaggagcga aggagaaaag atgtgagacc tcccaagtca aagtcatcta tggataaaac   30900
cttagttgca tggcacacca gtgttaggga gtcgggaaaa cacagccata gcccagcttc   30960
ctctctgttc ttgctcttat taccaccaga aagaggttgc ttagacaacc caaaccaaga   31020
cacagggctc tgtgggaggg aatcagtccc aggcttctgg cacatgctat gtcaccggaa   31080
agccccagcc ctactccgaa tccccacaag tacagcaaat atcagattat agcatttaaa   31140
ggggcactct tgccaaagag aagcaccatt ggaatagcca tgcttgagaa ctggtcctac   31200
ttactgcaga accatggata caggctcccct tttgtagatg ggcttaataa atacttctat   31260
aagtgatact ctgctttgtg aaaatgacct cgtcaatatt caaagtaatc ctctggttta   31320
ggactactat gaacctgtgg ggttcattgt tcatgtggtt aaacagcaaa gagtagttag   31380
acagttgtcc tacgtcacag aggggacat atgctatgct tggttaaata gctgtcctgg   31440
tcagagggga ggcatgctat tctgcccttt ctgacagacc ctgattgcat agacatttca   31500
gtgagataaa ggaaggaagg gaagaaggag gaaagacaac attttttgct tctgttaagg   31560
tagagactat ctgtgatcca gttcagcaca gtgcctgtga gtagaagcta caggtcaggc   31620
aggagccaag gaaatgtatt gcttttctaa ttgaacaaag gacacacagc tgccatttat   31680
tttcttcatt ttgacccttc agccctgcac tgtggatatg acatcaagaa actaagcagc   31740
cattttgtga aaatgagatc taagttagta aatgtggctg aaaagaagc cagctgcatc   31800 ctccctggat ttacgagggg gaaatgtagg catactaaat taaaacacta aaattgaccc   31860
aaagctattt tgactgatat ttaaatatag attctgctcc tggacattcc agagttcata   31920
ggacagttgc ttctgttcag aggattcctc ttcggggttg cctctccttc cttaggcctg   31980
cttgtcctgc ccaaagctgc ccaagtgcat caggccccaa accaacttct ccatcctgac   32040
gcacagcaga ctaaatatgc aactttgtgt ctcttcatcc caggacaaaa ctttcaccca   32100 gccctgaca tctgagactc tactacaggt tatctattaa atcttttata aagaccaaga   32160
```

```
aacaaagtgt tggcatccaa actttggtaa atcatagcct tttaataaag tcaaatggac    32220
caatgtactc taacaaaaaa atatgggtct ctcatttctg aatggcagat ttcaagccct    32280
aagaaccaca atgctcacct actgggcaac actgagttac agagacccag ctcccccacc    32340
cctcaccaag ccagagaaac actctatctg aacaatcctt ggtccatgga gcaagaatta    32400
gacatagaat ttgtatctca ttgtttttta ggaaaacccc aaaggctatt atgaagtcag    32460
tttttctggg cacctttcct ttcccatgac aacgagttgt gggcagtctc agcagaatac    32520
tgaagctgtg gcttggggag acagagcata tactggattg gagttcatgg gtgggtgcat    32580
ggaatcaatg ccgggcatgg gattcaagac cttatgcatg tgggtagatg ctttgttact    32640
gggataaatc ccccacctgg gatctgactt caagcacaat ctttggaagg cggcattggc    32700
tctctgctaa ttttttctagc acttttattc cacttatttt ctgcttgttt gctttgggag    32760
ttttgttcgt tataagacag tcttgctgtg tatcctaggc tgatcacaaa cctgtggcag    32820
tccttttgtc agcaggccaa aattcccact ttatctctga agacagaaag tagattgagg    32880
aatatatgat aaagacactc atcaaagcca ggcatctatc tttacttttc ttaaagcatg    32940
tttttgaatg gcataaaacc atgtagacaa ggagtcttat gttgtacatg gtcctacttt    33000
gtcacttaca ataggata cttttcaataa gcttggtagc ccttgcccta ttctacttat    33060
tctgttctct cttcctcggg tcttggggag ccttcttacc aggtggggtg cataaaggg    33120 aaaagtcaca aagctcttcc tattcctggt tcccctccta agtgtacctt gctggtggcc    33180
ttgctagcaa atgtagtata acatctgact tatctcctct cagatatggt tgttgtactt    33240
agataaattt aatctagaaa ctcaagctgt atgtctttgg ggaccagcat tacagagctc    33300
ttcccttcct gtccttacct caccttggct actgtagtaa gttaatcctg atgattcctc    33360
catgagtcct gaaactgatt agttccaaga gctggaggat gagaagggat atagcctggt    33420
gcagggacac tttccaatga ccacaagacc ttgcacaagg tacacatgga atgtgttaga    33480
ctgtctcctt tctgtcccta gcctcagttg ccccagtgtt tatcaatgtt tattaacatt    33540
gccctagcaa aaatactaca gactaggaag cttgggtaca attgaaaaga gcttctcagg    33600
gttctggata ccgggaagtg caaaggttca gcatctggac agggctgcta ttgtagtttc    33660
aaatggttct gctgcaacac ccctttgaga gaatgaacac tgcttttcac atggtggaga    33720
gtgcacagac accaacccaa ctcctgaagg ccctttctcg agggctctaa tccatcatga    33780
gggccatact ctcaggactc attacctccc caacatcccc tctctaaata gtaccacact    33840
gcatttgcat ttcaatatat cactggagat atataaatct ccagaccaca gcataccata    33900
aatcagataa ggcaggcctg ccttctatag cctttcactc agcaaaggtg tttctagccc    33960
aaagcagtct ggactctcac tctgaaacct cttgggagtg gtggccagaa atgacttccc    34020
atcatccctc tctcctgacc tggtccagca ccaggtcacc aggaaatcct ccaagtttca    34080
ttatccccac ccccaattgt ctcttgtctc tagcaaacct cttccaatac ttccttcctt    34140
ggtgggtgta gcaagccaga tgatagcctg ccaaagaagt tcacagcctc atttctggag    34200
cctatgaata tgttacattg tgtggtaaaa ggaactttgt aggtgtgatt aaattatgaa    34260
tcttgaagtg ggcagattat ccaagtgagt ccagtgaaat tgcaaaggta catcaccaac    34320
agtgaggcag gaaggccaga gggggagaag gaagcagaga ggcagaggga ggaaaagaca    34380
agccagggga ggggagtggg gggaaagaaa ggagagagag agagagagag agagagagag    34440
agagagagag agagagagag aaatatcaca cacacacaca cacacacaca cacacacaca    34500
cacacacaca cacacctgaa cctgattgtg gaggaagaaa ccactaacca aggcattcga    34560
```

```
ggcagccttt gaaagtcaca agagacaggg aaaacagatt ctctccctcg gcccttcaga   34620
atcaacacag ccccacaact gctgatttta gtcatgttaa agccaagttg gacttctgac   34680
tgccaaaact ttagacgagc aaataaatct gcactatttt aagataccaa tgtgatttgt   34740
tcatgaaaac aatcaataag gaactaataa agtagaagtg aaaattggat cacttctgaa   34800
gtttggtaat atccacagaa actggacaca tgctgacttt gtgagccata gctccacacc   34860
caggtatgcc ccctacagaa atgtgtatat aggtgggcag gagatgtcac ctgctgtgtt   34920
catagtcgca cctttagact ttcccaagcc tgagaatagc ccaaacacct accaggagca   34980
aaataaattg agatatacag acgcagtggg atactcact tctaaaagaa tgagaaaacc   35040
acgctataca ctgtatatcg tcggaacagt aacacagggg tgacaatcag gcaataggac   35100
atattctcta tggctttaga aaacataaaa atagcataac agttctgtta gtggcaatgt   35160
gttctgtttt gtgatctgta tgatgcttcg gtttgtgcaa aagctctgga cttacctttt   35220
aaatgtatgg tggtctatac cttttaaatg tatgctagat atacatgagt aaaaatgatt   35280
aaaagagatg gaggggagga gactcatgcc ttcataaaag tttgttctgt cctttctggc   35340
actgtccaag tgaatgtgtg taaacaaaga gtgacccacc ccaggtagtc caccttctta   35400
gaacctactt ctgctacaac atgtcctgtg aatgtgcacc aaatgtttac taagggatca   35460
tgccacaggg ttttgtttaa ataaagtatg tctacctagg ggtatattga ttgtctttcc   35520
ttttgagggg gggtctcaaa actacaaact agtttgtttt gagacaagta tgtagcccag   35580
gatggccttg aactcacacc ttctgtcctg cctctttccc agcactagga tggcaggtga   35640
gactatcagc ctggcccag gaaactatct ttgattgaca ttatctggtc agaaaagatc   35700
taccttttcc tccaccaggt cctccaaata catgaagagc tgaaacagtt ctgtctaccg   35760
aatttccttt tttcttgatg tttctgtgga atttaataca taaatttaa tttgcatttt   35820 tagcttttct attaagcctt aattagagta taatgaagtt atgaatttat aaaaataaaa   35880
acaaaacggt tgctcccaca atcactcagt cttgaagtga ggttctgact ttacctgaag   35940
tgggggaaga gagtgaggaa agggacctgc ggaagctgaa tctcagaccc acaagatgga   36000
tctgagatcc atccaagcga acgtggacgc agacccggag tagggacatc caggggtcat   36060
cttcatctgt cctcgctgtg cttctgcccc tttgctcctc taccagtctc agctgtcaaa   36120
gctcagtggc ctggagggga gatggggcgg ggcttaggat cgaaggcgga gcctcggaga   36180
gcatcttctg gccccgggg cctggactgg cccgccgccc ccacctgcag cgcggcggag   36240
cgcgggcgcg tcactcccag cggaagcgcc agcctcgcgt ctggcgaggt gcgcgcttcg   36300
cggctcccgc tccagagctt cgtggcccgc ctgtgtctgc agagcagggg cgggggcccg   36360
gcggcaccga ctgggcactg agatccaagt agccactgaa tcgtagacag tcacccagct   36420
cggacagcgc gtcgggcgg gagcagatcg ggaaggtgaa ggaccactgc ggatccgaca   36480
gcgcgtccca ggtcagtcct cccgctgcac ttggggaaac tttgggatgc ggtgacggct   36540
gcgagatgag gacactgagg gtcgcgaggc gcgtggccc ctgtgaaccc cgcgaacccg   36600
tacctgccgc gcacctgaca ccgcagctgc cagggcgggg accganaccc tgctgccgcg   36660
gaccactgcg ggccaccaag ggctagcggg cttcaggggc ctctcgggag cctccggctt   36720
gcccgcgccc agccgcgcgc ctccggtcct cgcgggtccc cagctccttt tggcggctcg   36780 cgccccggacc ccgcggggct gcggattccg ccgtcttcgg gcctcgtggc gctgaggag   36840 cggcccgggg gcccatggct gcagggtggc ggccccgcgg cgggagcggc gcgtgctcgg   36900
```

```
ccggtggagc gcgcgggtcg cggggttcgg ctggagcgcg tggccgcagg tgcctgtggc    36960
cgctgggcag cggaggtgag agcgcgggct ggggacgcgg agcggattgc aacctctggc    37020
tgcaggaacc agggtcgctg ggtgagcagt cctgtccccg cggcttccgg gcgtgcacat    37080
ccctggcacc cggcatccag accccatcag ctggaggcgg gctgcagagc ggcgcctgcc    37140
cgggccgagg accagtgcct cctgctctga cacgccatct caccaacgag ggcggggtgc    37200
tagattggcg ggctgcgcgg ggaccactgg ccagggcctt ctggcacaag cccttttcgt    37260
ggacagctgc ctgctctggc ttggagtgga ggagacgaaa tgagtacccc gcccccatca    37320 gcgcccccaac actgtcgccc cagtcacctt cctttgccct tctccgacag caccttggac    37380
ttgctccctc ccgaattggg gaaaatctga ggaaccagg cagggacctt ggagataccg    37440
cagcctgcat actcaacagc ctggaaatcc agtcacttg gtacctcgct gcttcccaga    37500
cactttggag gagcaggttt gccatttcta ccccacatcc gtacccatc cccgtccgt    37560 ctctgctgag gaagggactc ttatgagaga agttgggatc taggtacccc ttaaggtagc    37620
cccagagtct gtggtaacta ggctcatagg taactaaaag gcatcctagc tctgtagctt    37680
tgtgagggaa acaaaccta ccaactaatt ccttcccttt ctgaatattt cttagaagac    37740
tggagaccaa cggaagccga ctgttctggc cagtctttgc accctttgct tggctctgac    37800
tctccttcct aggcagagaa acattttgct tatgacctct ggctggcctc cttccaatcg    37860
ctgcctggcc ttggactgcc catcaggact gtgattttt tttttttta agacctgatt    37920 aggaaaggct gcaagcctcc ggttctagaa ggctcaaact caggggtata ctcttctctg    37980
atacccatgt gctccctaat tccactgtgg caacacctct gcccttcact cccacaagaa    38040
aattggttgt caaacctctt ggggaagatg atggaggcat ccctgtggga gcagatgcag    38100
gatttggaag caaccaggaa acaaccagga gtgaggaatc ttttttaaag gctcacatga    38160
ttctggaact aagaaaagat ggagatgcca ccagtgtatg aagcttggcc tctcctcggc    38220
ccatcccacc caactcaggg aactggcata tgcaggacct gtattgggtg atgcatattt    38280
ggaacctagt acttattgaa ttcctaagca gtaaacacat tccgaatttg aaattcctca    38340
caatcatcta ctgnaatgta gatattaaac ccccaactta tgaatgatag ccccaaaatt    38400
gttaacattg agagagccca ggttccctgc cacctcttcc acaacaggac aggaactagg    38460
acaatgaata ggaccatttg agctttaggg tcatgtgccc actttacagc tccatagcca    38520
gacaactgtt ttataagaga gggcacaaag gaaaatcact gtcctgtcca aatgaataga    38580
aagctgggga tggtggcagg acaaaggcaa caggaaaaat catctccaac aaggctttcc    38640
aagcatatca gtcttatact actgccatgt tgggtaccac acaaatcagg tatctcaaac    38700
tggacgctgc ctaggaggt ctgtcatcta aaaaggcagg gagatattga gataaaatac    38760
acagaagcta gtatttaact ccaggctggc agataatagg aatgaccttg ggagggtgtg    38820 cttaccttc cttctctctt gaacaaaatg tggactggac cagatgagca ccaaggctcc    38880
accaactcta acagaccttg tgtggtgggc ttgcctgcaa acagacttga gctaggttgc    38940
tgtgcgtggg atccattcca gactcattta caaactcgta gtcagtgaaa tgtgataaac    39000
cgaacactgt agggatttct aaacaaggaa ttaaaaaact cgactccaaa tgggagagat    39060
gcaggcaaca aatcgacagt gtttatgtgc ctctgaatag ctttgatttc cttcggtagg    39120
agctgacagc tggctgacag aaagctcacc cagggagaga agagagaaaa atcaagtatg    39180
agattaggaa taatgttttc aggtaacttt ctattcccat tcggagtggg tgtctggaag    39240
ggcgagtgta gttatggctt gaattgctcc atttatccac agatattttc ttcccaaggg    39300
```

```
ctcctgattc taagatgctg ggctttgctt ctgtctccta gtttcctggt agcagggtag    39360
agagctgggg gtcccagcat tcagcctgca tattcttcct ctatcctcac tatctgctgc    39420
ctccattatt tgtggtcttt tggatctatt tggtcagaga gtcagtcttt ggtttcttgc    39480
cctggaaact gcttgttgct acttgtggtg ggggcagcat ttggaagtcc aggtgctctg    39540
cccacaaact ttcaacccat catttgtttt tcatcccttt ctcattgcca ctttgtgtgg    39600
tgcctgggac ttctgggacc tatagttcaa gggtcatata taccaatggc tcacatgaca    39660
gcactgatca ctctgccagc tctcctctct ttgcaaaact tatttcagat ttttcatttg    39720
acaatacctt tcctccagtt gtctttattc ttggcagcat atgccttgta acctttaaaa    39780
aggaaggtaa ataatttgag aaaaaatgta ccaagtcctc agtgatacat tcttactaaa    39840
gactcccagt tttaacaagg agtgggctg agccatggc tcaacagtta agagcactac     39900
ctgctcttcc aaaggacaca aattccattc ccagaaccca catggcccct tccaaacatt    39960
gataactctc gttccagggc acctcatgcc ctttcctggc atctgagaga accagcataa    40020
acatacatgc aggtgaacat tcatacacat aaaatgaaca ttaaaaaaga aatgaaatag    40080
agaaagggtt tacataacta tttaataact aagactgcct aataatgtag ggacccataa    40140
agaaaatcta gtaagttttt acaagattcc actcaatcag accaaacatt actgttactg    40200
acagagtaaa aagtcacttc caatagtcca agaacaactt tgtttcattt ctcaggcact    40260
gtctgttttg tggcatatgt gcatggtgtg tgtgtgtgtg tgtgtgtgtg tgtgtgtgtg    40320
tgtgtacagg tgaatgctgc tcgtgtatga gcacatgcag gtgtgtgttt gcatggtgtg    40380
tagacagagt ttctgacctg cctggtccca cagctgtttg gccacaaata aacatacaga    40440
ggcttatatt aattagaaac tgtttggcct atggcttagg cttctcactg gctatctctg    40500
tcttaattat taacccataa ctactaatct atgtatttct acgtggcgtt atcttaccgg    40560
agaatacttg gtgtcctatc ttctcagcaa ctacatggcg tcttctctct gcgtcttctc    40620
cccagaattc tcctcgtctg gttgccccgc ctatactttc tacctggcta ctggccaatc    40680
agtgttttat tcatcagcca ataagagaaa catatgtgaa gaaggacatt tccctatcaa    40740
tggtgtgtgt gtgtgtgttt gtgtgtgtgt gtgtgtgtgt gtgtgtatgt gtgtacatgg    40800
gtatgtgagc acatgtgggt atatgggtgc atgtgcacct gtgtgtgtgc atggtggcta    40860
gagttgaggt tagatgtctt ccttggctgc tctccacctt tttttttattg aagctctcac    40920 tgaacttaga gctcactgat tcagctagtc tagctacccg gcctgctctg ggggtccccct   40980 gccttcactt tccatgtggc taccatatct actttacatt tatgtgggta atggggatct    41040
gaactatggg gtcctcatgc ttgcatggca agtgctttat ggactaagac atctttctag    41100
cctttacctt tttttttttt gaaagagttt tttttgcta actgggaact caacaccaga    41160
tagctagtct actggtcact gaggcccagg gatctactat ttctgcttct cttcccaagt    41220
gctgggacta cagactgtac caccatatcc atatttcttt tagcatgagc tctggaagtc    41280
aaactcaggt cctcacgctc acaaagtaag tgttttatct accaagccat cttcccatct    41340
ctgttgtttt aaaaggcttt gaatatggga tgtgatgaag ggaggtgaaa ttctgagata    41400
aatttcttga aagaagaat gaatcaagta ggagaacctc ctcctggtgc tgtctttcag     41460
ttccatgtcc acacagcata aacattatga ttatcattcc acagattgta attagtcttt    41520
ctctgttttg ccagtctgct cccaaaaaat gacacagaga gacttcttat taatgatgaa    41580
agctttgcct tagcttaggc ttgtttctaa ctaactcttg taacttaaat taacccattt    41640
```

```
ctattcatct acctgctgcc acgtgattca tgacttttac ctctctctca ttctgcatat   41700
cctgcttcct ctgcttctgg ctcatgatcc cgcttttctt cctctccgag tgctctgtcc   41760
ccagaagtcc cgcctaacct cttcctgcct agcaattgcc catttggctc tttactaaac   41820
caatcacagt gacacatctt cacgcagtgt aaaggagtat tctgcaacaa caggtgatga   41880
agccaacatt ccaagaggcc agggcttgcc tagggcacat agctaactta agaaaattag   41940
gatcgcattc tacatctgtc tgactctgaa ttggatctga actgtgactt gcatggaaga   42000
cccaaagacc ctgagaaagt acaatgacaa agggctgac tctgtccaca tggtgttagc    42060
ccaggtttcc cacaggagga aaacccatcc taggcaagag aagtggtctt catcaaacac   42120
tctatgaaaa gcaaatcaga ctcaaatgtc aggatttgtg ctttacagat cgatccggta   42180
agatgaaaga acttcctgaa agtgtgtgaa ggcctaaagt cagggctgtt catgaaggc    42240
actgactaca gaatgaggtg ccagaagcct agtcagagcc tctagggaat aaagtgtcag   42300
atgatcttct aaaaaagttg aagtttcacc agtaacagaa tggccccact attaaaatgt   42360
gagcaaactc agaagtcatt gtagcatata gaagcacaga cctatggatt gctggatgga   42420
gcccaggtat tcactccatc ctgaatagcc agctggggag ctagctcagt cagttaagta   42480
tttgctatgc aaatctgagg accagacttt ggtctcctgc atccacagaa atggtgcaca   42540
cttgtaatct cagcactggg gaagcagtca gccagatcca acagctgcct agccagcgga   42600
aacagcctta tcagaaactc atgggtcctg gtgaaagata ttatctcaaa taacaaggtg   42660
ggaagctcct gaaggacact ggaggttaac ttctggataa acataggctc gccccaccac   42720
cagtgagcat gtgcctaaat ccgtacataa caatgatgta aagatggaat tcattccagt   42780
gaaaagtaag cctcctggac tcttttttt ttttttgttgc tagatattct cgagacctca   42840
ggagagaagg tttgccatca tctatataac atggtactca acttccctgt agtccacaac   42900
attcctattt ctatatgatg gagaagaggc cactgcccct cccagacatc tcagtctcaa   42960
atttgttacc agttccctct cctaataagt gcttagggtt agtgttgtag agaagggctt   43020
tacatgaagt gtgtgtgtgt gtgtgtggtg tgtgtgtgtg tgtgtgtgtg tgtgtgtgtg   43080
tgtgtgtgtg tgtgtgtaac ctaaaggctt tccatgtttc cacactgaaa ggttcttaag   43140
actgagaaca accagataag agtccaaatt ctagaaacca tgggaaagtg taatattgaa   43200
agtcagaaca aggcatggtg gtgctcacct tgaaacccac cacttggggc agaggcagtc   43260
agatctctgt gagttcaagg cccagcctgg tctacagact gtacatagtg agttccaggg   43320
ccagaactac atagtgagat cttgtctggc caaaaatata taagtaaata aaataaatca   43380
gtacatggta acttgttctt atttcagtgt ctgtttctca agcatgactt tggcttaagg   43440
attttttccca acttgttttt gtgattgcca ctgtatcatt tctttgtgtg aagttactaa   43500
gtggtttctg tatttgatat tatgttctga cctagtttct tttcatatta aacccatttg   43560
tatatgaaaa ctgcaaagaa gtgggttttt tgttttttgg gttttttttt gtttgtttgt   43620
ttgtttgttt tttcttggtg ttctcatgtg acctttccaa tgtttgcttc cagaatagac   43680
ctgcaagttg ggatccacac tgccatctga agtcctgcac cccaagtttc aggtatgttt   43740
tgatggcaga atagcttttc tagactgtga caataggggc ataaagccac aaagcattcg   43800
cttttcctaca ggttatgcac ccactctctg agtgattggc tgtgcatcat gaatattatc   43860
aaaatggagg cagttcagtt tggagtgctg tcttttatgc gcttattcat ggcaatgcca   43920
atggaacatt cggcaacata tactactaat catgcatggt aactgaactg tgttgtgcaa   43980
ggaagacctc atatgaccta ccttttgcata tgctgacctt ttctgtgaca gactcctata   44040
```

```
atactgagag tggtactgta tggaagagtg tgtgaaaatg tattgtttaa ataacagaca   44100
gatgcctcta aatacaacac ccaagcagag aaatggagca tcactggcac tttggaggcc   44160
tctgggtaac cttttccagat cacactgttt tccttcctcc accaataacc actttccctt   44220
tggatgctac tcatagttaa catctttact tttgttgttg tcccactgat gctaagaaaa   44280
ataacttcaa ctagcaagca caacactaga tgaattaaga gtgatattga ctgtgtgtgg   44340
tgagtctcag aagactagct gcctcaggat tcatgaatgc ttacaggaac cctttagcaa   44400
ggtcaggaat gagtcttagg atccatgtgg ctcatagtct ccagcctgga catggagtag   44460
cacagtgtct gagtgcccca agggaatggg cttgttcagg ctcccctccc cgtccccagt   44520
tccaacaggt ctcagatcca ggacatcaga gctgagtgaa gagcagagct aaaaggagca   44580
ccatcggagc cctagaagca gaataggggg ggacacagca cacagagaca gaactgagg   44640
ccaggctgct gtgtgctttg ggcctaagtt gacagatgaa acatggtagg gtgaccacat   44700
ggaggatgtc tgtgcacatc catcaaactg gcaggtcccc ccagcatttt ctgggagctt   44760
ggggtcctct tttccatgat cttcagcttc tgtattctat gtgcgctgtt accatttcat   44820
cttggtagag tctatccttc tgttatttct tgagagtatg tcccaattct tgcctggagg   44880
tttggctaaa tatagaattc taagcagagg gtcatttctc cttcagatat ttaaagacac   44940
tttctgtatt gtgcctcatt gccattgttg atatacctga atctaaattg atcccttggt   45000
gcgtgactta tccccacagc caagggcccc ttcccttctg gtctgtgctc tggaagtctg   45060
caggcacatg gtatgggtag ccactgtttc attcatagtt caatgctccg ataggccctt   45120
ttgatttgat aactctatcc cttttccccca ttcccgttga tgatttcttc ttttgttccc   45180
cttttgatat agtttccttg ctgatgctgt gctaaaatat tcctaccaaa aacaacctgg   45240
ggaggagagg cttcatttgg cttacaattc cagctcacag tcattgaggg aagtcagggc   45300
aggaactcaa ggcagggagc atggaggaat tgcctgctgg cttcctctct gacttactca   45360
caggttcttg taggctagct ttctgataac atctcaggac cacctgctta gcaatagtgt   45420
ggtccacagc aggtttgaac cttctgcatc agttactaat caagacattt gcccaaagac   45480
atgcccacag gccagattga tgtaggcagt tcttaaatca agtcttttttt gtcaagtgac   45540
tctagactgt caagtcgaca gttgatgcta actaggacac tattctacca cttttcttgg   45600
tagaaatatt attcggatat tggagttctt ggactagttt ttctggttct ccttttcttt   45660
cttttcctgt tatttatatt tgttttatga gatagggtct ctctgtgaag ttgtcctaga   45720
ccttctggcc ctcctgctta taattcctaa gaactgatat tacaggcagg tgccatgagc   45780
ccaacgtttt ttcttttctt ttcactgcac tctgtttgag agtctcatcg tcacagtcat   45840
tcacatcttc tattgtcttg tttttctttt taaatgtgca ttggtgtttt gcctgtatgt   45900
atgtctgtgt gagggtgtca gatcttggaa ttacagttcc aaataatatt tctaccaaga   45960
aaaagtggta gttgtatcct agttggcatc aaatgtcacc ttgacagcct tgagtcacct   46020
gagaagaaag acttgattta ggagctacca tgtggttgct ggtaattgaa cccaggacct   46080
ctggaagagc acccagtgct cttaactgct gagccatctc tctggcttcc ttctattgac   46140
ttttgcaggc ttctttcttg ttcttttgca atttcatggt ctctgactgt tcttcacaga   46200
ctccttacctc atgcttaaga tgtctcttac tccttcaagg atactgagtt tttgaagttt   46260
taattctcct gactactgtc ttttccctcc tgtttgtcat tctctgtttg ccctggcctc   46320
tgtctttcat gcaggaagac ttttcatttg cttttaggtt tttattttaa ctattggttc   46380
```

| | |
|---|---|
| atgactaaag ggctagatga aaaggccagt gagaaggctg gagcatatgg gtgatacttg | 46440 |
| tcaaccggga gcctcactgt ggaatgcttc agtggcatgt gaaatcctgt ggtatttgct | 46500 |
| caggcaagtg cagctgttga atgcagacca gagcagcttc cttcgaagga gtcagatgtt | 46560 |
| gctgactgtc tttctgcagc tggtcaggaa ggtgggatag acttcagctc ttttcaaaca | 46620 |
| gtggtcacca aacaaccact tgcccagaga ctttgtgctt taccattctc agagaacaga | 46680 |
| cctctggatg gccccatggt ggaagcagcg cacctgtcta tcacaggtgc tctgaaggag | 46740 |
| ttggaagaac tacccattgt ccacatttcc cacattttca catgccagct tcactctggg | 46800 |
| atctgggtga cagtggggct gacataatgg caggggttgc agtttcagac tcagagtatg | 46860 |
| tggtaggaat gctgctgtct gagggaagac tcatctgagc agtggaggct ttgcctgttc | 46920 |
| cctggcatca tttgacctgc ccctccttag aactgggaac cccagttcta aagctccctg | 46980 |
| ctttaaagat tctgtgttgg ggtaagttct tagctttctc aggctaggtc ctctgctctt | 47040 |
| gggtttccac ggcactgttg tttttccctct ggctttgtga gtggttgtct tttgaaaaac | 47100 |
| tagttagttt ggaaaatttt gggagggagt caaataagat gtatgcattt tgccatgtaa | 47160 |
| gtcctaacca agccatctgc tgtggtattt tcctgagttt ggttctgccc ctataggcag | 47220 |
| agtctgtcat cacagataat tgcattttga acttgagcat ctcccttcct tctttgtctg | 47280 |
| cctgaaaaag tctctttata aaaaaatgta atgttaattt aaaaagtatt cattattctt | 47340 |
| gtgttgtgat acatgagtat atatatgcta tgatgcatat gtgcaggttg gaggacaact | 47400 |
| ttctgtagtt ggttctctct ttctcccttc atgtaggttc tggggatcga acccaagtca | 47460 |
| tcaagcttgc acaacagcac ctttaccttc taagccttct catcagccct tttttattg | 47520 |
| attgattggt tgattgattg attgattgat gctagggata gagcctaggg tctttacat | 47580 |
| gctaagaaaa tgctctacca ctgaactgca ctcctagccc aacctgctaa attcttacac | 47640 |
| tgtcttcaaa aagaagctct gatgctggat tctgcaaagt ccattttat ccctaaattc | 47700 |
| ctaaagctgt ttaaatctcg tgagtcttac tgtacagacc agctctgtgc accatcttcc | 47760 |
| acaatctcca tgacctcctc aggatgggct ggtatctctg cagctctgcc cagtgcctac | 47820 |
| caggaactta caggtgtcac caatgaattt attggtgcat gctcacttca tcttgtccct | 47880 |
| atccactttc tgctttgact ccttctggta agagacaagt gtgttaacta cttgtgctat | 47940 |
| caccacacag aaatccatat cccataatct tagtcctttt tatttactta tttttgagac | 48000 |
| agggtcacac tctgtagctc ccacactggc cttaaacact gacctcgaac tcatggtgat | 48060 |
| tctcctgcct aaacttctca aataccatga ttacaagagt gacacaccat gctgggagtc | 48120 |
| ataatcttaa gttaaaagt gagggactgg tcagtttact gtgctaggtt gacattgtat | 48180 |
| agaaatgaac agccatgttg gtctggaaat gttcctagtt ttcatttgta caaggatatg | 48240 |
| cagtgtgtga ataggggaga gtcttaccta tgtgggtttg atcacagcaa ttaataaaat | 48300 |
| atgctctaaa taatgaaaaa agccagtaac tagtagtgtt tctgaatcct cactaaagct | 48360 |
| ttaatacatc ataaataata tatcactgca gattatgtct acatgttata catatcacat | 48420 |
| ttatagtaca atctgatctt tgtcacctac tgtaagcaca actgaaaaac aaattttctc | 48480 |
| atagctcaat attaagtcat tattatcccc ataataagta attattatcc ccataatgaa | 48540 |
| actatctatt gagggagtca gaatctgaga tagttaaata aatttaagca tgtattttta | 48600 |
| gtgtcaatgg taaaaattaa atgttcataa agcctgtatg actccttta aagtagtttt | 48660 |
| aatttatgt gtatacatat atgcatgttt tgccttcttg tatgtctgag taccacttgt | 48720 |
| atgtctggtg cctgaggagg ccagaacgta tcagatcccc tgaaactggt attacagttt | 48780 |

```
tgagctacta tgtggctgtt gggaattgaa cctggatgct ctgaaagagc agccagtgct    48840
cttaatgact aggccatctc tccattttct taaaaaaaaa tttaaaacat ttactctaag    48900
atttactttt atgtaggtgc gtgtgtgaat gtgtatggtt tatgcattgg ggtggggagg    48960
atggattagc acagtcacag aagactagag gagggtctct actattgctt tctgtcttct    49020
acccttgaga cagggtctct cactaaacct gaaactcacc tttgcagctg gggtagctgg    49080
tcagaaagat cctggaatct gtctttctcc ctggccctaa tgcttgagtt acaggcccat    49140
gtgaccatac ctgtcgtttt actggggttc tacagagtca acccaagtc ctcacgcttg     49200 catagccagc gattttaccg actgagacat ttatctgccc caattcataa ttcttctctg    49260
cttccattaa taatcccatc tatgtcccct tcatacatat ttctgaaata gacaaaatga    49320
atacaagtta gacatcgagt ctgattaatc ttcaacttct ttgataacca ggtattgatt    49380
tctgactttt gaagatggat gaaggcacag aagtctccac tgatggaaat tccctgatca    49440
aagctgtcca tcagagccgg cttcgcctca caagactttt gctcgaaggt ggtgcttaca    49500
tcaacgagag caatgaccgt ggcgaaacac ctttaatgat tgcttgtaag accaaacaca    49560
ttgaccagca gagcgttggt agagccaaga tggttaaata ccttctagag aacagtgctg    49620
accccaacat ccaggacaaa tctgggaaaa gcgctctgat gcacgcatgc ttggaaagag    49680
cgggcccgga agtggtttcc ttgctgctca agagtggggc tgacctcagc ttgcaggacc    49740
attctggcta ctcagctctg gtgtatgcta taaatgcaga agacagagat accctcaaag    49800
tcctccttag tgcttgccag gcgaaaggaa aagaggtcat tatcataacc acagcaaagt    49860
caccctctgg gaggcatacc acccagcagt acctcaacat gcctcccgca gacatggatg    49920
agagccatcc gccagccacg ccttcagaaa ttgacatcaa gacagcctcc ttgccactct    49980
catgttcttc agagacggac c                                              50001
```

<210> SEQ ID NO 3
<211> LENGTH: 50000
<212> TYPE: DNA
<213> ORGANISM: Cricetulus griseus
<220> FEATURE:
<221> NAME/KEY: modified_base
<222> LOCATION: (13508)..(13531)
<223> OTHER INFORMATION: a, c, t, g, unknown or other
<220> FEATURE:
<221> NAME/KEY: modified_base
<222> LOCATION: (21446)..(21479)
<223> OTHER INFORMATION: a, c, t, g, unknown or other

<400> SEQUENCE: 3

```
gggctcaggc atttatcgtt cagagattga ctgagctgta aagatggaaa gacaaacttt      60
tttttttttt gattgagtcg gggtttctct atgtaacagc cctggctgtc caggaactca     120
ctctgtagac caggctggcc ttgaactcac agagatctgc ctgcccctgc ctgtcgaatg     180
ttgggattaa aggtgtgagc caccaccgcc ccgctgacaa actagacttt tagaatgtat     240
tatgagataa ggttttgtta tgttgcccag gctggactca gatctgtagc aatctatctg     300
ctccagactc ctgagtgctg ggatatacag acctgagtta cctgtacagc tttctaatca     360
tcccccgctc ccccagagac agggtttctc tttattgttt tggagcctgt cctggcactg     420
gcactcactc tgtagaccag gttggcctcg aactcacaga gatccacctg tctctgcctc     480
ctgagtgccg agattaaagg tgtgcaccac caacaccccta cttttctaatt cttaaagcaa    540 ggctcccaac tcctcccttg tgtgtaatca acaaggttct tagaccctgt ctgcagtgtg     600
```

```
gattcccact aataagacag tggcggcaca gtgctgtgtg cagagcaag cgtccatcta       660 gttcctattg tcattctatg atttgctctt ctgggagcct tgtcattcag caagttcctg       720
ggcttgtctt gggattgcaa tgtgcctcag cttggctagt tcctctgcgg cagaagcagt       780
gtttgaactc agtgggcact cagtcactac atctaacttg tttgagggct ctctgcattt       840
gctttccaat taaggtttag gatgactcct ccctgtgact cttatcatcc tgcctattaa       900
tgctaaatta gagaggcatt caagataact gccgaagatc taataaataa atgggggtggg     960 tgggtaggac tataaaccag tttatagcat gcaagaaagc tctgagcacc acattcaaaa      1020
ataaagtgct gtgagcctgg tggtggtggc tcacaccctg atcccagaac tcaagaagta      1080
gacagaaggc tcagattcaa gattcaagtt cttccactat acagccaatt tgaagtcagc      1140
ccagactaca tgagaccctg tctcaactaa gcaaatgaaa gcaaactggg gtccaaatag      1200
gcactattcg atgttttgat gcaagtttgt gactgaggag tggaggtggc aaatgaagac      1260 tttttcttc ctcttcttct tcctcctggg tcccgttttt tttagggtgt tcttaggata       1320
tgtatgtctc attggcacta ctaagaagtg tggggtctag gaacttcct gttatgtata       1380 caagctaatc ttcaaacaat tgtgtgggct gttttggtaa ctactcaaat aatgctatag      1440
aaaattgtac aatatattgg ggaaggaagg gagttttaca caggagtcaa catgactctt      1500
gtctctggaa agcaacttgt gatccaatga ggagctaaat ttagagacac aattcaggaa      1560
gagaatccaa tcagagcttc cttgtaaaac aactcacctt cacaaacaag ttcattccta      1620
atcgaattta aggtctagaa actgccaacc tattaatgtt tctataaata cacttggggt      1680
caactacgta gccaaggaaa tctttaataa attgaacaca aattgtcagg ggaaggttat      1740
tgctgggact cctggaagca tgtataagca gggtaggggt gacataggg tgggggcag       1800 ttaactcaca gatattagtc tcagatatta atggcttgtg tgtgagctgt ctgccacact      1860
taatgtcagt caccttgccc ggaactattt ttctctctga ttccaaatgt agctattggt      1920
ctattaaatg attaacttcc acagaaactg ataatatcct tatggaatct gactgtggta     1980
agcctgtaca cccccgcccc aatttccttc tagatttaga attccattcc atgagccatc      2040
acacccacgc tgaaaaaaga aaacctgttg aatcaaattt gtgttttgga gggtaagagc      2100 caccccttcca atttataagg ctgtctattt cttttggggg ggggaaatga accagtatct    2160
tctattagta aaaggagtgt ttgagcatgg gcactacaac ccacttcttt cagggagatt     2220 cattttctc tgagaactca gcctctctgt gctggtgcca caggaattct taaactcttt       2280
caactctcca attaaccaga gagcaaaccc agcactttcc atctatgaga aatctacacc      2340
actcatggaa tcattgtgtg ccctctctca ctgcctaaca ggggtaccct tgccaaagaa      2400
aagcaactta atgccaaaaa ggtgcatcac ctggcactgc ttccgaggat gggcaatgtg     2460
caagcacttt gttcagtggc tctgccttgg ggtctcttga ggggcggcag gttacctggg    2520
gtgggggcgc acactctctg aaggtgggct gcgttcagtt tcctgcttca ggggctcctt      2580
catagtaccg ccccctgatg agtttctgct cagactggaa ggtgtcaggt cccaaagaaa      2640
cctgggacaa ggctcactca gtacctgtcg cttctcccag cacgtctcac cccacccta      2700 ccctaaactt ctctagccca gaggctgggc tccccctttc tctttcctac ataaccctgc      2760
cattttagct gtgagctctc tccgtcttta gctcctctac tgttcttttta tcctctcttt    2820 tctctctcct cttcttctct caccccccacc cccacccccca tctctccccc catggtctgg    2880
ttcagtctgg acccttcag atgcctctgt ctgaactctc cctcatatct caataaaacc      2940
cttctcttca gccacgcctt ggagaggtca taggctcatt ttcgttcaga aggcctatca     3000
```

```
aagaatctgt gggcttatct ttacattcac aataggcagc ttggccctga gaccacagtc    3060
caggttaaag tgttaccttg gaaagaaagt cttttattca aggtgtctgg tttcttttct    3120 tgttttgtt tttgttttg gagacagggt ttctctgtat tattttggag gctgtcctgg    3180
aactcgctct gtagaccagg ctggccttga actcacagag atccgcctgc ctctacctcc    3240
tgagtgctgg gattaaaggc gtgagccacc aacgcccggc tcaagtgtct ggtttctttt    3300
gatgtcttta gtttctttaa tcccataatt cctttaatta taccctcttg tctgtcggag    3360
aatgacatca aggatatcca gttcaaggtt cctatgtag ttcagtcata gagtgcttgc    3420
ccagctgcca gactctgtca gatgcccagc accacacaca tacaaagcat tccagctct    3480 gtgtctgtgt caattactcc tgtctgcttc tccatcccca gacaccagga gggcccacaa    3540
gaagcttgga gcaggaaga ataaagagac aatatccata gacacacaaa acctccaaag    3600
tacttatgca ttgaggaatt acagcttaca aatccagtca cagtatctat attcatgtta    3660
gcctgatttc aatccccag ctacatattc ttccatgagc tagctccttt cctattcaag    3720
actcccttga taatagttgt tatcagactt taccccctatt aaaatatttg gaccgtttga    3780
gagcaatagc tcacctctat aatctagaac ccaggaagtt aaaacaagat gtttgctgca    3840
agtttgatgc cagcctgggc tacatagcaa tttccagaac atcctgagct acagggcaaa    3900
attctatctt aaaaacaaa aagtagacag atcaggtgtt tcaccttgtt tcaaaaaatg    3960 caaaaatat ttttaattg tagaaatata tacgctaatt cctttggtac cctaggccaa    4020
gtgactagat gggttagtct tccttctggt cctcacagaa gaaagttaag ttctcagcag    4080
gaataataaa aaatattaaa aaaaaaaaca agctgcaaaa ttctgttgtg gttctgccaa    4140
agtgttctca ggagtgaggg catactggga tttagtcaag cagatatttc tgtttgaata    4200
actaggatct gggagccatg ggacaccacc cccacccata agggctactg aaaaccaccc    4260
ctggaaatct gtaaatattg ctaaggctct accctttgc tcagagaaca accacccaca    4320
aggatagggg ataagttagt tctgtagtag agtgcttgct tagcacacag aaagtctttc    4380
tctctctgtc tttctctctg tctctgtctc tgtctctctc tctctctctc tctcacacac    4440
acacacacac acaaacaaac acatgagtgc acaagaaact tctaggtgct actaaactaa    4500
tgtaaaatca tgcaaagttc atagagaatt caacagctag tgacaggatg acccgaacac    4560
aagattctgc cctagtcctt gtattctgta gtccccagtt tctctttact gccacagtct    4620
cctatctctg acagcctccc tctttgcaga tctggcagtt tctgggcctg gaactgcttt    4680
ggtagaatgt ctgtacagca tgcactaggc actgggtttg atccccagca ctgcataaat    4740
caactttgat gtcacaccta aatttcagc acttggcagg gatcgaagca ggaggatcag    4800
aggtgaatca aggccagcct gggctacttg aaaccctggg gagagggata gaagaagggg    4860 gagggggag ggagaagaaa ggaaggaggg ggagggaaga ggagaggaag agaggaggga    4920
gagggaggga aacagggagg gaggaagaga aggagggaga gagggaggag ggagggagag    4980
actagtgtaa gcagaacctg taagttctct cctcagcctc aacacacccc agctccctgc    5040
tgtctcccgg tccagggctt cagggcctgg caggacaggc agcaggttgt tttgctctca    5100
taaagccatg ttacataact aactaatgtt ttgagcagtg gagctgagcc aatctaggtc    5160
acatcaagag ggaatgggga aagaggatga tcacggaagt ggtgagagga agggaaacaa    5220
gaagggagga ataaaaaaa gaggcgagag tggaaatggg gtgcgattat ttaatatctg    5280
ctgcctgttc atagttcctg gtccttaggg acagcatata ttatcctgaa aagtcctctc    5340
```

```
tctattttat ctaggcattc tgtcatccta tagcccccac tctggatggc tgaactctgt    5400
gccagcagcc tgcaggtatc accccttatt ggagtgaggt ctattcctta ttggaagcag    5460
tggcaggctg gtaggaaaca acaggcctg gtgttgtgga atgctgtcct cccagcatga    5520
ccatcattag accttatgga agcagagcga gggggggcatt gtcctcctcc ccaggctcct    5580
gcaagcctac tcagctcaac tggttccccg ggccagactt aggtgcaaga gttgctttgg    5640
tttgttattg gtggcctgtg tagctgagta gacacatgct cacctacatg atatatgatg    5700
gcttgcaacc ttctaaaagt tcagtttcag gagatccaga accctctttt gccctccaag    5760
gacaccagac acccatgtgg tacccatacg tacatgcggg caaaacactt gtgcatataa    5820
aataaaaaga gatggctccg tggctaagaa tgctccctac ctccagctca cccacatctt    5880
cacaactgac tgtgaatcca tccatggttc tcttctgacc tcggagggca cctgtgccca    5940
tggggcatac acatacacat acacaaaaca agtatgtaaa taaataaata tttaaaattg    6000
gggctggaga tggcttagtg gttgagagca ctggctgatc ctccagaggt ccagagttca    6060
attcccagca cctacatggt ggctcccaat cacctaaagt gggacctgat gtcctcttct    6120
gacataaggt catacatgca gatagaggac tcaaatgcat aaaataaata aataaatctt    6180
tagaaaataa gtacataata aataaatatt taaaatgacc caaattaaga aaaaaatgaa    6240
gccaggcagt ggtggtacac tcagaaggca gaggcaggca gatctctgag tttgagacca    6300
gcagttccag gacagccaga gttacacaga gaaactctgt ctcaaaaaaa aaaagaaaa     6360 aaaacagag aagaagaga ggagaaaaac aagaacaaaa aataacaaaa caaaaacatg      6420 gctttcccctt catggcatct gcttcatctg cctatttggt aatgatcagg gcactacaca    6480
cccagtgctt cataccctgg ccatgtttct gttcttggtg tcaccaccaa gtttactaaa    6540
gatggttcca gagtgacatt agcagcccca caccccaatt gcagctagca gttgaggaga    6600
tttctggctt tttgtctaag aggaaggttc tttggctagg agatatactg agaaggacta    6660
ggaaaagggg tgtctaagaa acttggagag cacattttc aagtcagaaa gaacatagac      6720
atattctggg ggtgggggta gtaagataat ggaccctcct aagggaagga ttgtggggtt    6780
tgcctgaagg ggctgaagca gaccactgag caggccagac caccagcagc ttttgagagg    6840
tgggaacact gcagctgaag tcacttgtca ccttcccagg tagttcttac ttccagctct    6900
ggcagggcta gatagcctag gaactcccag ataggagttc tagttcttct tctcccaagc    6960
tgacagaacg tgagctcaga gtctagggac actccaggtt aaggacgggg ccattcttga    7020
ttgtcagcac agatagattt taattagaga gcaatgacat gacagataaa cagcccctta    7080
tctaaagggg tacatcccaa gaccctggag gactcttgaa aacccagata ggagccagcc    7140
acggaagcat atacctttaa tcctaagatt tgggaggctg aggtaggagg atctctgtga    7200
gtttgaggcc agtcttgtct acaaagtgaa ttttgggaca gctacacaga gaaaccctgt    7260
aagaaaaaaa aaaaaagaa agaaaggaag gaaggaagga aggaaggaag gaaggaaggg    7320
aaaggaagaa aaagataaag gaagaaaatc caaataggaa agaatcccat atataccata    7380
tttttcttaa acatacatag gtttattcat tctctctgtg tctgtgtgtc tgtgtgtctg    7440
tgtgtctgtg tgtctgtgtc tgtctgtctg tctgtctgtc tgtctctctc tctctctctc    7500
tctttctctc cctctctctc tctttcttgt ctcataaatc tcaacactca gggacccaga    7560
agatatccca gtggttaaga atacacactg ctcttgcaga cctaaactca gttccttgtc    7620
cctacttggg gcagctcaca accacacctg taagtctagc tccagggaat ccacaccttc    7680
tggcctgtgc aggcacctgt gtgaaggagc acatatcctt ccccataatt aaaaaacaat    7740
```

```
cattgaaaaa taaaactcaa ccccctcccc cgggactcaa accagaggta gtctccctgc    7800
cgtaggcgct caaaaactgg actttcaggt gtgagcctct aggccaggct gcttttctta    7860
actggctacc gtgctcttgc ctgaaacttc cagcttgaga cctcatagta aaagaacat     7920 acacgtcttc tgtctgtact attttacaga cggctgacat gttcatacca cgtattttag    7980
caatttcagc acttggtata ttttctgtca ttctcaaata actttcacct tgccacttag    8040
ggcagtccaa ggctcctctt agatatatcc aaattatcag ccaccacttc tgcctttact    8100
aagtaagaca gggtacttaa catggagtac ttaacacaag cactgtgatc tgaaggtgga    8160
gactgcttgc tactcagtca cagcttagca ttgctagaac aaatcctgaa caaagggtaa    8220
ttcatgaccc aggcagggca gaggcggatg gctgttcttg ctcctcagaa accctgtgt     8280 ataatttcaa gcttaggagt tgtttgtctt tggatggaga gggtcagacc tagggcttca    8340
ctcacactag gcaagcaccg caggtctacc ttcgaagaga agaattttca cttagcgttt    8400
tcagatatag gtcaacctca gctggctgaa actttgacta agtgagcaac tgtgagggtg    8460
gggaacacat gcatgcattt cttcatgtta taacatctat ttatacataa acatatcata    8520
taaatatatt ctattgcata taaatataca taaatgcaca ctcatgtata gatatcaatc    8580
acataattta tgcttttatt catagattat ctctgggagg tgtacaatta ctgacaatac    8640
ctgcacatga tagtacacgt tgttctagtt aggtttcttt tgctgtgaca acaccacaa     8700 ccaaaagcaa cttgcagagg gaagggttta tttcagctta cagttgtatt cattatgaag    8760
agttgggaag tcaggacagg aacctggagg caggaactga agcagaaacc atggaataat    8820
gctgcttact ggtttacccca ccatgactca acctgctttc ttatatcacc aggactgctt   8880
gcccagggat agaaccacac atggggactg tacctcccac aacaatcatt gatcaagaaa    8940
tgccctagag tcaggatgg tggcaaatgc ttttaatccc agcactcggg aggcagaacc     9000
aggccttgac tgtgaggtca aggccaggct ggtctacaga ttgagttcca ggacagccag    9060
ggctactcag agaaaccatg tctcatggaa aagaaaagga ggaggaggag aaaggagaag    9120
gaaaaagagg aggaggagga ggaggaggag gaggaggagg aggaggaaag aagaagaaga    9180
agaagaagaa gaagaagaag aagaagaaga agaagtagaa gaagaagtgt ccactggaca    9240
atctgatggt ggcgtttccc aattgaagtt ccccttccaa gataactcca ggatgtgtca    9300
agcagacaaa aacaagaacc aagacacatg tttataatcc caacactggg gaagtggaat    9360
aagaggtttg gcagtttaag gccattttca gctacatagg gagttccaga ctatcctggc    9420
tacatgagac cctgtctcaa aacaccaaaa tgcaaggaaa aaacaaaaag caaataatg     9480 agtacaaata gcagtgacat tctggggaga cagcctggag gggggattg cttattatct     9540 ctccctaccg tttggagttt ttaaaatcat gaatctaacc ccagaaaaaa aagcattgag    9600
attctgggac actcgggtgg tagagaagat catctgatcc tgtcaccttt cgggtacgtc    9660
actttattaa tctctctgag attcagtttc atcacctctg aagtggtttg tgtcgacgta    9720
cagtcctcag gactaagtaa ggccacttgg tggctgtgcc aaagcactgt gtcagggaca    9780
cggcagatgt ctgacacatc ttgttagatt cctttttctgt cctccgctcc cctaccccag   9840
aggtgggtac agccccatgg cacctcatct ttaatggctt gggtttcttt tctccagcca    9900
ggaaagttgt cgctttggtg acagctattt taagtcaact gacctttcct gcaaatgatc    9960
cagatgcctc tatcttaggc tggtgatgac gaagatggcc tatgacgggg ttcctggggg   10020
tgtgttggga ggtggggcag gggtggggcc cggcatttgt cagacccata tgatcttctg   10080
```

```
gctcccgggc tctgcagatt tctcctgctg gagatgccta cctgccagca atcttggaga    10140
agacagaaat agcagctttg ggttccaggt cccctcctcc ctttggccca atgtagctag    10200
agctttggtt tcctgctgct gtcttggtgc ctggagccct ctctggatgg tcatggagtc    10260
ttgtcagaga agcaactttg ggctggcaga cagtcattcc agaagacatg atctggaaaa    10320
actgcttcat cgtttccttc agaggcactg tcccgagccc atttccttgt ctggttcctg    10380
aaatctcagg gatgccatca gaagaaggtg ttcttgtgtt tactttggac atggttttct    10440
gtagtgcaga ctgcccttaa actctacgta gctgaaaatg accttggtct ccagacctct    10500
tgatctgtca gcatccctgg gaaatccagg gttctgtaat cctcccctct caccttgact    10560
tactgtacca gcatcaaaca tcctaaacaa atccagtgtt tagccaaata cagcggtgca    10620
tgtctgtaat cccagccacc tgggaagccg aggcagaagg attaagggag ctggaggcca    10680
gtctgtgcaa tttagcagga ctgtctcaaa acaaaattta atggttaggg gtgggcatgt    10740
catttatttg actcttatca catgaacaca cctgtaatct catcacgaaa cgacaaggca    10800
ggaaaatcaa aagttcaaag tcatctttgg ctacatagca agttctaacc tgacctaggg    10860
tatgtaagac cttgtctcaa aagcaaacaa acaaacccca aataacaaca acaacaaaac    10920
aaaaagcaaa caaggagagg gtgtgcagct agggatataa ttcaatgggt gagggcttac    10980
ctcacatgca cgaggccttg gtttcaactt ccagttgaaa tgaagtttag tggtagagtt    11040
ctgtgcaagg ctgtagtttc agctctccat actgcaaact ggaaagaaca acagtgacaa    11100
acagaaacaa aaaccccca caaacaatgt gctttctcac tcaataaaac cacctcttta    11160
catacaacta caactgctaa gaaagttctt cagtgttcta gagcctgagc acctcaaatg    11220
gtttccataa agctgtatgc aaacactgat aagccacgag aagcaactgt acaaagcacc    11280
ctttgatttt catagtttat ctacacaagg attctaggaa agtgtgctag gaaaatttta    11340
tgtatcagcc ttgcgggttt gtccaatagt tttagatttt gccagtgaag attttccttt    11400
ctttattttt tacatgggaa ggaagtttaa ttggggaag ggacgggagt gggctttatt    11460
tttatttttt aatgagacta gcatttgcat tggtggacat tgaaggaaac agtttcccct    11520
ccctaatgtg tgtgggcctc acctaactca ttgaaagtct tagataaaac taagctgagt    11580
gagtgagttg gcccatacct gtagatggaa ggaaaagggt cttgagtttt ggtttatcct    11640
agagagaact tgatccccca aacaccaaac tttcaaacca aacccagcc tcctcagtgt    11700 gaagggatgc tgttacatga ccacctatgg actcagacaa cctctcttcc ctgagtctgc    11760
tggcttactc atcagagtct gggctcacga agccgccaca catatatgag cctcgttctc    11820
cccactcttc tcttgtggca ctgaggttca aaccaaggac ctcgcacatg atagcaaata    11880
ctgtactgaa ccatagagcc agcccttgtc agtttcttaa cacaaacata tagatgtata    11940
tgtatatgaa tatttccatg ctaccaattc cattttctca gagaaccaaa gaatacacca    12000
agtagtcaca cttgaaattc tgttctgaga ttgaataaaa cctgatcaaa tgtgaattcg    12060
gtcccttctc ccccatccct gacgccacca cgttgctata cagaccaggc acaaactctt    12120
ctccttgtga atgtgtgtaa cacatgttac cactgtgctt ggcttttgta gttagaaggt    12180
tggttgatat ttaaaaaaaa actttaatat ttagtcatta cttttagta aagatttgcc    12240 ttgctttat tttattcatg tgcatgtgtg tgtatctgtg tgagtgtatg ccacgtgtgt    12300
ttgggtgcct ctggagattg gaaaagaatg tcaaatccc aggacctgga gttccaggca    12360
gttgtaaact tcccaatgtg ggtaattata atgaacttgg atcctctaaa agagcagaac    12420
tcactcttaa ctgatgagtt atccttctac ccccaaattt atttgttttg tttatttgtt    12480
```

```
tatttatttg agagggtctc actgtgtagc tctgacagta ttagaattta ctatgtagac    12540
cagacttgat aaatgtctaa ccctagaaaa aaatagtttt gttttgattt tatgtctgtg    12600
ccatccactc cttgaacata tatttggtat ctgtgaagcc agtgaaggct gttggttccc    12660
ttaggactgg agttacagat ggctctgagc taccatgtgc atgctgggaa acaaactcag   12720
gtcctttgga agagcaaaaa atgtcctttg atggtggtgg tttgaatgag aattgcccta    12780
tcgagcataa aaacttggca gctttggcta catggttctg gattaagagt caagaaggat    12840
acaagaaagc ggttgtggaa tcatccccca tggttaagga aaaccaccaa agccaggctt    12900
gtggcagggg agttcctgca tggaggccaa gagaagccac tatgtcaagc tgtgaaggtg    12960
aagcctggat tgtgttggag acccaagcta ctggagatgt aagagatgtg agataatgcc    13020
caggagagct gcagacaggg catggaatca ggccaagcga gagaagtgtg ttgcagtcag    13080
cagaactggg agggaagagt catctaagtc ctttgtcatc agacatagag atacaggatc    13140
tgaaatttgc tctgctgggt tttggtcttg atttggccca gtacttccta actatgtccc    13200
cttttctccc ttttagaata ctaatttata ttctgtgcca ttgccggtgg atcaggatgg    13260
ttctcagata ctgttttagt tccatgcctg tctacttccc gtcatgacag tcatgcacta    13320
acactctaaa actgtaagca agctcccaat gaaatgtttt catttataga ggtgccttga    13380
tcatgctgtc tcttcacagc aatacaacag tgattaagtc agctgctgag caatctctct    13440
ggccccagaa gtatgcatgt gtgcaattgt gtgtgtgtgt gtgtgtgtgt gtgtgtgtgt    13500
gtgtgtgnnn nnnnnnnnn nnnnnnnnnn naggaaatgt cattctgtaa atatgtttat     13560
cttattggtt gatgaataaa acactgttgg ccaatagggc aacaaaatag gtggggccag    13620
gatataagga ggattttggg aagtgtaggc agagggaat tgtcatatga tcccaggaag     13680
agacatagat gggcagaaac tgcctctagc taaccataga ggtctggagg tctgtacaga    13740
caggcaggaa gtgatgtagc tggaagaatc agaatataag caggaacaaa caggaaatcg    13800
agctcttctt ctctctccac ttcagagatg ctgaacagtt gagatgcagg atgccagaag    13860
agtaagaggt ccctggacct ttctccagta agataagacc atgtggaaat agattgatag    13920
aaatgggtta gagattaagt cagagctagc caataagaag ccgtagatat tggccaaccg    13980
tttcataatt aatatagcat ctgtgtattt atttggggga cctggtagac cagaaaactc    14040
gtgttagaga catcttatca aagttgaaaa aagaaaaaat gtgataaagt taggaaaaaa    14100
tatagtaaat gttaaaagct aaattctaaa actacaactt atttatcatt tcctaaatgt    14160 ttaaaatat tattttataa tgaagatact taaaattcat ttctctgtct tttgagacag      14220
ggtctcagtg tcctggaact cattatatac agcaggctgg cttggaactc acagagatcc    14280
acctgcctct gtcctaaa tgctgggatt aaggtgtgt gccaccaagc tcaattaaa        14340 atgcgtttct ttttctttct ttcttcctgt ctttcatttt tttgtttgtt tagatttttt    14400
tttttagaca gggtttctct gttagcatta gttgtactgg aactcactct gtagaccagg    14460
ctggccatga actgagagat ctgcctgcct ctgccttctg agtgctagga ttaaaggcat    14520
gcaccaccac tgccaggctt aaaatgtatt tctttttta atttagaaat ttattctgtt    14580
taatccacac gctttatata gctttagtta agaaataaaa taaatgaaa cagtgaaacc      14640 aagagactat gtccaagtcc aggtcctccc agcctgccaa tgccaagagc tctttagttc    14700
tgtgtaccaa ttgaaagagt aagaaaaaaa tatggatggg aaccacacag tttcataaaa    14760
cagatttatg gaactgaagg gtccttgctg agtctagcaa attgcctta caaaagagaa     14820
```

```
agaaaaaagg gggaggtaga aaaacaaaac aaatcaaccc aaagaggaca aaatcccaga   14880
gttctaaatt gacttaggaa cctgtcacac tgggacagaa gcttcagcat ccatgagctg   14940
tgcctcccct gctctctaga gctgggatct cgaggtgtca gcagagaccc cacaggtaac   15000
aggagcaaaa acactcactc agacctttgt ggtacttcaa cagtggtctc acttctgggc   15060
aagcttacaa acctatacaa agttgaaggt gtactttaca tgagtgctaa acttcaagag   15120
gaaggaagaa aaaagggag gtggagggga cagagagaga gagaaaaaaa caaaacaaaa   15180
caaaaacaac cacctcagga gaggcaaggg catttaaagg aaccacaaga atgccaacga   15240
tattaaaatg tatttcttaa tagtaaattt tatgggaaaa gagagtctcc tcttcctcca   15300
agtaggctag gtaagtacct tgccactgag ctctatctat acccttcaaa gtggacaaaa   15360
tgacaaagat agttcatctc ccccaaaggc cctgttgggg tgctgattgt cacatctggt   15420
gagatttctg tttttgtttt tatttcaaga cagggcctct ctacatagat agtcctggct   15480
gccctggaac tcactctgta gaccaggctg gcctggaact catagaccca cttgcttctg   15540
tctcccaagt gctggtgcta aaggtgtgca ctgccactct ttttaagtaa ctatgagttt   15600
caaaacaaat taaagagcac tgttaaagtg gcttgttgtg taagcctagc ttcaagtcaa   15660
aggcccgagg ctcccctacc aaccagctgc tatcacctag acactgtctg tagatcttgc   15720
actgactcaa aactgtggcc taaggtcaaa ataatggtct tcctggattc tgatgtgagt   15780
gagattgtgt aggagggctg gccgctggcc tggcttgagt cactctcagc tggtttcatc   15840
ccattcctgc aactctgtgt aagaggtgga tgatccttgc ttaactgatg aagaaaccaa   15900
agctgtagaa aggatcattt gcttaactct tcacagatgg caagaggcag agtcaggatt   15960
ggcagagtca cttctgccaa cttcacccctc ctgctaactc caccctcctg ctaactccac   16020
cctcttgctt atacttgaca gtggaggaaa agccactgag ggaattaaaa gttgttactg   16080
gtaatggtca ggaaaaaagc tgaacaaagg agattagatt cagggatctt tttctgaaaa   16140
gaaagaaaga aaggggggact atagtctaga aatgctgaga taaaagggtg gattatcata   16200
tctactctca aactaaagaa gcaactacta gtctcaaata ctttatattg gtatggattt   16260
ttgtgtattg gtacaaattt aaggttattt ttgttatact gtatatatgt ttttctttct   16320
tgtttaaggt attgtacctg tatagcttat ttaaaaatgc aatgtaaaca tatagtcctt   16380
gaaaactatt taagataata aagaaataca ggttaatagt catctatagc aatcaaactt   16440
atagtcatgt taggtatgtt ttcaagggca tacagaaata aatttgagat agataggtca   16500
tcttcaaaca ctccagagat ctacagaaaa tggcatttat aaaatgtttt aatgacataa   16560 gattttcat gatagtgaga aatgtctact cttggcagca ccaatttact tcaaaaatgg   16620
acaatgggca ttgaagaaac tccatgtgga ttttgctttc tttgtggcaa aaatctagct   16680
atctgggcaa gaaacttccc ttaccttgac tgctgtccta actggacaag caggacataa   16740
aagaaattga ctgctgaact ttgccaagat agtatacatt agtctttcaa aaatccctgc   16800
tttacaaaaa agtctatcag atattctaag cttctaggcc aaagatggat gcttcaatgt   16860
taacagagga atcttctgtg actgatgttt ctgtcatttc tatagttttg aaaattgctt   16920
gctctgttct tccctgtttg ctcaggtagt attatttcct tcttgagtgt ctaatggagt   16980
taaagactag atagttatag ctacagttttt ccttgtaacc aaattcagaa aagaaactcc   17040
caaaagaggt gtaaaagtat gaggctgaga aatataaaaa cttaaattta tctaagaaaa   17100
tgttttgtta tctaaaaaaa aataattttg ggttagtaat acaagttagg atagaaaatg   17160
aattaggtac aaaactttgg actcatcaag aaaaaataga taatggagta ttttctctga   17220
```

```
atttgccaaa tacaaataga ctgggtattg taaatgtaat tcttacttga taattgttct    17280
tattgtttat agtttattat gttagagtca aaacctttct tttttattta gacaaaaagg    17340
gggaatgtag aatatttctt tacactgtgt gaagatgtat cactgtgatt ggtttaataa    17400
agagctgaat agccaatagt taggcaggaa gaggttaggt gagacttctg ggaacagaag    17460
tctcagggaa ggaaacaggc taggtcacca gctaaatgaa gaggaaatag gacactcagg    17520
aggagaggta acagccacaa gccaagtggt ggaatataga tgaatggaaa tgggttaatt    17580
taagtcatag gagctagtta gaaacaagcc tgagctaaag ctgagctgtc ataactaaaa    17640
gtggagcttt cataattagt aagtctctgt gtcatgattt gggggctgac ggcccaaaaa    17700
agcctgctac ccaagttctt ttcaattttc aagttctagg attctggcct tttattggaa    17760
aacactgtca agtttctata gaggtctgac tccacagtgt tgcctgtgca atgaaattta    17820
tttaatttat tccgaggcct tgtgcactct ggataatcac tgtaccactt aatctatatt    17880
cccatccttc attataattt aaaatggtct tattaatctg gtcacttggc ttttttttt    17940 tttttttct gagacaggat ttctctgtgt agccttggcc atcctagaac ttgctctgta    18000
gaccagcctg gcctggaact cacagagatc cacctgcctc ccctccagag ttctgggatt    18060
aaaggcgtgt gccaccacct cccagtgagt ttatgtcttt gcaaattata catggtttca    18120 gtttttttt ctgtttgtaa gtcactttat ttcaaatgta aagtttaaaa caagaagcaa    18180
attactatga attttgtta acagtcattt tccttaacta ataagtttta aattttcatt    18240
aatatgtttt gatcatattt tttccatgcc ccaacacctc caaaatctcc ccactcattc    18300
agttctttct ctatctcaaa aaatgaaaaa tccaagcaaa caaccattag acaaaaaata    18360 acaaacaaa acaaagcaaa gcaaataaaa agcacacggg ctggagagat ggctcagagg    18420
ttaagagcac cgactgctct tccagaggtc ctgagttcaa ttcccagcaa ccacatggtg    18480
gctcacaacc atctgtaatg agatctggtg ccctcttctg gtgtacagat atacatggaa    18540
gcagaatgtt gtatacataa taaataaata aaatctaaaa aaaaaaaaga aaaaagcaca    18600 caaaaaccc agagagtgtg tattgagttg gttaaccccct actcctctgg agtgtgattg    18660
atacagccag tgccgctatt ggagaacact gattgtcccct gtccttacag gtatcaattg    18720
tgtgtagctc cttggttagg aatggggctt tgtgtgcact tccccttttca gctttgtaaa    18780 gggtgtccga ttgaagttcg tatcttctgg gagagcataa aatcaaaaaa agataaatgg    18840
actccagtga aaaggagca agcggcacct atctttaagg tagagaggca gaggagtgtg    18900
gtgtggcctg tcacaaacac ccaattccca atcagctggc gtctaccagg ctgctttcac    18960
ttagatgaac cctgacctcc atgtctcctt aacattgcca ttgtttaact gttagtgagt    19020
ctgccctctg ttcactgaaa gactttcaga aggtggtgtc gcctgccttt aatcctagca    19080
ctcgggagtc agaagcaggt agatagagct ctgtgagttt gaggccaggc tggtctgcag    19140
agttccagga caggctacag agtgaaaccc agtctcacaa acaccgcctc caccacaaaa    19200 aaaaaggaa acaagataga gtgaacaaac ccagctacct agacatctat ctggtaaact    19260
gactcatccc aatcctccct gccctcccaa agagcttggc tggctcactt ccccaaatgc    19320
tcttcccctt taacatttaa ctagttcttg tctcttgtat ggtttccttt taactgtatc    19380
caccacccct accttgactt ttgtcctggt tggtttttaa ttgtaaactt gacacacaaa    19440
gtcacctggg aaaagggaac cttaattgaa gaattgtctt agattggcct gtgggtgtat    19500
ttatagggca ttgtcttgat tgccaattga ttcggggtgg ggagtgggag ggtagggtgg    19560
```

```
gggtgggagc agcccactat gggactcact ttccctaggc agatggctat attagaaagg    19620
tagctgagcc taagccagcg ggtgagccga gccagcaagt agcattcttc tatggtttct    19680
ttctttcttt ttcttttcct ttttcttttt cttttcttt ttcttttcct ctttcttttc    19740
ttttcttttt ttttttttct tcccgagaca gggtttcttt gtgtagcttt ggagcctatc    19800
ctggcactcg ctctggagac caggctggcc tcaaactcac agagatcctc ctgcctctgc    19860
ctcccgagtg ctgggattaa aggcatgcgt caccaacgcc cagctcttct gtggtttctg    19920
cttcagattt ctgctttgag ttcctgtctg acttccctca ataattgttt gtaacctagg    19980
agtgtaagac aaatgaaccc tttcatcccc aagtagctat ggatttagag tggtttatca    20040
cagccacaga gtgaaaccag aacaactttc tagtagcctc ttgttctact ccagctgctc    20100
ctctgactat tcctaaaagg tagttgggct cagggaacca catcccgaga gattcagccc    20160
atatgaaaat agctccattg tgttgaagaa atgtgaccct ccaggatttc aggcatcagg    20220
attccatgtt gaaaatgaaa acaattattt tcctctctct caagattcct ttagtcacct    20280 tccctttaccc cagttcctgg ctttccttct aaacaaatgt tcaggaggt tcaaacaaac    20340 agctgtgaag agcagcatcc catacccca ccttccgacc caacacttgc cagtgctata    20400
agtagactgg gatcatccct ggacactgtg ttaaattacc catgaccaac cttctagcaa    20460
gctctccttt tcaggatttt gttgtttgtt tgggtttgtt tgtttgtgac ttgatctcat    20520
gtaagctgac ctgaatttg cttaatagcc aaggatagac ttacaacctg tgatgctcca    20580
gcctctgact cctgagtacc agggattaca catgtgtggc atcacaatga aagattttag    20640
tttgctgaga gaaaaagttt ttaaagattt tagttcacag agagaataag tttcccacag    20700
gccttggtcc aggacaagga agttggtccc aacccgaggg cagacaaaca atcctttttg    20760
ggtcacacct ggctggccaa cagacaataa aggacttctc agggtacatt ctatggttga    20820
ccactctaac atgagatcat actttgtaat caatcacttt gtgccccttg cctgtatgct    20880
gatctgcggt tttttacagg ctcctatata aggagtctgt aacccttgct ggggtgtgca    20940
gcttccccga tattgctgac acccgaatga gcattcgttc aataaaccct cttgcttttg    21000
cagctcttgg tctggtttct gagtcttggg gcctccttgg gatcctgaga cccttaaggg    21060
tctgggggtc tttcaacact taactttcct gttttttaagt aggaagatct gaaatcccag    21120
attcctgact ccattgcaca ttttctgtat tagaggctgt agctctgtat agtgggttgt    21180
gtggcttaca catgctctga gctggagatt ctagggacac ttagggtaaa gtggagtgtc    21240 agccccttc cctgctagac tgaggccttt ctgttctttc ctaactggga ggctgtatag    21300
cacccaatgt gttcattaaa ctccatatgt tagcactgca tggaatctga cacacacaca    21360
cacacacaca caccctctac caccaccatc atcagcacca ccccatcag caccaccctc    21420 atcccccac ccccaccct gccccnnnnn nnnnnnnnn nnnnnnnnn nnnnnnnnc    21480 aactggaggg tagcattagc acccagatgc cattaatgtg ccaaatattt gcttgcttgc    21540
ttgcttgttt gttccagcat ccttagtgaa tgctcctgcc ctcctggtta aagatggctt    21600
tggcatctct tggcatcttt cttgtattct aggcctgaaa tagggatgaa tggtgaaggg    21660
caaggagctc aagtgtcact taccacctgc acttgtccct ttaagggggtt tccctagaag    21720 cagtctacat ttcattagcc agagctttgt cacctggcta cttgtgaagg aggtggtgaa    21780
gaagccttac ctttgactct gccacttgga gccaagtcag gattctctcc ctggaaagga    21840 aatgaagat taataccttg ttggttgtta gacctagccc attatgcgcc atgaggaaag    21900
agagacaaca gtgggtcact gattgatcag ggttacagga caaggagcct tgtttctcct    21960
```

```
aacagctctg agcggagaca gaagtggagt atataggcat aaaattcaca aacatttgct   22020
gccacgttac aggtacattt tttcaccagt cagaaatcaa agattaggga ctttgcttgt   22080
gtgttccatc actgtcaact gacatacacg gcaagccttt tagtccaacc aatcagaatc   22140
atttgttcct tctgttgtta ggagcagcca taatgattct aaagaactaa caatgcataa   22200
tgactatttt tgtagtttag ggatgaggta tgtcagccat tggacagttc tcagctcccc   22260
tagggcttgg gaacttgaac tttatttcat cctgcatgta atggagtctg aagtcaaaat   22320
ggcagtactt aggtcaaggt gctcgtgcct gctgccttca aggtggtttc ccattcccac   22380
cataccagag acttcctact gcatctccag tcaaggacac aaaacttttt aagtcctgac   22440
tgttgattca atctatatag ttaccagcat agaggctaag agtcacactg gcttgcaggg   22500
gacttctcta gcatatgtga agccccgttt gaatcctaaa cacaagagtc taagctttgg   22560
agtcagagac aagcatgttc aaatctgtac gtcaccaccc tatagacata gacaagtccc   22620
ttgggctcag ttttttcact acagagagta attgttattt cagattccta ggggttgtggt   22680 aattaaatag ttgaaagata tagcccatgg aacataaaaa aaactcaaaa ccaggcacag   22740
tggcacatgt ctttaatttc agcactcaag agacagaggc aagtggatct ctgtgagttt   22800
gaggccaggc tggtctatat agagagttcc aggtctacac agagaaacag gctcaaaacc   22860
aaagcaaaag caaaacctca actaatgttc ataaaattat gaaattgctg gtaccagtga   22920
catgactcat tggtaaagac acttgctagc aagtttaatg atctgagttt tatctccggg   22980
atctacaatg tagaagaaga aaaacaactc tcaagagttg tcctctgatt tccacttatg   23040
caaaatagca tgggaacaca cttaagcagg taggtaggta ggtagataga tagatagata   23100
gatagataga tagatagata atagacataa ttaagaacgt tcagttgcag cacagttcat   23160
actgaactgc atttggacac ctctgtgaaa agtcaggagc tctcctgtcc tcctggtgac   23220
atttaaacat tgaaggcaac tattttaact gtcagttata tacaaatcca ctggccttgt   23280
aaaattttaa aacataacag aggaggctaa agtcctgttt aacaaccctc tccttttacc   23340
atcccaggaa gccaaaattg ttcacaattt gttctcttcc ctcaggcctt ccatatttca   23400
aataccacat aaaacaccta tggaaaaaca tgaggtatta aaaatgtcac ttggaaatcc   23460
ttcttcaaac aagcttgttc tttctttttt cttttatgta cagtgaatgg aatccaggac   23520 cttttgcagat gctaggcgag tccttttacct cattcctctt tcgatttaaa acttttttctt   23580 gttttgtgga gacagggttt ctctgtgtag ccatagatgt cctagaacta gctctgtaga   23640
ctaggctggt ctcaaattca gaagccagtc tgcctctgcc tcgggagcgc taggattaaa   23700
ggtgtgggca gagtgctagg atgaaggta tgcacaccac cactcctggt tgattttaaa   23760
aagatgcttt ttaaaaaaaa tgatgtgtag gtagtggggg gagagacggt ttcatgccta   23820
agagcactga cagctcttct agaggactca ggttcaattc ccagcaccca catggcagct   23880
cataaccatc tgtaaccccg gtcccaggga atccaacacc ctcttctggt ctctgtgaat   23940
gacagatatg catgggatat acaaacatat acgcagacaa aacactgtat acattaaata   24000
agtacaaatt taaatatgt gtaggcatgt atgtctgcat gtgggtatgt gtacactgaa   24060
tgcaagttca cttggaggcc agagatatat agatcccctg gagttgcagt tacagatact   24120
tgcgagctgc tgtgagtgtg ctgggaacca aatcctctgg aacagcagca agtgctctca   24180
cctgctgagc catttcttca cccgcttctt tctacttttt attttgagac aaggtcttac   24240
taagttatat attcacttgg ggcttgaatt cattttgtca gcaggcagac cataaacttg   24300
```

```
ccttcctctt gcctcgggct cctgagtagc tgagacttca ccatgaggtc tggctttgat    24360
tacattttc tttgttttct ttttgggggt ggggctgatc atgaactcta aatagccaag     24420
gattgatagt gaagtccaga ttcccccacc tatcaccggg tggaattaca ggtgtgcact    24480
accacaccca atttggtttg atttttttt tttttttcag acaagctct ccttttatag      24540
ctctgactgg gttggaattt actatgtaga ctaggctagt gtcaaaatca cagagatctt    24600
cctgtccctg cttcctgagt actgggatta aaggcatgta ccaccacacc ttcgggtgtg    24660
gtgatgcaca gctttaatcc cagcactcag gcaggcgaat ctctctgagt ttgaggctag    24720
cctagtcttc agagtgagtt ccagaacagc caaggctaca cagagacact ttgtttcgaa    24780
aaacaaacaa aaacaaaaga ggctagcctg aaactcctga ttctaccagc acctcccaag    24840
ggctgggatg acaggttgtg gccccatgct ctctgccggg gcctctcttt tctttcttct    24900
gtttgaggta gaggcttact aggttggctg ggtgagttgt gaactcactc tgcagcccac    24960
acaggaactg atcttgtgat cctcctgcct cagtctccct agcagctagg attgcaggcc    25020
tgcaccatca ggcccatcgt acactgtttt ctgagtttga aaattgcctc tgttgttgac    25080
tataaggcat gctctcctcc taacattgtc cttggtgcct ctgccaccct ttgggactag    25140
agagaacaga tcttattcct atttcacatg ctgtgccaac ccagtaacaa actcagattc    25200
ctgcttccgc ccccaccacc cccatctaat tgttcagtgt ttctgtgaag ataaacacga    25260
tcatctttgt gaaagccact taagttcctt tcaaggttgg gatataagtt agagtgatag    25320
cttgttccca gggtggggag agcatgtgaa ttcccctctc gctcaagtag gctatactaa    25380
ttttcattta gatatttctg aggcaaagtc tcatgctggc catccacctg ccttagcttc    25440
tcaagtgctt ggattacagg catgagctac aatatctggc ttagtttcaa ggttgtgaaa    25500
attatactgt gttctgatga cctgagttca attccctgga cctgggtgat ggacggagag    25560
gacagacccc tgcagattgt cctttgacct ccctgtcact atgtgaacac tcgtgtacac    25620
acacacacac acacacacac acacacacta aatgaatgta ataaaatata aaaaggtgtt    25680
cactagttaa taagacatga gagaaaaagc ttaccatccc taatcaatgg ggaagcattg    25740
aatataagtg actgtggtca tggaaagcag tatagaggtt cctcaataaa ctggaatata    25800
gcagcatata cttgtaagcc tcccacaaca ggagaaaggt aaagaggggc ggccactctg    25860
gaatattatt aatatcctgt ttcataaaca agtaaataga acaaacccct caacaacaag    25920
aaccggtgtg ctggcacaca cctgcaatcc cagcatttgg gacttggagg cagcacaatt    25980
gaagttcgtt cttggtcatc ctcagctatg tatgaaatct gaagcctgcc tggcctacag    26040
gagaccctgt ctcaaaaaaa taaactaaat agattaaaat gaaaattaga agcaggtagt    26100
gtggaagttg aataagaata gccgccatgg gctcatgtat ttgaatgttt agtggcacaa    26160
cttgagtgag ttaggaggtg tggcctgttg gagttgtgtg tcactgggag tgagctttgg    26220
gattttagaa gcccaagcca ggcccaggga cttgctctct tcctgcgatc tgaggaactg    26280
gatgtagaac gcttagctac ttcttcagca ccatgtctgc ctgcatgctg ccatgttccc    26340
tgtcaaaatg ataatggact gaccctctga aacttggtct cttttggctg aggagttagc    26400
aaggtaagag gtggctgtgg cttgctcttg tttctctctc tctgatcttt catcattttc    26460
tcccgtatct ggctgtgggt ttttattatt aagagtaatt agaactcatg ttacagtggt    26520
acatgcatgc cacagaccca gtgtggatgc cagaggacaa catgtgtaaa ttttttcttt    26580
ccttgtatgt gcgtccaggc tagtttcaga cttgtgggct tctgcttcag cctcccaaag    26640
gtggggacca caggcttata tacctacact cacctcttta ttcccagtgg atgtgtgtgt    26700
```

```
gtgtgtgtgt gtgtgtgtgt gtgtgtgtgt gtgtttgtgt gttttacaca gacctgtacc     26760
acattcattt ggttacttt ttttcctgca ttttgttttt aggtagggtc tcactatgta      26820
accctgactg tcctggaaca tgctatttag attagactga cctgctggtc cctaccttcc     26880
gagtgctggg attaaaggtg tgtactacca tacctggtga ttagtttgtc ttttgagact    26940
gggtctcttg tagcccaggt tggtcttgaa ctcctggttt tccagactct accttccaaa    27000
tattgatatt gcaggtggtc actaccatgt gtggaattta ttttgagca gtgttctgtg     27060 ggtggatgat aaggtcatgt ctatggtaaa attgtttcta ataatgatga atagcttcat    27120
gtgtgtatgc atctatcagg tttgttcaac ctgaagtgta ggcctaatat ttggatttat    27180
ttagccagtg atagctatga attgagccca gaaaaaatca taaacttgac taaaacatct   27240 taagaattt gtaacttctt ttgtaactca actgtattgt ttctgagcat gaatgttgta    27300
aatgacaatg tcagctgcca tgtcaaaagg ttgaacatta cttggcagtg gtggcacaca   27360
cctttaactc caacactcag gaggcagagg caggcagatc tctgagttag aggccagcct    27420
ggtccacata gggagttcca caccagctaa ggtgacagag tgagaccttg tctaattttt    27480
ttttaaggtt ggacatgtat aattccagag aataattttt cactaatcgg aaaagaggca   27540
gtttcaactt ggagttcaca agatttaatc tttctttgaa gatttattta ttttagtta   27600 tgtgtgtgta tatatgtatg tatgtatgta tgtattggtg tgttaaaccc ctggggctgg   27660
aattacaggt ggttgtgaac ctgatgttgt aataagctcc cagaccgtag cacaaatgac   27720
tctatgaaga aagtaccatt caggctgtaa aatccacata gacagcacca cctggaaaaa    27780
ctaaaacaaa aatccaatcc atcaaactcc acagatctgg gaaagtatct aaatgcacta   27840
accttgattt ttggcttctg tagttctgct tctggctaac tattcttgtt aactgaagta    27900
tgtgaaccca caacatggtt tttgtgctta aaagttctct gttctacaga atgaattcca    27960
ggacagccag agctgcatgg agaaaatctg cctcaaaaca aaacaaacaa ataaaaacct    28020
tgagaaaggc tcagggctat actggtatcc catacactca gtgtagtcgc caactgtcaa    28080
agactttttg ttgacttaaa cccatttcta agcagtattc tcttatggat accccttaca    28140
agtgggtgct gggacttgaa ctcaggtcct ctggaaaagc agaggatttc tcacctgctg    28200
agcacctctc caggcccata agatctatct taagacaaga cctgagcagc cttatggaga    28260
tggcagtctg gggaaccact ggtgcgcctt ttcttctgct ggtcacaaac tgctgtggga    28320
atttccatct gaagttcctg cctcttctca cattccatga tatgagaaag ctatcaatgt    28380
tctaaatctg tttgctttct gctttgcaag accttctct ttcctaggtc accctccaag    28440
agttcttgac ctcagccccg actggtgtct tgggatgggt gactgggttc tggggcttc    28500 cctgtgcctt ggaatatggt aaaagagcat tcaggtatt cactcagtag atgctagtag    28560
cactccctcc ctccatttct gtctacagat gttgctagct ggcccctatg aggtagtctt    28620
tgcccctttg ttattgctgc agactcagaa aaaagaggaa atatagaact cctcgtggtc    28680
ttctactcaa tatccaagca aggggggaaca actgagcatc catacactgc tgttttggct   28740
tctcaattgc ttgcttgtac atcaccaaga agctttcatt ggtcagtgta aacaagatct    28800
gggagttgat ggtagagcag ttggatgagt gactctgtct ttcacctttg ttgagtcatt    28860
tggtgtgtgc acattgtggg tccctgcctc gcttcccatt aaatgtcaag gtgaacttta    28920
tgaggttgaa acttttatat gtagtgcaac tgtactcctt cctctctatc tcttccttca    28980
tttttcttcc ttcaccttct cttcctttaa aaaaagaaaa actttaaaaa atgtgaatct    29040
```

```
gatgtatccc aggatggcct caaactgttt gctttctcag aagatgacct tgaactttca    29100
atcctcctgc ctccacctcc caaatgctgg gcttacagga attcatcacc atgcctggtt    29160
ttcctctctc ctggtgagtg aatccagggc ttcatgcttg ccaggcaagt gttctgctga    29220
ctgagttaca tgcttagcct gtatccacat cttgactgag taatttctgc accaaaactt    29280
taggtttcat ctcagtgact ctgccaatgt gttttccattt tagagtgacg actggcctta   29340
gaggagagtg taagagaaat agagtctctt tccttggtct gcttttttaaa ttttaatttc   29400 ttttttagaca tcttatattt attcatgcat gtgtgtgtat aactagcaga actcagctgt   29460
ctctttctac cactcaggtc accaggcttg gtggcaggga ctcttacctg ccttcgagca   29520
ggctctgccc tccttttgga gaaactggtt tgcagaagga agagacagca cagctcagaa   29580
gacagccgtg ctttcagatg cctgagaatc ctgccaagga cactgctgca ttctcctatt   29640
cttttgtaag ggtcccatct ctgctgagct aaactgggct ttctcagccc ttctcctctg   29700
acagtatttt aaaaccctac ctaaaggggg atggagagat ggctcagcaa ttaggagcat   29760
atcctactct tccggagacc cctacttctg ttcccagcac caatgctggt caatttacaa   29820
ctgtaactct gctccaggtc atcggatgct gctatcctcc tcaggcaact tcactcatgt   29880
gcacatacac atacttaaaa acaaaataag tcttaaaaaa tcacctaaga aatataaagg   29940
cacatatcat aattcagcct gctgtgacgt atagctatag tcccagaatt ctgaaggcag   30000
aggcaagagg atcacctcaa gcttgggcc  agcgtggtct acagtgagac cctggagact   30060
ttaatctcaa aatatgtaac aaaacaaata tgtaaataga catatatcac aatttatatt   30120
taagtaaaat ggggggcatt ggagagatag ctttgtggtt aagagcatgt actgttcttg   30180
tcaaggaccc aagtttgatt cccagtgtct acactggttg gtctccaacc caattccaag   30240
agatctgctg ccttcttctc ctctctactg gaactgcatt catgtgcaaa tgtccatatg   30300
cacacacata cccacatgca tacacacaaa cacatacata ctcattttgc ctgacatcgt   30360
ggtaaagtgg gaagacttgt tgccctatta cttggtcttc atttgcctat gagcaccatg   30420
ttggcatgaa ctcattcatt aatatctttc ctgtacaact ccccaataac caagatgaca   30480
cttggcacac attaattgct aagtataatg aaaatttagt ttaaattagc taaataattt    30540
aaagttcccc ctcaagcctc atgcctgatt taaagtagta cttattaatg ctgggcctgg   30600
tggcatacat ttctaattct aacacttagg aggctgaggc aggaggatgg ccaattcaag   30660
gccagcttag ccagcttagt aagaccttgt ctccaagcaa attacagcaa agtctgagat   30720
atagttcagt aattagggtg tttgtctacc atgtgtgaag acctgagttc agtttctaac   30780
aacaaaacaa aactaaacaa accagaacct agaggttatc atttattttt ttattttat   30840 tttttttgg agtttatgcc tttgattat ccattctatg tccagacatc agtactgcca   30900
tgttacagtc aataaaagtc ttccttcatc acccttaatc ttatcaccac taaagtctct   30960
acttgacaga catgccatac ataattatag ctgttacctt ctatcataaa gtagacattt   31020
tattttattt gtgtattcat tttcatttat tttgttgttg ttgttgtttt atgagacaga   31080
gtttctctgt gcagccctgg ttatcctgga actcactctg cagaccaggc tggcttcaaa   31140
cacacagaga tccacctgcc tctgcctcct gagtgctaag attaaaggag tgtgctgcca   31200
tcttcccagc aacattctaa attatttttt gtttatgttt tgaaatggtc taatgtagct   31260
gaggtgggcc tcaagcttgt tatatagctg gggaaccttg aacttgtgtt cttcctacct   31320
ctagaactct ggagtgctgg aattacaggt atgaaccatc acattccagt tttaatcaaa   31380
tccagacttc atgggtacta ggaaagcact ctacaaatta aacttcaccc ctagttcata   31440
```

```
tatatatatg tgtgtgtgtg tccatgtatg tatgcctaca tgattttatg tgtgccacat   31500
gtgtgcaggt gctcttggag gtcagagggt gtcaaatccc ctggcacctg agttataggt   31560
ggttgtgagc cacctgatgt ggattctggg aactgaactt tggtcctctg caggagaagt   31620
cactgttcct ctgagtgaac gtttctactt tttaatatac ttcccattcg aattagaaag   31680
tagaagctct cggaggttga gaccttacct aaagtcaccc aactagtaag aaaactaaaa   31740
tatcaacttg gttttctgag ttttaaatat tttttcccaa tgtgtaatta cacaggagaa   31800
ttaatgggga cacttcaagg taaaacagaa gctttagaca tagcaaggca tggtggcaca   31860
catcccattg agaggcagga ggatcaggag gccagctttg gctgcatact taagaggcat   31920
ccagggctac atgaggcgct acctaaaaaa attaaattag gcagggcgtt ggtggcgcac   31980
gcctttaatc ccagcactcg ggaggcagag gcaggcggat ctctgtgagt tcaaggctag   32040
cctggtcttc agagcgagtg ccaggatagg ctccaaagct acacagagaa accctgtctt   32100
gaaaaaccaa aaaagcactg gtcattgtca ttttctttcc taacagggca ctggaaccct   32160
gatgttggtt ggctcctaga tttcttctcc acagcagaga gttcttgccc tgttagagcc   32220
agaaggatgc tctggagagt cagtatatag caaagcaggg tcatctggag tagtaaaaac   32280
cctctggcac agtcagacct catttcctct tgtcctgtgc tcgtggctct agcattatgc   32340
aaggagaggc gcaaacagca aacaatttgg aagggctagc acttgagcaa ctctttgtag   32400
cttcctcttc tctactcttt tgcccctggc ttctactgga acaggtgact ttccattgca   32460
ttgcattctc caaactcaga tgattttgag aatgtggcac tactaaaagt cacatggaca   32520
tacaaggtac aactagaact atcccgggaa acagtgatac acgatctagt ttgaggcctt   32580
gagccatagc ttgtcagaag ctcagaaatg attgagtctc tgggagccct cacctcagca   32640
tccctgcttg caaaaggctt cttgaagtag taaaaactgc tgggaccttg tctaggctgg   32700
gtaaccttgc ataattactc aaccttactg agctcagtcc cctcctctat aaaataagtg   32760
caacagtatt taccttagtg gcccacctga aaacatcaca gctgccatag ctagctcttg   32820
gcttttgttc tatctcctcc tcccctact ttctcttccc tccctccctc cctccctcat   32880
ttttctttat tcctttcttt gtatttttt cttttttctt cctcacacct ctccttattc   32940 cccacccctcc tctctctctc tccttccca cttctctttc tttcatggca ggatatcatg   33000
tatcctagct atacttgaat tcactatata gctgaagagg agcttccagc ccttttgcct   33060
ctgcctccca agtgctgaga ttataggtgt ccacctccac gtctacttat gctttgctaa   33120
ggatcaaacc agggctttgt atgtgcatgc taggcaagag ccaactacat cgccagacct   33180
atataatacc cctttctcag cgaaactggg gttgctgatg gctggtgttg ggggaaggca   33240
ctaaatattt agcagaagta taggaaaact ctagaagtct agagatcctc aaagtaagtt   33300
tggagagcct tggcctttc ttagttgaaa gtcatggtgc ctactcactt tgactgctca   33360
aggaatatcc attcaccacc tggaaataag aaaggaggga gaaccagcta gggatgtgac   33420
ttagtagtag agcacttgtc tagcatgagc gtggtcctgg gttcaagctc cagtacaaag   33480
gctgggtggg ggggtggaga aaggcttctt cccatggcg ttctagagat ggcggggaga   33540
aaccaccaat ccacatctat ctacaacagt tcaagtagaa ctaatcttgg tggtatggct   33600
atagtagtcc taatcccatc tcagggatgc ttctctttgc aattgataca aaacacatta   33660
cagaaaacca cagtgaatca aaatgcagag ttgtggtgcc tagttccaat ggatgcatct   33720
acagtacaac tcccatgcct aaggctcagg gatcattgtg gaagacaaag atcctcccag   33780
```

```
gagatcaggg agtttgctgt ctcctaggaa tttcagaaaa tacatctgta aaggctcacc   33840
aacgtgaatt cctaaacatg agctgaacaa ggatgacaat agacatgcta acaaggatgg   33900
gaaaaagccc ttgaagcctc agacctacac aaagagccgc agttgattaa ggaatgctga   33960
ttgtgggaga aaccatcttc ccaaattgtt atctaatacc acatagtcag ccctgaaaac   34020
acacatgcaa ataagattat acaaaacaag ggggttgtac atatgtattt aggaatatat   34080
atatatatat atatatatat atatatatat gtaacaataa ttaatagaaa aagagaccat   34140
gaatttgaaa aagaacaagg aggggtacat ggaagggttt aggatgcttt gacccttaa   34200 tatagtttct tgtgttgtgg tgaccccaat cataaaatta tttttgttgc tagttcacaa   34260
ctgtaatttt gctgctgtta tgaattgtaa agtaaatacc tatggttttt gatgatctta   34320
ggcaatccct gttaaactgt cattcagtcc ccaaaggggt caagacccac aggttgagaa   34380
ctgctgattt agagagagga aagggaaggg ggggtgaaat gctgtaatta taattccaaa   34440
aaaaaatttt taaaaatttc ttaaaggaac tgaagaaaag agctgaacat tctaagctta   34500 agggggggaaa ggttctggaa tgttacattt ttctggtttc cttagtctca gcaacaggct   34560
cccagccttc tgtttggaca gtggtttaca ggcatgtgag ctcagggaac actcttccaa   34620
gtgaatcaga cttcaggaga agacattcag ttcagggccc tggggaaagt aaggacagaa   34680
ctccattcct gagaattacc aggtttgctc agaagataaa actggtgagc ccaatggctg   34740
tgtgcacaac cctgacctca gtgtctagga tagctggact ctagctgcta aagatagtc   34800 agagggccat cctttccctg aggctaatct gtgaatcaag taaactacag tcaggaaggg   34860
agctggagat gggggcccag caaacaggtc cccttaaag cccagcacat aggtggggaa   34920
cccaacctcc cattttgtct tcaccccacc accaggcctt taccaaggcc cgaggttgcc   34980
actattttca gcttgccagg ctcttttgcag ttttagggggg atgaggagga gatgctctga   35040
ggtgctggga ggcacatggc gggtgctatt tatggcttgg gctgaactcc gatgtcctag   35100
aaagagtgtt tctgacactt tctgccttct gggaatcagg agactcatga caaacactgc   35160
ctggcagtgt ttctttcttg ttcacagcaa gaagtgtgca gtccatggca cgaaagaggc   35220
ctgagcaggg caagatggac acgatgacat cactgaagga gcttcccagg ggctgtcttg   35280
actgcttcat taactcattc atgcagttta ttcagcagct atgcctgtca gaccccattc   35340
tgtctgcaca agacacatgg caacaaagga gacttactat tcccatcttc atgggtttta   35400
tgttctggca agaggaagat agtaataatt tttaaaaagt aaccagtctt gagagcatga   35460
taaatatggt tgataacaat atgctatatt ttaaagttg tgagatagta tactttaagt   35520
gttctcaaaa caaaatgatg aatatgggtg atataacatg ttaattggtt taatttagcc   35580
atgcctttgt gaacatactg tatcgtgtat cataattgtg catgactta tttatgagct   35640 aaataaatga atggaaaaaa aagtaaccag tcttgatgct tacctgccat cctggaagga   35700 aatgaaata ggatctgccg ccgcagcatt gccctatgct cttatttctt ctcttgaaga   35760
ggtaggggtg tgtgtgtgtg tgtgtgtgtg tgtgtgtgtg tgttactaga gactgagcta   35820
ccggcctcac acattctagg caaatgctct actttatatt aaacacttta taaaacatta   35880
agcctttcag ggtcagcaag gtagctcaga gagtccgggc atttgctacc aagcctgaca   35940
acctgagttc gattgatgat cccccagact cacgtgatag gaggaagctg acacctgtgg   36000
gttgtcctct gactataggc atgcacacac atcccatgaa taaatattta tacattttca   36060
aatcatactt attttacaat gatttttatt tgtttgcctg tctttctgtc tgtgtagaga   36120
caaggtttca tgcagctcag gttggcctca aactcactct gtggcaagga tgccttaact   36180
```

```
tcaggtcttc caggtccagg taacaaaatg ttcaggagga acctggtacc tcatcataac    36240
cggttctaga tggtcttccc agggctgctg taagaaagtg ctacacgacg agttatttca    36300
aacattctca cagttctggg gattagaagt ttgaaactaa ggtgctgaag agattagttc    36360
cttctggaag ctcagaagag ccatctggtc catactttto tccaggtttc tcttagtttt    36420
tggcaatcct tggaatccct tggtttgtag atgcagcttc caaagctcaa gatctctctc    36480
caatgctgtg tggcatttcc ccgtgtttat gagtgtctaa atggctttta aaacatttt    36540 tgagatgtga aattctggct gacccagaat atataaacca ggctgacctt tgtctcccag    36600
agatctccct gcctctgctt cccaaacctt ttgattaaag gtgtgtgtca agtgcccaga    36660
ccaaatgccc ttcttgtaag gacaacggtc atattggatt tagtgtctaa gtgagtcccc    36720
tatgaactca tctcgaactc agtttgcata gaacactgta ccatgcaaaa taatgacac     36780 agagactgat attggggttc acacttcaag ctgaaggtca gaaaagcaaa gcattgggcc    36840
actagctctt accactacct caggctgaac gggctgatcc tgctgcctct cctcagcatg    36900
gctggagaat atcttcatat cctcattgtg gctggaaaat gaatgcctga tatggagaac    36960
ttgctcctgt tttatataac tccctaatgc tgggattaaa gatgtgtgat cccaggtgct    37020
gagatcatct ttgtgtgagc tgtttctctt taggactgga tcaattttgt gtagatctgg    37080
atggctttgg gctcactgag atctatctac ctcttaatcc ctggtcctag gattaaaggt    37140
atgtaccacc acatcctagc ttctggctgc tgggattaaa ggtgtatgcc tggcttcgat    37200
ggcttgtggc tgactttgct ttctgaatcc gcaggcaagc ttaaaaaaat cataaataat    37260
atatcaccat agaccacact tccaaatagg cttccattta gaggcgccag tgggtgataa    37320
tgtaggcgga tttactcagt tttgtgcaga tggctggcgt cctgtctggt gagttcagat    37380
tttttttttt ttttttttta agttcagaat cttacccagc tcagcttttc aggctgcatt    37440
cagtgtccgg cttttttctc accgtcttga cttcctgtcc tgcatcccat ttctcagcct    37500
ggaccctgcc agtctatcag atagataaca taaacaaaat tgtactggat taatgggagc    37560
tgtttggaca tttcctactt ttgccttttc accaatgatt tgcatactta agcctgcaac    37620
tacagccccg atgcagtaag ctcagtctct ggcaagcaaa ggtctctctg gggtcttgtt    37680
taagaaccag ctcaggctgc tggctctgtt ggcagtggag gtatttccta taatgggatg    37740
atgggatggg ttattcacac acatctcagt tactgggcta catggatcca aatcagccac    37800
ccaagggttt gcagtcacat gtgagtcact tagcacagag aaagaagcct ggaggaggag    37860
gggtcctccc agcttcagga gggttttcca ggatataggc ttctagtctc gttttggatc    37920
aatttatcag ttttggattg ggtctaataa ctctttcctg agcctggact gggctcaaag    37980
gcatgagtat gtgaggggaa tttactagaa ttcacctgta gtttctgtat cattcctaga    38040 gaagggaag tagagacact ggtgatggga aataaaaaca aaacaaaacc taaatattgg     38100
gagcacagag gtccttgttc cacagctctt gatagaagtc aggaatgtta tgtatgtaca    38160
attgcccttg aaaaggaaag gatgtatgac ctgttttct gtcccgaagg ctgggaactg     38220
gggatgatta acagcctgtt gatctgcatt atctgaaggg ctaggccata tcaagctccc    38280
acagctagca ctgaaggaga atagggcctt acaaaggaa ttccctcttt ggatcgaacc     38340
taggaacatc ttctgtttta ccgctctctc cttgtttcat ctgcaaaggg aggagcttgg    38400
tagtgatgtt gaggcaggca ccacttgtat ttttctaagc cacagagact gtttccctac    38460
cttacaaaca tccctgtgca tcactgcagc tctgtctctt atggcagtgt ctcagttagg    38520
```

-continued

```
gcttctattg ctgcgactaa acaccatgac caaaaaagct cacacttcca tactcctgtt  38580
cattattgaa gaatgtcagg actggagcgc aaacagggca gggtcctgga ggcaggagct  38640
gatgcagagg tcatggagga aggctgctta ctggcttgct ctccatggct tgctcagcct  38700
gctttcttat agaacccagg accacctgcc cagggatgac accacctaca atgggctggg  38760
cgctaatatg agggatcaaa gagatggagt tgtgggaggg acagaggggg agagcaatga  38820
aagagataat cttgatagag ggagccgtta tggggttagg gagaaacctg gtgctagaga  38880
aattcccagg aatccacaag gaagacccca gctaagactc ctagcaataa tgaagaggat  38940
gtctgaacgg gtcttcccct ttaatcagat tagtgactac cctaattgtc atcacagaac  39000
ctacatccag taactgatgg aagcagatgc agtgatccac agccaagcac tgggctgagc  39060
ttcgggagtt cagttgaaga gagaagggat catgtgagca agggggtggg ggaagtcaag  39120
atcatgatgg ggaaaaccac agagacagct gacccgagct agtgggagct catggactat  39180
gaaacgccag acgttgtaga ctccctaagg aaggccttac cccctctgaa gagtggatgg  39240
ggggtgggaa gtggggacgc tgggggacag gagaaaggga gggaggggga actgggttgg  39300
tttgtaaaat gaaaaaatag attttttta aataaaaaaa gaaagtgctt tacatctgga  39360
tttcatggag gcattttctt aactgaagct ccttcctctc tggcgactct agtttgtgtc  39420
aagttaacac agaaccagcc agtacaggca gcagaaatac cttgcagaaa tatcttagtt  39480
caggagtcca cggtggtctc agtcacttcc tcatgtgcca cctgagttta acattcccca  39540
aaacttggaa cacaggccac cacatcatgg agccctggct taaagctcaa gttttatggt  39600
atttcttttt atcactgtct ataattccta aacatgctac aatgttgtga gccctcaccg  39660
tctcctaggt ccatagtgac ttcctggcat taatagactg tgccccaaga gctctatggc  39720
cacgaccacc acctgccatt cccctccccc tccatggtcc cagcctcact tcttcacttc  39780
ctggtccttc cgagcccaat gtgcaaaccc acagaatctg tctgcttatg taagtttcct  39840
ggtcactgag tggggtgact cagcaccaag gtggtgccct gcgatttccc agccccaggc  39900
agcagaacaa ctgaaatgga aaacaagtcc cgttaatagg gtccagctga gagcctccct  39960
ttctcaggga gtctggcaaa tctactcctc ggggaactgc cctgggcagt ggaattctcc  40020
agctccctgc tcatttccta gttcctcttc cctcttctca cctttggctg aggatcagaa  40080
aggttcccac tgaggtctgc tttgccctgg gcctgctctt ttcagagtcc catttttgga  40140
atgaattttt tttgtctcct actttcaagt tcacatattg aagccattat tgccaaggtg  40200
atggtatcag aaggagggac ctttgggaga tgaatggatg gattccaaga ggttatgtgg  40260
gcagagcacc catgatgggg ttggtgcctt cataggaaga agacacagta gaagggaaag  40320
agatgccgac tgaaaaacag gaagtctcct ggagtaggcc actcagccta tgacacgcca  40380
gcactcagat ctcggacttc ccatctccca aatggtgata aacaaatgct gttgtccagg  40440
ctgcacagtc tacggcattt tgttgcaagg gcctggacca accaggctca ggcaggaagt  40500
gaatctagtg tgggaggatg tacagactgc cactcagtct ggacacaaac tgtcctcagg  40560
gatcacctga gccacatcta cctaagaatg gctattcttt ccatttgtta acatcaaatg  40620
ccaagcccct actgtatgta ggctcttgct agcagtggat atgatgctat gtgagatggg  40680
agcaatcctc tctgcacaga actatacata gaactatgca tagaagacca acagggagac  40740
atcagataac tattaactgt gatagctctg tgggagacaa acagaatgag ggaatggaca  40800
atgactttga ggaaaaacta tgattgaaaa tactctatct ggctgggcgg tggtggcgca  40860
tgcctttaat cccagcactt gggaggcaga ggcaggtaga tctctgtgag ttcgagacca  40920
```

```
gcctggtcta taagagctag ttccaggaca gcctccaaag ccacagagaa accctgtctc   40980
aaaaaaaaca aaacaaacac acaaaaaaga aaatattctg tgaggtaaac aagcatctgg   41040
aagggttggg agataatgca ggcaaaaatg cattagacag cacacagtac aacacagcaa   41100
tcaaacttaa tataaacaca gcaaatgtca tctttgggct ttgccccatt tcctgatctg   41160
accataacag cctagtgtct ggaaagcaca ctaaagccat ttacgtcaca caggagttca   41220
atgttgagtt cagagggagg gggtggaggg cagattagcg aggtacaagt tctggtccct   41280
ttgatgaagt gttgatgtac ccatcgacac cacacaaata taccatcatg ctccatgtta   41340
gggtcagtga aggattgcat atgtgacggt ggcccactgg gctgagaaag ccctattgct   41400
tagtgacatc tgtgataatg acatgcgagc cctattgctt agtgacatca ctcttctcat   41460
agtgtgggat ccaatgtgtt tcttgtacac ttgtgataat gacatgcaaa caagtctatt   41520
gtgcggccag tcacacaaaa aatatattat gtgcagtcag gaacagtcca tagtacttga   41580
ttgggacagc acaagtctgt gttgctggtt cacacattaa tcattaccac tgttttagtg   41640
tgctcctata tatatatatt taaaaattac tataaaatga tacaccgtgc tgagcaatag   41700
cacctcttat accttgtgtt tactggatgt actcaagcta tttctcttg tgcttgattt     41760 atttgtattt gtattttga gagaacctca tctagtccat gctggcttca aacttgttat     41820
aaagctgagg atggcttcga actcctgatc ccccagcctc tgcctcccaa atgatgagat   41880
tacaggcata tgctaccaaa catgactttt atttattttt attacttagg tggtatgggt   41940
ggtttgaatg agactgtccc ctttggctta tatatttgta ggtggaccct tggaaaggtt   42000
taacaggtat gaccatagtg gaggcagtgt gtcagtaggg gaggtctttg gggaacccaa   42060
tactcaatca attccaagtt agggctgtct gtctgtctgt cccctgattg tgtcacaagg   42120
cagaaactct cagctactgc tctagttcta tgcctaccca cctgttgcca tggtccctgc   42180
catgatggtc atgtacttca acccttgga taggtggccc ccaaattaaa tggtttcttt    42240
tataagttgc cttggtcatg gtgttttgtc atggcgataa gaaagtgact gagacaggtt   42300
tgttgctgtt gttacaaggt ttagtccagc atctggcac cacctctggc ctgtgcttga    42360
ttcaatcatg ttacctttag aaatagcagg ctaaaggaca tatacctgtg tacgtatatg   42420
tgtacgtata tattagctgt atagtctaag tgtgcacctg actctaatat ctaggtttgt   42480
gtaagtagac tccaccaagc tcactaagca atggtatcac agttttcaga tagtgttcag   42540
cgatgcttgg ctgagtgtta gttctttttt taatattta tttatttatt atgtatacaa    42600
cattctgctt ccatgtatct ctgcacacca gaagaggaca ccaaatctca taacggatgg   42660
ttttgagcca ccatgtggtt gctgggaatt gaactcagga cctctggaag agcagtcggt   42720
gctcttaacc tctgagccat ctctccagcc cctgagtgtt tttaaatcaa ggaaaaaagc   42780
ctgagggaag ggagctcagg ctgaagggga ggagtcaaga cagtctgacc ccaaggcatt   42840
gtgggacgta aagagttctg ggacaagact gaggtctctt ccttctcaga gactgtgggc   42900
ttcagtttcc ttggtagccg gaagcaaagc taatccatgg cttaaaatat aatactcagt   42960
gtaaccttgt gttgtagaag tgacttgctt gtcttcttcc ataattctaa aacatctttα  43020 agagcaggat ccaggaaggg aaaaggagag attctcatct tcttcaaaag gcagctttcc   43080
ctaaagcatt ttctgatgaa atttaagttc taaaaccagc agtggtataa tcccatcatg   43140 aatgggatc tctgagttta aggccagcct ggtctacaga gcaagttcca ggacagccac    43200
ggttacacaa agaaatcctg tcttaaaaca aaacaaaacc caaacaaac ataaacaaaa    43260
```

```
actatccaaa accaaccaac cccccccaact cagaaagaaa gaaagaaaga aatcaagaaa    43320
gaactgccca ccgggtgttg gtggtgcaag cctttaatcc cagcactcgg gaggcagagg    43380
caggcagatc tctgtgagtt tgaggccaac ctgttctcca gaaagagtgc caggataggc    43440
tccaaagcta cacagagaaa ccctgtcttg aaaaaagaaa agaaagaact acccatgacc    43500
aaacagttcc atggccaggt agagaatgag gacgctgaaa gtcacacctt ctcagagtct    43560
caaactgcac atctggcctc aaagtccaga aatgagtgca agaccattaa tgacagtctt    43620
tggaaacaaa ccagaccaaa gaacatttgg ctcctgatac atattctgag ggtcacatag    43680
aaagaaagat ctgcctttgg ccacctcctt ttgaagtggg gaattttatt ttcttctgca    43740
tggaaacttc atgtaggtat ttgagaatac atacagacat gcaggtgcac atgcacggac    43800
atgaacacac acatacaccc cgggtaggca ggcaagaaag tgtgtggaat aacacttgaa    43860
cttcccttcc agaacagaag ccctctgaag tgtgacattc atgctggctg catggggtct    43920
gatcagtact agtgagtgga ggtggagggg taggaaacat ggggatgata ataggttgtc    43980
aggaaagtgg tgccccaggt agcacagagt agaaatttgt cccccaaaat ccttttgaac    44040
ccagttgatt tgaatgccgt gcccctgcca cccaggcttc agagctaagt gacttatgtc    44100
ttcaggtcag tgatgattac cacggttgca gtgctaacac agatgcttta tctaccagga    44160
cagaaacaag aaagatgctc cttcccaggc cccttagcac tctctgggtg gggaggattg    44220
ccccaccttc caaaaataga atactgtttt ggtaaacagc cactttgagc ccatgaggat    44280
atcttcatta gctatggaga caggttttag taagaaagca agatgagagg ctaaaaaacc    44340
cttggggagc aggaactggg aagactgtgg taccttgttc ccagatccac cagaaacctt    44400
gccaccagac gatgtgtcca ggccccacat atttcacaaa aagttggatc tgataacaat    44460
gaggatggaa tcccggtctt aaggtgggtt tggggtggga agaggcggga taatgggtga    44520
gagggtcggt ggggacaggt gagatggggt atggtgggga gaggtggaat ggggtggggt    44580
gggttgagat ggagtatggt acagcgggga gggatagaat tgtcttttcc ctgtaccaca    44640
gagaagtttg actgctaccc ttggcaatta atcaattata gaaaatgcaa ctttgctttt    44700
aaaatgtgtc tatttccaaa ggcttcttcc cctcccctac ctaggagaa ggaaagaatg    44760 gataatgcta ctgtagagga gggtagcatc actatagagg cctcagtatc tgccccaggg    44820
agctgggaga gagttctatc acacaaacac agcccgagtc acatactcaa caaaccccac    44880
aaaacaaaac aacaataatg aagatacaaa atctcattat gtagcccagg ctagtcctag    44940
atttctgttt tcttttttg ttttcgaga cagggtttct ctgtgtagct ttggagccta    45000
tcctggcact tgctctgaag cccaggctgc cctcactcac agagatccgc ctgcctctgt    45060
ctccagagtg ctgggattaa aggcgtgcac cactaatgcc tggctagtcc tagattttt    45120 tatcctcctg cctcaggctc ccaactgttg ggtttacttt tgggagtcca ttttcttcca    45180
gcatggattc tttgaattga aattcagatt atcaggtttc tgtagcaatc ccaccagccc    45240 attttttgt ctgacactgc ttgttttgag acacagtctc ccactgctgt agcccaggct    45300
gccctagatt ttctatgtag cccaggctgg ccttgaactc ccaggagtcc tctggcctct    45360 ccctttgat tactggaact agaagaagtc actatgcttg acttggaact aatattagaa    45420
caaaatatat ttttcattga gattcaactt tgaaatcctg atgctcctgc ctcactcagg    45480
tcatcagggt tggcagcaag agccttatc cactgagtca tattgggccc tgacctgctt    45540
ttaaattttg cctttaggc tggagatgta gctcggctgg ttcagtgctt gcctggtacc    45600
cacgaagccc tgggtttgat ctacaacaca gtataagcca ggcctgatgg cgtatacatg    45660
```

```
taatcctaac acttggggag caagagggag gccaaagcca tcctctgcta cttggtgagc   45720
ttgaggccag cctgggatcc ttgagaccct gtttcaaaac aataacaaca aacacagact   45780
actaaaaaaa attaataagg gccagactgg gtggtgtatt cctttaatcc aagcaatgag   45840
gaggcagagg caggcaaatg tctgtgagtc tggggacagc ctggtctact gagcagcagg   45900
ccaactaagg ctacatagtg agactatctc aaaaaaagca aaataacaat aaacagacca   45960
gttccccatc tcctattttg cctttacctc ctattccctg ctcagcaggt tattttttgt   46020
tcctgcatct tggttcactg atctgtaaac ttgtctgaat aagtaggtac agggttgttt   46080
taaaattaga taatatattc aatgagaagg gctaccaagt gctcaaccaa tgtatgcata   46140
tgtatgtatg tatgtatgta tgtatgtatt tattttgtt ttgttttca agataaggtt     46200 tctctgtgta gttttagagt ctgtcctaga acttgctctg aagagcaggc tggtcttgaa   46260
ctcacaaaga tccacctgtc tctgcctccc aagtgctggg attaaaggca tgtgacacca   46320
cccccaaagc caatgttctt ataggcatct ttgattttt ttctctttct ttgagtggag    46380
tctgactaag tagcccatac tagctctgca tttacaatct gaacacatgg ataagagtgg   46440
tgaaaattat caagatcatg ttatgctatg cctcctgagt caccatgccc tgcttcagac   46500
ttctttgtat taaagaactg tgtaaaaaaa aaaaaaaga catttgaagg cacataatca   46560
gaggaatttg tcagtgattt ttcacatact gtcttatttg tggccaaggt aagcctagag   46620
agtatttctt aaaattaaaa atagtgggca gattttggag gcgatctgat atgaaaatcc   46680
cttcccaccc caggtagtca tgggctgact atcaaggata cattctgaga catatatcct   46740
caagcagttt ctgccttacg caaatatcat aggtcatagc acactgagac tatgtggcag   46800
tctatgtgtc tatatacaca tggtgtggcc tattgttccc atggtcacaa agaacaaaac   46860 aacttttca caaggcttta cccctagagg aagagctaca ggcaatcaat ggttgctgag    46920
aggagtatca gtcttctcca gggacttagc caatcccaag aggtcagcca cgcataggaa   46980
cgcttagcca cgcttgtata gaacatctca aacaacaacc acctcagtgt aaagcaagca   47040
cacaaggaac tgatgcaact aagagacaaa gggcccggtg tgtgtggccc gtagctgtca   47100
tcccagcact tgagactaag gaaggaaggt tgagaatttg aggccagcat ggactccaca   47160
gaaagaccgt tttctttctc agaaaaaaga agcaaaaacc aagaacaagg tgtatgggaa   47220
tgctactgtc ttggcatatt gtttatagaa aacttttta tatataaaag gaatgcacta   47280
caaaaattat aaactactgt aatattaact gcatagatct ataacatggt catttattat   47340
tgagtatgat tatctatcta cccacgctgc aggtttagac agttgcacta cagtagatct   47400
gtttgcagta gcatcattat tagacatttt ggacaaagcc aagtggtaat ggcacatgcc   47460
tttaatccca gcacttggga agcagaggta ggcggatctc tgtgagtcag agaccagcct   47520
ggtctacaaa gaactagttc caggagagtc tccaaggcca cagagaaacc ctgtctcgaa   47580
aaaccaaaag aaaaaaagaa aacaaaaaac taaaaaataa ataaatttgg ggcaatatct   47640
tgtcctatga tgttactggg taatgggatt tcctcctctt gtattatttt ttctttgggg   47700
gttttactta ttatttactt gagacagagt ctcatttatg acaggctggc ctcaaacagg   47760
aaatgaagcc aaggaagacc ttgaagacct aatccttctg tttcttcctc ctatatggtg   47820
agttaaaggc atacagtacc atgcccagtc tattcactgc ccagggcttc atgcatgcta   47880
gcaaagcacc aactgagctg catccccacc cctcctcctg gcttccatct ccttatgtag   47940
ctagaaatga gcctgtctgt ctcaaatact gggattatgg gtgtgtgcca ccacacctgg   48000
```

| | |
|---|---|
| cttcctatta tagccttgtg ggatcactgt tgtttactga agcattgtga cacactgcag | 48060 |
| attgctggaa cagcgtctgc catcatcatg acacaacttc agagaaagag agagttccca | 48120 |
| accagccaca cacttaactc aatgcctgta gcccttattc tgttaagacg atttcctgcc | 48180 |
| atcttactca aagaccctct ttaactcggt aggaacatct gttacactga agtcctgcc | 48240 |
| tgttgctcca ctgacctcct tcacaaatta ttatattttg gagccaattc tgaacccagg | 48300 |
| ttttctgagt gacacatttt agtattttt ttttctttct attttctttc atggaaagtc | 48360 |
| tcttgttact gttcacatga ccaaggatca ctgcatcatc ttccaaggcc aattttggat | 48420 |
| gtttcagcaa gggagactga agatcctgag tctcagtgtt gatctccttt agaatgtcct | 48480 |
| ctggagaagg tagtgacaac actgcaagga taataggtga ataaagggaa gccagagtgt | 48540 |
| cctctgggat gtgcggcact tacatgaagg attcatttat aaattttaag ttatggagta | 48600 |
| taataataag actaaatatg tagtgtcgta attttataac tatacatatg tatatagtaa | 48660 |
| atataaattt atatgtaatg tatttatagt aagtgtacat agaattgaac atatgttaca | 48720 |
| taaatggcag aaaggaatga ttctcaattg ctttttttct aattataatt tctattgctc | 48780 |
| tttgtggatt tcacaccatg cattctgatc ccacttatct ccttgtctcc ttgcatttgc | 48840 |
| cctctgccct tgcaacctca cccccaaatc aaagccaaat ttaaaaaaaa aaccaaaatc | 48900 |
| caaacaaaac agagacaaaa caaaaataaa agcaacaaca aaaaaaggag aatcttgtca | 48960 |
| tggtagctgt agtgtggcct gttgaatcac acagtatacc ctttagtcca ttcatctttt | 49020 |
| cttccaagtg ttcattgata caagtcacgg tctggctcga ggattctggt ttctgctata | 49080 |
| ttactaataa tgggctctca ctggggctcc ccttggatat cctattgtcc tgtgttatgg | 49140 |
| agagcctgct gttttggata tgtaggtttg tccccttcac atgctataac aattcataaa | 49200 |
| ttcagtgaat gttggggtgg gccaactcat agccctggtt ctgggcttgg gtggtattat | 49260 |
| taaacccact gatggagaat aagaccacta ccataattta aaagccaaat tgaagcaagt | 49320 |
| tttaattcaa tactgcccag gtggacaggc tctggctagg tccatctctg agtttccagg | 49380 |
| aggtggccct gactcacggt ttacagtggc ttgagtattt tccataaggt ccaatcaggg | 49440 |
| gcaagcatac atcctgatgt acctccagtc tatatccaat cggggggcaag tgtacatctt | 49500 |
| gatgtatttc ctgcctgtga acctactgcc cacatgtgat caagcacatc cggtgcagtt | 49560 |
| gggtcaaaca gacttgttta gggcaatgaa aaacacatgg cttttatct cccataaaca | 49620 |
| atagcctcca gcggttcagg gactatttgt ccttgggcaa ggaatttaca gatcctatag | 49680 |
| gtgagtcagg gtcagcatcc tgctctcatg ccctcagggc tggctcactt gttacctccc | 49740 |
| cgaccctctc tcaacagggt cagctctgag gtgctgccca ggtggggtgc agggcctact | 49800 |
| cttccgcatg ttgcagctgg tcaggttag ttctctcata tgccacaggt ggcaatgggt | 49860 |
| gaagggggag ggcatgtttc cctcatcaac gccattacat gggggatgg ggtcagctct | 49920 |
| catgccctta gggttggctc acctgcatcc ttgaccatag ggtcagctct agtatgctgc | 49980 |
| tcaagtgagg cgcacaccta | 50000 |

<210> SEQ ID NO 4
<211> LENGTH: 34
<212> TYPE: DNA
<213> ORGANISM: Enterobacteria phage P1

<400> SEQUENCE: 4
ataacttcgt atagcataca ttatacgaag ttat                              34

-continued

<210> SEQ ID NO 5
<211> LENGTH: 34
<212> TYPE: DNA
<213> ORGANISM: Saccharomyces cerevisiae

<400> SEQUENCE: 5
gaagttccta ttctctagaa agtataggaa cttc                              34

<210> SEQ ID NO 6
<211> LENGTH: 23
<212> TYPE: DNA
<213> ORGANISM: Escherichia coli

<400> SEQUENCE: 6 cctgctttt tatactaact tga                                           23

<210> SEQ ID NO 7
<211> LENGTH: 22
<212> TYPE: DNA
<213> ORGANISM: Cricetulus griseus

<400> SEQUENCE: 7
taaggcctca tatgaaaata ta                                           22

<210> SEQ ID NO 8
<211> LENGTH: 22
<212> TYPE: DNA
<213> ORGANISM: Cricetulus griseus

<400> SEQUENCE: 8
atagatgtct tgcatactct ag                                           22

<210> SEQ ID NO 9
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Pro Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
            20                  25                  30

Ile Lys Ala Gln Ile Phe Pro Asn Gln Cys Tyr Lys Phe Lys His Gln
        35                  40                  45

Leu Arg Leu Arg Phe Gln Val Thr Gln Lys Thr Gln Arg Arg Trp Phe
    50                  55                  60

Leu Asp Lys Leu Val Asp Glu Ile Gly Val Gly Tyr Val Thr Asp Arg
65                  70                  75                  80

Gly Ser Val Ser Asp Tyr Met Leu Ser Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

```
Val Leu Asp Ser Leu Pro Gly Ser Val Gly Leu Ser Pro Ser Gln
            165                 170                 175

Ala Ser Ser Ala Ala Ser Ser Ala Ser Ser Pro Gly Ser Gly Ile
            180                 185                 190

Ser Glu Ala Leu Arg Ala Gly Ala Gly Ser Gly Thr Gly Tyr Asn Lys
    195                 200                 205

Glu Phe Leu Leu Tyr Leu Ala Gly Phe Val Asp Gly Asp Gly Ser Ile
    210                 215                 220

Ile Ala Gln Ile Lys Pro Gly Gln Ser Tyr Lys Phe Lys His Thr Leu
225                 230                 235                 240

Gln Leu Val Phe Gln Val Thr Gln Lys Thr Gln Arg Arg Trp Phe Leu
            245                 250                 255

Asp Lys Leu Val Asp Glu Ile Gly Val Gly Tyr Val Ile Asp Arg Gly
            260                 265                 270

Ser Ala Ser Asp Tyr Arg Leu Ser Glu Ile Lys Pro Leu His Asn Phe
    275                 280                 285

Leu Thr Gln Leu Gln Pro Phe Leu Lys Leu Lys Gln Lys Gln Ala Asn
    290                 295                 300

Leu Val Leu Lys Ile Ile Glu Gln Leu Pro Ser Ala Lys Glu Ser Pro
305                 310                 315                 320

Asp Lys Phe Leu Glu Val Cys Thr Trp Val Asp Gln Ile Ala Ala Leu
            325                 330                 335

Asn Asp Ser Lys Thr Arg Lys Thr Thr Ser Glu Thr Val Arg Ala Val
            340                 345                 350

Leu Asp Ser Leu Ser Glu Lys Lys Lys Ser Ser Pro
    355                 360

<210> SEQ ID NO 10
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Pro Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Ile Ala Gln Ile Pro Pro Asn Gln Ser Cys Lys Phe Lys His Gln
            35                  40                  45

Leu Arg Leu Thr Phe Gln Val Thr Gln Lys Thr Gln Arg Arg Trp Phe
    50                  55                  60

Leu Asp Lys Leu Val Asp Glu Ile Gly Val Gly Tyr Val Arg Asp Arg
65                  70                  75                  80

Gly Ser Val Ser Asp Tyr Ile Leu Ser Glu Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
```

```
                145                 150                 155                 160
Val Leu Asp Ser Leu Pro Gly Ser Val Gly Gly Leu Ser Pro Ser Gln
                165                 170                 175

Ala Ser Ser Ala Ala Ser Ser Ala Ser Ser Pro Gly Ser Gly Ile
                180                 185                 190

Ser Glu Ala Leu Arg Ala Gly Ala Gly Ser Gly Thr Gly Tyr Asn Lys
                195                 200                 205

Glu Phe Leu Leu Tyr Leu Ala Gly Phe Val Asp Gly Asp Gly Ser Ile
                210                 215                 220

Tyr Ala Gly Ile Ala Pro Asn Gln Ser Cys Lys Phe Lys His Gln Leu
225                 230                 235                 240

Arg Leu Trp Phe Val Val Ser Gln Lys Thr Gln Arg Arg Trp Phe Leu
                245                 250                 255

Asp Lys Leu Val Asp Glu Ile Gly Val Gly Tyr Val Ile Asp Asn Gly
                260                 265                 270

Ser Val Ser His Tyr Arg Leu Ser Glu Ile Lys Pro Leu His Asn Phe
                275                 280                 285

Leu Thr Gln Leu Gln Pro Phe Leu Lys Leu Lys Gln Lys Gln Ala Asn
                290                 295                 300

Leu Val Leu Lys Ile Ile Glu Gln Leu Pro Ser Ala Lys Glu Ser Pro
305                 310                 315                 320

Asp Lys Phe Leu Glu Val Cys Thr Trp Val Asp Gln Ile Ala Ala Leu
                325                 330                 335

Asn Asp Ser Lys Thr Arg Lys Thr Thr Ser Glu Thr Val Arg Ala Val
                340                 345                 350

Leu Asp Ser Leu Ser Glu Lys Lys Ser Ser Pro
                355                 360

<210> SEQ ID NO 11
<211> LENGTH: 3663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccagaaac     420
ctttcaacca gcttttgagc taatgataga gagaagctca aggaattgga gcaatgcttg     480
actagggatg tcagagggag gctatccaga ggagcttaca actgaggtaa acttaaaagt     540
tagggagttt gtcaacttca acccacagaa tagagcagag ccaggaggag ctgaggcttc     600
tgagtgttat ggtggaagca tcaccccaac ccttgacatc catatgcctg aagagtctgg     660
aatgttatgg tggaagttcc acccaagcct cccttcccgg tcgccctcca aaccctgcta     720
catctcagaa atcccaccaa atgatgactc cctcccccag agatattcaa gaccactccc     780
acagggtatt taaactgccc cccaaccccc agaaaataga tgtgtggttt tccaatctct     840
```

```
ctttcctatc acgtctctgg ggagctggca ggccatttgg gagcattgta tccattaaac      900
gacttctcag tggagactct gaaagccaga agagcctaga cagatagatg tcttgcgaat      960
tcttgcatac tctagagact acagatgccg gcccagacta ttatatccag caaaagtttc     1020
aaacaccata caaagtcaaa tttaaacagt atctatctac aaatccaata ttacagaagg     1080
tgctagtagg aaaactccaa actaagatta actatacctg tgaagacaca ggaaataatc     1140
tcacactggc aaaagaagaa aaacctctct ctctctctcc tctctctctc tctctctctc     1200
tctctctctc tctctctctc tctctctctc tcacacacac acacacacac acacacacac     1260
accaacacca ataccatgaa caacaaaata acaggaatta acaataattg atgtgtgtgt     1320
atgtccctgt gtgtgtgtcc ttgtgtgtgt ctgtttgtgt gtctgtgtat atgtttgtca     1380
cctgaggggt ggctcttcct tggtttgtga ggtttctacc caaaagcttg gcgtaatcat     1440
ggtcatagct gtttcctgtg tgaaattgtt atccgctcac aattccacac aacatacgag     1500
ccggaagcat aaagtgtaaa gcctggggtg cctaatgagt gagctaactc acattaattg     1560
cgttgcgctc actgcccgct ttccagtcgg gaaacctgtc gtgccagctg cattaatgaa     1620
tcggccaacg cgcggggaga ggcggtttgc gtattgggcg ctcttccgct tcctcgctca     1680
ctgactcgct gcgctcggtc gttcggctgc ggcgagcggt atcagctcac tcaaaggcgg     1740
taatacggtt atccacagaa tcaggggata acgcaggaaa gaacatgtga gcaaaaggcc     1800
agcaaaaggc caggaaccgt aaaaaggccg cgttgctggc gtttttccat aggctccgcc     1860
cccctgacga gcatcacaaa aatcgacgct caagtcagag gtggcgaaac ccgacaggac     1920
tataaagata ccaggcgttt ccccctggaa gctccctcgt gcgctctcct gttccgaccc     1980
tgccgcttac cggatacctg tccgcctttc tcccttcggg aagcgtggcg ctttctcata     2040
gctcacgctg taggtatctc agttcggtgt aggtcgttcg ctccaagctg ggctgtgtgc     2100
acgaaccccc cgttcagccc gaccgctgcg ccttatccgg taactatcgt cttgagtcca     2160
acccggtaag acacgactta tcgccactgg cagcagccac tggtaacagg attagcagag     2220
cgaggtatgt aggcggtgct acagagttct tgaagtggtg gcctaactac ggctacacta     2280
gaagaacagt atttggtatc tgcgctctgc tgaagccagt taccttcgga aaaagagttg     2340
gtagctcttg atccggcaaa caaaccaccg ctggtagcgg tggtttttttt gtttgcaagc     2400
agcagattac gcgcagaaaa aaaggatctc aagaagatcc tttgatcttt tctacggggt     2460
ctgacgctca gtggaacgaa aactcacgtt aagggatttt ggtcatgaga ttatcaaaaa     2520
ggatcttcac ctagatcctt ttaaattaaa aatgaagttt taaatcaatc taagtatat      2580
atgagtaaac ttggtctgac agttaccaat gcttaatcag tgaggcacct atctcagcga     2640
tctgtctatt tcgttcatcc atagttgcct gactccccgt cgtgtagata actacgatac     2700
gggagggctt accatctggc cccagtgctg caatgatacc gcgagaccca cgctcaccgg     2760
ctccagattt atcagcaata aaccagccag ccggaagggc cgagcgcaga agtggtcctg     2820
caactttatc cgcctccatc cagtctatta attgttgccg ggaagctaga gtaagtagtt     2880
cgccagttaa tagtttgcgc aacgttgttg ccattgctac aggcatcgtg gtgtcacgct     2940
cgtcgtttgg tatggcttca ttcagctccg gttcccaacg atcaaggcga gttacatgat     3000
cccccatgtt gtgcaaaaaa gcggttagct ccttcggtcc tccgatcgtt gtcagaagta     3060
agttggccgc agtgttatca ctcatggtta tggcagcact gcataattct cttactgtca     3120
tgccatccgt aagatgcttt tctgtgactg gtgagtactc aaccaagtca ttctgagaat     3180
```

```
agtgtatgcg gcgaccgagt tgctcttgcc cggcgtcaat acgggataat accgcgccac    3240
atagcagaac tttaaaagtg ctcatcattg gaaaacgttc ttcggggcga aaactctcaa    3300
ggatcttacc gctgttgaga tccagttcga tgtaacccac tcgtgcaccc aactgatctt    3360
cagcatcttt tactttcacc agcgtttctg ggtgagcaaa aacaggaagg caaaatgccg    3420 caaaaaggg aataagggcg acacggaaat gttgaatact catactcttc cttttcaat    3480 attattgaag catttatcag ggttattgtc tcatgagcgg atacatattt gaatgtattt    3540
agaaaaataa acaaataggg gttccgcgca catttccccg aaaagtgcca cctgacgtct    3600
aagaaaccat tattatcatg acattaacct ataaaaatag gcgtatcacg aggccctttc    3660
gtc                                                                  3663
```

<210> SEQ ID NO 12
<211> LENGTH: 22
<212> TYPE: DNA
<213> ORGANISM: Cricetulus griseus

<400> SEQUENCE: 12

```
tacatgtatg tacaaaatat at                                               22
```

<210> SEQ ID NO 13
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Ala Pro Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
            20                  25                  30

Ile Phe Ala Ser Ile Thr Pro Arg Gln Cys Tyr Lys Phe Lys His Glu
        35                  40                  45

Leu Gln Leu Thr Phe Val Val Thr Gln Lys Thr Gln Arg Arg Trp Phe
    50                  55                  60

Leu Asp Lys Leu Val Asp Glu Ile Gly Val Gly Tyr Val Ile Asp Gln
65                  70                  75                  80

Gly Ser Val Ser His Tyr Arg Leu Ser Glu Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                165                 170                 175

Ala Ser Ser Ala Ala Ser Ser Ala Ser Ser Pro Gly Ser Gly Ile
            180                 185                 190

Ser Glu Ala Leu Arg Ala Gly Ala Gly Ser Gly Thr Gly Tyr Asn Lys
        195                 200                 205

Glu Phe Leu Leu Tyr Leu Ala Gly Phe Val Asp Gly Asp Gly Ser Ile
```

```
                    210                 215                 220
Ile Ala Gln Ile Lys Pro Asn Gln Ser Cys Lys Phe Lys His Gln Leu
225                 230                 235                 240

Met Leu Thr Phe Thr Val Ala Gln Lys Thr Gln Arg Arg Trp Phe Leu
                245                 250                 255

Asp Lys Leu Val Asp Glu Ile Gly Val Gly Tyr Val Ile Asp Ile Gly
                260                 265                 270

Ser Val Ser Glu Tyr Arg Leu Ser Gln Ile Lys Pro Leu His Asn Phe
                275                 280                 285

Leu Thr Gln Leu Gln Pro Phe Leu Lys Leu Lys Gln Lys Gln Ala Asn
                290                 295                 300

Leu Val Leu Lys Ile Ile Glu Gln Leu Pro Ser Ala Lys Glu Ser Pro
305                 310                 315                 320

Asp Lys Phe Leu Glu Val Cys Thr Trp Val Asp Gln Ile Ala Ala Leu
                325                 330                 335

Asn Asp Ser Lys Thr Arg Lys Thr Thr Ser Glu Thr Val Arg Ala Val
                340                 345                 350

Leu Asp Ser Leu Ser Glu Lys Lys Ser Ser Pro
                355                 360

<210> SEQ ID NO 14
<211> LENGTH: 22
<212> TYPE: DNA
<213> ORGANISM: Cricetulus griseus

<400> SEQUENCE: 14
aaggcactcg tgtaaacgga ta                                              22

<210> SEQ ID NO 15
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Pro Lys Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Lys Ala Ile Ile Arg Pro Glu Gln Ser Tyr Lys Phe Lys His Arg
            35                  40                  45

Leu Arg Leu Val Phe Gln Val Thr Gln Lys Thr Gln Arg Arg Trp Phe
        50                  55                  60

Leu Asp Lys Leu Val Asp Glu Ile Gly Val Gly Tyr Val Tyr Asp Arg
65                  70                  75                  80

Gly Ser Val Ser Asp Tyr Tyr Leu Ser Glu Ile Lys Pro Leu His Asn
                85                  90                  95

Phe Leu Thr Gln Leu Gln Pro Phe Leu Lys Leu Lys Gln Lys Gln Ala
                100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
        130                 135                 140

Leu Asn Asp Ser Lys Thr Arg Lys Thr Thr Ser Glu Thr Val Arg Ala
145                 150                 155                 160
```

```
Val Leu Asp Ser Leu Pro Gly Ser Val Gly Gly Leu Ser Pro Ser Gln
                165                 170                 175

Ala Ser Ser Ala Ala Ser Ser Ala Ser Ser Pro Gly Ser Gly Ile
            180                 185                 190

Ser Glu Ala Leu Arg Ala Gly Ala Gly Ser Gly Thr Gly Tyr Asn Lys
        195                 200                 205

Glu Phe Leu Leu Tyr Leu Ala Gly Phe Val Asp Gly Asp Gly Ser Ile
    210                 215                 220

Trp Ala Arg Ile Lys Pro Gly Gln Ser Tyr Lys Phe Lys His Thr Leu
225                 230                 235                 240

Glu Leu Val Phe Gln Val Thr Gln Lys Thr Gln Arg Arg Trp Ile Leu
                245                 250                 255

Asp Lys Leu Val Asp Glu Ile Gly Val Gly Tyr Val Thr Asp Ala Gly
            260                 265                 270

Ser Ala Ser Val Tyr Arg Leu Ser Glu Ile Lys Pro Leu His Asn Phe
        275                 280                 285

Leu Thr Gln Leu Gln Pro Phe Leu Lys Leu Lys Gln Lys Gln Ala Asn
    290                 295                 300

Leu Val Leu Lys Ile Ile Glu Gln Leu Pro Ser Ala Lys Glu Ser Pro
305                 310                 315                 320

Asp Lys Phe Leu Glu Val Cys Thr Trp Val Asp Gln Ile Ala Ala Leu
                325                 330                 335

Asn Asp Ser Lys Thr Arg Lys Thr Thr Ser Glu Thr Val Arg Ala Val
            340                 345                 350

Leu Asp Ser Leu Ser Glu Lys Lys Lys Ser Ser Pro
    355                 360

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagggacat taatctgcat gcagtgatc                                    29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcttggttt gggttgtcta agcaacctc                                    29

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacaggtgtc cactcccagt tcaattacag ctcttaagg                         39
```

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
cgatggccca ctacgtgaac catcacc                                              27

<210> SEQ ID NO 20
<211> LENGTH: 1821
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
cacaggtgtc cactcccagt tcaattacag ctcttaaggc tagagtactt aatacgactc      60
actataggct agcctcgagc cgccaccatg gcaccgaaga agaagcgcaa ggtgcatatg     120
gcaccgaaga agaagcgcaa ggtgcatatg aacaccaagt acaacaagga gttcctgctc     180
tacctggcgg gcttcgtcga cggggacggc tccatcaagg cccagatctt ccgaaccag      240 tgctacaagt tcaagcatca gctgaggctc cgtttccagg tcacccagaa gacacagcgc     300
cgttggttcc tcgacaagct ggtggacgag atcggggtgg gctacgtgac tgaccgcggc     360
agcgtctccg actacatgct gagccagatc aagcctctgc acaacttcct gacccagctc     420
cagcccttcc tgaagctcaa gcagaagcag gccaacctcg tgctgaagat catcgagcag     480 ctgcctccg ccaaggaatc cccggacaag ttcctggagg tgtgcacgtg ggtggaccag      540
atcgcggccc tcaacgacag caagacccgc aagacgacct cggagacggt gcgggcggtc     600
ctggactccc tcccaggatc cgtgggaggt ctatcgccat tcaggcatc cagcgccgca     660 tcctcggctt cctcaagccc gggttcaggg atctccgaag cactcagagc tggagcaggt     720
tccggcactg gatacaacaa ggaattcctg ctctacctgg cgggcttcgt ggacggggac     780
ggctccatca tcgcccagat caagccgggt cagtcctaca gttcaagca taccctgcag      840 ctcgtttttcc aggtcacgca gaagacacag cgccgttgga tcctcgacaa gctggtggac     900
gagatcgggg tgggctatgt gatcgaccgc ggcagcgcct ccgactaccg cctgagcgag     960
atcaagcctc tgcacaactt cctgacccag ctccagccct tcctgaagct caagcagaag    1020
caggccaacc tcgtgctgaa gatcatcgag cagctgccct ccgccaagga atccccggac    1080
aagttcctgg aggtgtgcac ctgggtggac cagatcgccg ctctgaacga ctccaagacc    1140
cgcaagacca cttccgagac cgtccgcgcc gttctagaca gtctctccga agaagaag     1200 tcgtccccct agacagtctc tccgagaaga gaagtcgtc ccctagcgg ccgcttcgag      1260 cagacatgat aagatacatt gatgagtttg gacaaaccac aactagaatg cagtgaaaaa    1320
aatgctttat ttgtgaaatt tgtgatgcta ttgctttatt tgtaaccatt ataagctgca    1380
ataaacaagt taacaacaac aattgcattc atttttatgtt tcaggttcag ggggagatgt    1440
gggaggtttt ttaaagcaag taaaacctct acaaatgtgg taaaatcgat aagatcttga    1500
tccgggctgg cgtaatagcg aagaggcccg caccgatcgc ccttcccaac agttgcgcag    1560
cctgaatggc gaatgacgc gccctgtagc ggcgcattaa gcgcggcggg tgtggtggtt    1620
acgcgcagcg tgaccgctac acttgccagc gccctagcgc ccgctccttt cgctttcttc    1680
```

```
ccttcctttc tcgccacgtt cgccggcttt ccccgtcaag ctctaaatcg ggggctccct   1740
ttagggttcc gatttagtgc tttacggcac ctcgacccca aaaaacttga ttagggtgat   1800
ggttcacgta gtgggccatc g                                             1821
```

<210> SEQ ID NO 21
<211> LENGTH: 1821
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
cacaggtgtc cactcccagt tcaattacag ctcttaaggc tagagtactt aatacgactc     60
actataggct agcctcgagc cgccaccatg gcaccgaaga agaagcgcaa ggtgcatatg    120
gcaccgaaga agaagcgcaa ggtgcatatg aacaccaagt acaacaagga gttcctgctc    180
tacctggcgg gcttcgtgga cggggacggc tccatcatcg cccagatccc gccgaaccag    240
tcctgcaagt tcaagcatca gctgcgcctc accttccagg tcacgcagaa gacacagcgc    300
cgttggttcc tcgacaagct ggtggacgag atcggggtgg gctacgtgcg cgaccgcggc    360
agcgtctccg actacatcct gagcgagatc aagcctctgc acaacttcct gacccagctc    420
cagcccttcc tgaagctcaa gcagaagcag gccaacctcg tgctgaagat catcgagcag    480 ctgcccctccg ccaaggaatc cccggacaag ttcctggagg tgtgcacctg ggtggaccag    540
atcgccgctc tgaacgactc caagacccgc aagaccactt ccgagactgt ccgcgccgtt    600
ctagacagtc tcccaggatc cgtgggaggt ctatcgccat ctcaggcatc cagcgccgca    660
tcctcggctt cctcaagccc gggttcaggg atctccgaag cactcagagc tggagcaggt    720
tccggcactg gatacaacaa ggaattcctg ctctacctgg cgggcttcgt ggacggggac    780
ggctccatct acgccgggat cgcgccgaac cagtcctgca gttcaagca tcagctgcgc    840 ctctggttcg tggtcagcca aagacacag cgccgttggt tcctcgacaa gctggtggac    900
gagatcgggg tgggctacgt gattgacaat ggcagcgtct cccattaccg cctgagcgag    960
atcaagcctc tgcacaactt cctgacccag ctccagcct tcctgaagct caagcagaag   1020
caggccaacc tcgtgctgaa gatcatcgag cagctgccct ccgccaagga atccccggac   1080
aagttcctgg aggtgtgcac ctgggtggac cagatcgccg ctttgaacga ctccaagacc   1140
cgcaagacca cttccgagac tgtccgcgcc gttctagaca gtctctccga agaagaag   1200 tcgtccccct agacagtctc tccgagaaga agaagtcgtc cccctagcgg ccgcttcgag   1260
cagacatgat aagatacatt gatgagtttg gacaaaccac aactagaatg cagtgaaaaa   1320
aatgctttat ttgtgaaatt tgtgatgcta ttgctttatt tgtaaccatt ataagctgca   1380
ataaacaagt taacaacaac aattgcattc atttttatgtt tcaggttcag ggggagatgt   1440
gggaggtttt ttaaagcaag taaaacctct acaaatgtgg taaaatcgat aagatcttga   1500
tccgggctgg cgtaatagcg aagaggcccg caccgatcgc ccttcccaac agttgcgcag   1560
cctgaatggc gaatggacgc gccctgtagc ggcgcattaa gcgcggcggg tgtggtggtt   1620
acgcgcagcg tgaccgctac acttgccagc gccctagcgc ccgctccttt cgctttcttc   1680
ccttcctttc tcgccacgtt cgccggcttt ccccgtcaag ctctaaatcg ggggctccct   1740
ttagggttcc gatttagtgc tttacggcac ctcgacccca aaaaacttga ttagggtgat   1800
ggttcacgta gtgggccatc g                                             1821
```

<210> SEQ ID NO 22
<211> LENGTH: 1821
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

| | | | | | |
|---|---|---|---|---|---|
| cacaggtgtc | cactcccagt | tcaattacag | ctcttaaggc | tagagtactt | aatacgactc | 60 |
| actataggct | agcctcgagc | cgccaccatg | gcaccgaaga | agaagcgcaa | ggtgcatatg | 120 |
| gcaccgaaga | agaagcgcaa | ggtgcatatg | aacaccaagt | acaacaagga | gttcctgctc | 180 |
| tacctggcgg | gcttcgtcga | cggggacggc | tccatcaagg | ccattatccg | gccagagcag | 240 |
| tcctacaagt | tcaagcatcg | cctgcggctc | gtttccagg | tcacgcagaa | gacacagcgc | 300 |
| cgttggttcc | tcgacaagct | ggtggacgag | atcggggtgg | gctacgtgta | cgaccgcggc | 360 |
| agcgtctccg | actactatct | gagcgagatc | aagcctctgc | acaacttcct | gacccagctc | 420 |
| cagcccttcc | tgaagctcaa | gcagaagcag | gccaacctcg | tgctgaagat | catcgagcag | 480 |
| ctgccctccg | ccaaggaatc | cccggacaag | ttcctggagg | tgtgcacgtg | ggtggaccag | 540 |
| atcgcggccc | tcaacgacag | caagacccgc | aagacgacct | cggagacggt | gcgagcggtc | 600 |
| ctggactccc | tcccaggatc | cgtgggaggt | ctatcgccat | tcaggcatc | cagcgccgca | 660 |
| tcctcggctt | cctcaagccc | gggttcaggg | atctccgaag | cactcagagc | tggagcaggt | 720 |
| tccggcactg | gatacaacaa | ggaattcctg | ctctacctgg | cgggcttcgt | ggacggggac | 780 |
| ggctccatct | gggcccggat | caagccgggg | cagtcctaca | agttcaagca | taccctggag | 840 |
| ctcgtgttcc | aggtcaccca | gaagacacag | cgccgttgga | tcctcgacaa | gctggtggac | 900 |
| gagatcgggg | tgggctacgt | gaccgacgcc | ggcagcgcct | ccgtctaccg | cctgagcgag | 960 |
| atcaagcctc | tgcacaactt | cctgacccag | ctccagcccct | tcctgaagct | caagcagaag | 1020 |
| caggccaacc | tcgtgctgaa | gatcatcgag | cagctgccct | ccgccaagga | atccccggac | 1080 |
| aagttcctgg | aggtgtgcac | ctgggtggac | cagatcgccg | ctctgaacga | ctccaagacc | 1140 |
| cgcaagacca | cttccgagac | cgtccgcgcc | gttctagaca | gtctctccga | agaagaag | 1200 |
| tcgtcccct | agacagtctc | tccgagaaga | agaagtcgtc | ccctagcgg | ccgcttcgag | 1260 |
| cagacatgat | aagatacatt | gatgagtttg | gacaaaccac | aactagaatg | cagtgaaaaa | 1320 |
| aatgctttat | ttgtgaaatt | tgtgatgcta | ttgctttatt | tgtaaccatt | ataagctgca | 1380 |
| ataaacaagt | taacaacaac | aattgcattc | attttatgtt | tcaggttcag | ggggagatgt | 1440 |
| gggaggtttt | ttaaagcaag | taaaacctct | acaaatgtgg | taaaatcgat | aagatcttga | 1500 |
| tccgggctgg | cgtaatagcg | aagaggcccg | caccgatcgc | ccttcccaac | agttgcgcag | 1560 |
| cctgaatggc | gaatggacgc | gccctgtagc | ggcgcattaa | gcgcggcggg | tgtggtggtt | 1620 |
| acgcgcagcg | tgaccgctac | acttgccagc | gccctagcgc | ccgctccttt | cgctttcttc | 1680 |
| ccttcctttc | tcgccacgtt | cgccggcttt | ccccgtcaag | ctctaaatcg | ggggctccct | 1740 |
| ttagggttcc | gatttagtgc | tttacggcac | ctcgacccca | aaaaacttga | ttagggtgat | 1800 |
| ggttcacgta | gtgggccatc | g | | | | 1821 |

<210> SEQ ID NO 23
<211> LENGTH: 34
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 23
tgacagctct ggccttaagt gcctacgaaa ctag                                   34

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtctttcctc tttgctgtag ccttggtaga actactgcc                              39

<210> SEQ ID NO 25
<211> LENGTH: 5653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt ccatacccag gggagctgta      420
ctgggctgca gccctgcgcc attcagccat gcaccaggct actccctcct cttccagctt      480
tctccttctg atggccatag gattagaaga taagggactc tagtgcaggt caactgctga      540
ccagtgtgaa aatgcacaga ctacatgctg gtagatcagc acttcaaact actgttcacc      600
atcatctctg gaataagcac tacatttaca gggttcaaac ctcaatgaat ataaacaaac      660
aaaacacacc tcccttcctt cactgtctcc catttctttg gttcccatct ccacatagaa      720
tttataatta aaatttctaa gtatctttcc agaaatactt cacacatgtt ataagcaaat      780
gtgcttttaa agatactatt ttaaattatg aaaatggtta tattagttga gataaaagaa      840
tagaatggga agttccagaa tttaaggcct catatggatc ccagctgtgg aatgtgtgtc      900
agttagggtg tggaaagtcc ccaggctccc cagcaggcag aagtatgcaa agcatgcatc      960
tcaattagtc agcaaccagg tgtggaaagt cccaggctc cccagcaggc agaagtatgc      1020
aaagcatgca tctcaattag tcagcaacca tagtcccgcc cctaactccg cccatcccgc      1080
ccctaactcc gcccagttcc gcccattctc cgccccatgg ctgactaatt tttttattt      1140 atgcagaggc cgaggccgcc tcggcctctg agctattcca gaagtagtga ggaggctttt      1200
ttggaggcta ccatggagaa gttactattc cgaagttcct attctctaga agtatagga      1260 acttcaagct tggcactggg taccgccaag ttgaccagtg ccgttccggt gctcaccgcg      1320
cgcgacgtcg ccggagcggt cgagttctgg accgaccggc tcgggttctc ccggacttc      1380 gtggaggacg acttcgccgg tgtggtccgg gacgacgtga ccctgttcat cagcgcggtc      1440
```

```
caggaccagg tggtgccgga caacaccctg gcctgggtgt gggtgcgcgg cctggacgag    1500
ctgtacgccg agtggtcgga ggtcgtgtcc acgaacttcc gggacgcctc cgggccggcc    1560
atgaccgaga tcggcgagca gccgtggggg cgggagttcg ccctgcgcga cccggccggc    1620
aactgcgtgc acttcgtggc cgaggagcag gactgacacc cgagcgaaaa cggtctgcgc    1680
tgcgggacgc gcgaattgaa ttatggccca caccagtggc gcggcgactt ccagttcaac    1740
atcagccgct acagtcaaca gcaactgatg gaaaccagcc atcgccatct gctgcacgcg    1800
gaagaaggca catggctgaa tatcgacggt tccatatgg ggattggtgg cgacgactcc     1860
tggagcccgt cagtatcggc ggaattccag ctgagcgccg tcgctacca ttaccagttg     1920 gtctggtgtc aaaaataata ataaccgggc agggggatc tgcatggatc tttgtgaagg     1980
aaccttactt ctgtggtgtg acataattgg acaaactacc tacagagatt aaagctcta     2040 aggtaaatat aaaattttta agtgtataat gtgttaaact actgattcta attgtttgtg    2100
tattttagat tccaacctat ggaactgatg aatgggagca gtggtggaat gcctttaatg    2160
aggaaaacct gttttgctca gaagaaatgc catctagtga tgatgaggct actgctgact    2220
ctcaacattc tactcctcca aaaagaaga gaaaggtaga agaccccaag gactttcctt      2280
cagaattgct aagttttttg agtcatgctg tgtttagtaa tagaactctt gcttgctttg    2340
ctatttacac cacaaaggaa aaagctgcac tgctatacaa gaaaattatg gaaaaatatt    2400
ctgtaacctt tataagtagg cataacagtt ataatcataa catactgttt tttcttactc    2460
cacacaggca tagagtgtct gctattaata actatgctca aaaattgtgt acctttagct    2520
ttttaatttg taaaggggtt aataaggaat atttgatgta tagtgccttg actagagatc    2580
ataatcagcc ataccacatt tgtagaggtt ttacttgctt taaaaaacct cccacacctc    2640
cccctgaacc tgaaacataa aatgaatgca attgttgttg ttaacttgtt tattgcagct    2700
tataatggtt acaataaag caatagcatc acaaatttca caaataaagc attttttca     2760 ctgcattcta gttgtggttt gtccaaactc atcaatgtat cttatcatgt ctggatcccc    2820
aggaagctcc tctgtgtcct cataaaccct aacctcctct acttgagagg acattccaat    2880
cataggctgc ccatccaccc tactagtata tgaaaatata aagcgctttc tcttttaagt    2940
ctagggtagg tgtactagat cagcgctcag ctccatacca tgaagccatc caggagtcag    3000
acctctctga cagccctgcc attgtcacag agaagtttct gtcaccagtg ctcatgctgt    3060
cagaggagcg aaggagaaaa gatgtgagac ctcccaagtc aaagtcatct atggataaaa    3120
ccttagttgc atggcacacc agtgttaggg agtcggggaa acacagccat agcccagctt    3180
cctctctgtt cttgctctta ttaccaccag aaagaggttg cttagacaac ccaaaccaag    3240
acacagggct ctgtgggagg gaatcagtcc caggcttctg gcacatgcta tgtcaccgga    3300
aagccccagc cctactccga atccccacaa gtacagcaaa tatcagatta tagcatttaa    3360
aggggcactc ttgccaaaga gaagcaccat tggaatagcc atgcttgaga actaagcttg    3420
gcgtaatcat ggtcatagct gtttcctgtg tgaaattgtt atccgctcac aattccacac    3480
aacatacgag ccggaagcat aaagtgtaaa gcctggggtg cctaatgagt gagctaactc    3540
acattaattg cgttgcgctc actgcccgct ttccagtcgg gaaacctgtc gtgccagctg    3600
cattaatgaa tcggccaacg cgcggggaga ggcggtttgc gtattgggcg ctcttccgct    3660
tcctcgctca ctgactcgct gcgctcggtc gttcggctgc ggcgagcggt atcagctcac    3720
tcaaaggcgg taatacggtt atccacagaa tcaggggata acgcaggaaa gaacatgtga    3780
```

```
gcaaaaggcc agcaaaaggc caggaaccgt aaaaaggccg cgttgctggc gttttteccat     3840
aggctccgcc ccectgacga gcatcacaaa atcgacgct caagtcagag gtggcgaaac      3900
ccgacaggac tataaagata ccaggcgttt ccccctggaa gctccctcgt gcgctctcct    3960
gttccgaccc tgccgcttac cggatacctg tccgcctttc tcccttcggg aagcgtggcg   4020
ctttctcata gctcacgctg taggtatctc agttcggtgt aggtcgttcg ctccaagctg    4080
ggctgtgtgc acgaaccccc cgttcagccc gaccgctgcg ccttatccgg taactatcgt   4140
cttgagtcca acccggtaag acacgactta tcgccactgg cagcagccac tggtaacagg   4200
attagcagag cgaggtatgt aggcggtgct acagagttct tgaagtggtg cctaactac    4260
ggctacacta agaacagt atttggtatc tgcgctctgc tgaagccagt taccttcgga    4320
aaaagagttg gtagctcttg atccggcaaa caaccaccg ctggtagcgg tggttttttt   4380
gtttgcaagc agcagattac gcgcagaaaa aaggatctc aagaagatcc tttgatcttt   4440
tctacggggt ctgacgctca gtggaacgaa aactcacgtt aagggatttt ggtcatgaga  4500
ttatcaaaaa ggatcttcac ctagatcctt ttaaattaaa aatgaagttt taaatcaatc  4560
taaagtatat atgagtaaac ttggtctgac agttaccaat gcttaatcag tgaggcacct   4620
atctcagcga tctgtctatt tcgttcatcc atagttgcct gactccccgt cgtgtagata   4680
actacgatac gggagggctt accatctggc cccagtgctg caatgatacc gcgagaccca   4740
cgctcaccgg ctccagattt atcagcaata accagccag ccggaagggc cgagcgcaga   4800
agtggtcctg caactttatc cgcctccatc cagtctatta attgttgccg ggaagctaga  4860
gtaagtagtt cgccagttaa tagtttgcgc aacgttgttg ccattgctac aggcatcgtg  4920
gtgtcacgct cgtcgtttgg tatggcttca ttcagctccg gttcccaacg atcaaggcga  4980
gttacatgat cccccatgtt gtgcaaaaaa gcggttagct ccttcggtcc tccgatcgtt   5040
gtcagaagta agttggccgc agtgttatca ctcatggtta tggcagcact gcataattct   5100
cttactgtca tgccatccgt aagatgcttt tctgtgactg gtgagtactc aaccaagtca    5160
ttctgagaat agtgtatgcg gcgaccgagt tgctcttgcc cggcgtcaat acgggataat   5220
accgcgccac atagcagaac tttaaaagtg ctcatcattg gaaaacgttc ttcggggcga   5280
aaactctcaa ggatcttacc gctgttgaga tccagttcga tgtaacccac tcgtgcaccc  5340
aactgatctt cagcatcttt tactttcacc agcgtttctg ggtgagcaaa aacaggaagg   5400
caaaatgccg caaaaaggg aataagggcg acacggaaat gttgaatact catactcttc   5460
cttttcaat attattgaag catttatcag ggttattgtc tcatgagcgg atacatattt    5520
gaatgtattt agaaaaataa acaaataggg gttccgcgca catttccccg aaaagtgcca   5580
cctgacgtct aagaaaccat tattatcatg acattaacct ataaaaatag gcgtatcacg   5640
aggccctttc gtc                                                        5653
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 26
agatgcatgc tttgcatact tctgcctgc                                       29

<210> SEQ ID NO 27

<211> LENGTH: 5785
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttagcc accatggtga gcaagggcga ggagctgttc accggggtgg | 960 |
| tgcccatcct ggtcgagctg gacggcgacg taaacggcca caagttcagc gtgtccggcg | 1020 |
| agggcgaggg cgatgccacc tacggcaagc tgaccctgaa gttcatctgc accaccggca | 1080 |
| agctgcccgt gccctggccc accctcgtga ccaccctgac ctacggagtg cagtgcttca | 1140 |
| gccgctaccc cgaccacatg aagcagcacg acttcttcaa gtccgccatg cccgaaggct | 1200 |
| acgtccagga gcgcaccatc ttcttcaagg acgacggcaa ctacaagacc cgcgccgagg | 1260 |
| tgaagttcga gggcgacacc ctggtgaacc gcatcgagct gaagggcatc gacttcaagg | 1320 |
| aggacggcaa catcctgggg cacaagctgg agtacaacta caacagccac aacgtctata | 1380 |
| tcatggccga caagcagaag aacggcatca aggtgaactt caagatccgc cacaacatcg | 1440 |
| aggacggcag cgtgcagctc gccgaccact accagcagaa cacccccatc ggcgacggcc | 1500 |
| ccgtgctgct gcccgacaac cactacctga gcacccagtc cgccctgagc aaagacccca | 1560 |
| acgagaagcg cgatcacatg gtcctgctgg agttcgtgac cgccgccggg atcactctcg | 1620 |
| gcatggacga gctgtacaag taaggatcca ctagtccagt gtggtggaat tctgcagata | 1680 |
| tccagcacag tggcggccgc tcgagtctag agggcccgtt taaacccgct gatcagcctc | 1740 |
| gactgtgcct tctagttgcc agccatctgt tgtttgcccc tcccccgtgc cttccttgac | 1800 |
| cctggaaggt gccactccca ctgtcctttc ctaataaaat gaggaaattg catcgcattg | 1860 |
| tctgagtagg tgtcattcta ttctgggggg tggggtgggg caggacagca agggggagga | 1920 |
| ttgggaagac aatagcaggc atgctgggga tgcggtgggc tctatggctt ctgaggcgga | 1980 |
| aagaaccagc tggggctcta gggggtatcc ccacgcgccc tgtagcggcg cattaagcgc | 2040 |
| ggcgggtgtg gtggttacgc gcagcgtgac cgctacactt gccagcgccc tagcgcccgc | 2100 |

```
tcctttcgct ttcttcccttc ctttctcgc cacgttcgcc ggctttcccc gtcaagctct    2160
aaatcggggg ctcccttag ggttccgatt tagtgcttta cggcacctcg accccaaaaa    2220
acttgattag ggtgatggtt cacgtaccta gaagttccta ttccgaagtt cctattctct    2280
agaaagtata ggaacttcct tggccaaaaa gcctgaactc accgcgacgt ctgtcgagaa    2340
gtttctgatc gaaaagttcg acagcgtctc cgacctgatg cagctctcgg agggcgaaga    2400
atctcgtgct ttcagcttcg atgtaggagg gcgtggatat gtcctgcggg taaatagctg    2460
cgccgatggt ttctacaaag atcgttatgt ttatcggcac tttgcatcgg ccgcgctccc    2520
gattccggaa gtgcttgaca ttggggaatt cagcgagagc ctgacctatt gcatctcccg    2580
ccgtgcacag ggtgtcacgt tgcaagacct gcctgaaacc gaactgcccg ctgttctgca    2640
gccggtcgcg gaggccatgg atgcgatcgc tgcggccgat cttagccaga cgagcgggtt    2700
cggcccattc ggaccgcaag gaatcggtca atacactaca tggcgtgatt tcatatgcgc    2760
gattgctgat ccccatgtgt atcactggca aactgtgatg gacgacaccg tcagtgcgtc    2820
cgtcgcgcag gctctcgatg agctgatgct ttgggccgag gactgccccg aagtccggca    2880
cctcgtgcac gcggatttcg gctccaacaa tgtcctgacg gacaatggcc gcataacagc    2940
ggtcattgac tggagcgagg cgatgttcgg ggattcccaa tacgaggtcg ccaacatctt    3000
cttctggagg ccgtggttgg cttgtatgga gcagcagacg cgctacttcg agcggaggca    3060
tccggagctt gcaggatcgc cgcggctccg ggcgtatatg ctccgcattg gtcttgacca    3120
actctatcag agcttggttg acggcaattt cgatgatgca gcttgggcgc agggtcgatg    3180
cgacgcaatc gtccgatccg gagccgggac tgtcgggcgt acacaaatcg cccgcagaag    3240
cgcggccgtc tggaccgatg gctgtgtaga agtactcgcc gatagtggaa accgacgccc    3300
cagcactcgt ccgagggcaa aggaatagca cgtactacga gatttcgatt ccaccgccgc    3360
cttctatgaa aggttgggct tcggaatcgt tttccgggac gccggctgga tgatcctcca    3420
gcgcggggat ctcatgctgg agttcttcgc ccacccccaac ttgtttattg cagcttataa    3480
tggttacaaa taaagcaata gcatcacaaa tttcacaaat aaagcatttt tttcactgca    3540
ttctagttgt ggtttgtcca aactcatcaa tgtatcttat catgtctgta taccgtcgac    3600
ctctagctag agcttggcgt aatcatggtc atagctgttt cctgtgtgaa attgttatcc    3660
gctcacaatt ccacacaaca tacgagccgg aagcataaag tgtaaagcct ggggtgccta    3720
atgagtgagc taactcacat taattgcgtt gcgctcactg cccgctttcc agtcgggaaa    3780
cctgtcgtgc cagctgcatt aatgaatcgg ccaacgcgcg gggagaggcg gtttgcgtat    3840
tgggcgctct tccgcttcct cgctcactga ctcgctgcgc tcggtcgttc ggctgcggcg    3900
agcggtatca gctcactcaa aggcggtaat acgttatcc acagaatcag gggataacgc    3960
aggaaagaac atgtgagcaa aaggccagca aaaggccagg aaccgtaaaa aggccgcgtt    4020
gctggcgttt ttccataggc tccgcccccc tgacgagcat cacaaaaatc gacgctcaag    4080
tcagaggtgg cgaaacccga caggactata aagataccag gcgtttcccc ctggaagctc    4140
cctcgtgcgc tctcctgttc cgaccctgcc gcttaccgga tacctgtccg cctttctccc    4200
ttcgggaagc gtggcgcttt ctcatagctc acgctgtagg tatctcagtt cggtgtaggt    4260
cgttcgctcc aagctgggct gtgtgcacga accccccgtt cagcccgacc gctgcgcctt    4320
atccggtaac tatcgtcttg agtccaaccc ggtaagacac gacttatcgc cactggcagc    4380
agccactggt aacaggatta gcagagcgag gtatgtaggc ggtgctacag agttcttgaa    4440
gtggtggcct aactacggct acactagaag gacagtattt ggtatctgcg ctctgctgaa    4500
```

-continued

```
gccagttacc ttcggaaaaa gagttggtag ctcttgatcc ggcaaacaaa ccaccgctgg    4560
tagcggtggt ttttttgttt gcaagcagca gattacgcgc agaaaaaaag gatctcaaga    4620
agatcctttg atcttttcta cggggtctga cgctcagtgg aacgaaaact cacgttaagg    4680
gattttggtc atgagattat caaaaaggat cttcacctag atcctttta attaaaaatg     4740 aagttttaaa tcaatctaaa gtatatatga gtaaacttgg tctgacagtt accaatgctt    4800
aatcagtgag gcacctatct cagcgatctg tctatttcgt tcatccatag ttgcctgact    4860
ccccgtcgtg tagataacta cgatacggga gggcttacca tctggcccca gtgctgcaat    4920
gataccgcga gacccacgct caccggctcc agatttatca gcaataaacc agccagccgg    4980
aagggccgag cgcagaagtg gtcctgcaac tttatccgcc tccatccagt ctattaattg    5040
ttgccgggaa gctagagtaa gtagttcgcc agttaatagt ttgcgcaacg ttgttgccat    5100
tgctacaggc atcgtggtgt cacgctcgtc gtttggtatg gcttcattca gctccggttc    5160
ccaacgatca aggcgagtta catgatcccc catgttgtgc aaaaaagcgg ttagctcctt    5220
cggtcctccg atcgttgtca gaagtaagtt ggccgcagtg ttatcactca tggttatggc    5280
agcactgcat aattctctta ctgtcatgcc atccgtaaga tgcttttctg tgactggtga    5340
gtactcaacc aagtcattct gagaatagtg tatgcggcga ccgagttgct cttgcccggc    5400
gtcaatacgg gataataccg cgccacatag cagaacttta aaagtgctca tcattggaaa    5460
acgttcttcg gggcgaaaac tctcaaggat cttaccgctg ttgagatcca gttcgatgta    5520
acccactcgt gcacccaact gatcttcagc atcttttact ttcaccagcg tttctgggtg    5580
agcaaaaaca ggaaggcaaa atgccgcaaa aaagggaata agggcgacac ggaaatgttg    5640
aatactcata ctcttccttt ttcaatatta ttgaagcatt tatcagggtt attgtctcat    5700
gagcggatac atatttgaat gtatttagaa aaataaacaa ataggggttc cgcgcacatt    5760
tccccgaaaa gtgccacctg acgtc                                          5785
```

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cagaaacttc tcgacagacg tcgcggtgag     30

<210> SEQ ID NO 29
<211> LENGTH: 364
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Ala Pro Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Cys Ala Ser Ile Arg Pro Glu Gln Glu Arg Lys Phe Lys His Arg
            35                  40                  45

Leu Val Leu Arg Phe Glu Val Thr Gln Lys Thr Gln Arg Arg Trp Phe

```
            50                  55                  60
Leu Asp Lys Leu Val Asp Glu Ile Gly Val Gly Tyr Val Tyr Asp Ser
 65                  70                  75                  80

Gly Ser Val Ser Arg Tyr Tyr Leu Ser Gln Ile Lys Pro Leu His Asn
                 85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
            130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                165                 170                 175

Ala Ser Ser Ala Ala Ser Ser Ala Ser Ser Pro Gly Ser Gly Ile
                180                 185                 190

Ser Glu Ala Leu Arg Ala Gly Ala Gly Ser Gly Thr Gly Tyr Asn Lys
                195                 200                 205

Glu Phe Leu Leu Tyr Leu Ala Gly Phe Val Asp Gly Asp Gly Ser Ile
            210                 215                 220

Phe Ala Thr Ile Cys Pro Arg Gln Gln Tyr Lys Phe Lys His Gln Leu
225                 230                 235                 240

Arg Leu Arg Phe Glu Val Asp Gln Lys Thr Gln Arg Arg Trp Phe Leu
                245                 250                 255

Asp Lys Leu Val Asp Glu Ile Gly Val Gly Tyr Val Tyr Asp Leu Gly
            260                 265                 270

Ser Val Ser Arg Tyr Gly Leu Ser Glu Ile Lys Pro Leu His Asn Phe
            275                 280                 285

Leu Thr Gln Leu Gln Pro Phe Leu Lys Leu Lys Gln Lys Gln Ala Asn
            290                 295                 300

Leu Val Leu Lys Ile Ile Glu Gln Leu Pro Ser Ala Lys Glu Ser Pro
305                 310                 315                 320

Asp Lys Phe Leu Glu Val Cys Thr Trp Val Asp Gln Ile Ala Ala Leu
                325                 330                 335

Asn Asp Ser Lys Thr Arg Lys Thr Thr Ser Glu Thr Val Arg Ala Val
            340                 345                 350

Leu Asp Ser Leu Ser Glu Lys Lys Lys Ser Ser Pro
            355                 360

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagcacgtct caccccaccc ct                                            22

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 31
ggaatctgac tgtggtaagc ctgtacac                                              28

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cagcactcag gaggtagagg cagg                                                  24

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcttactgac atccactttg cctttctctc cacagg                                     36

<210> SEQ ID NO 34
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
acttgtttat tgcagcttat aatggttaca aataaagcaa tagcatcaca aatttcacaa           60
ataaagcatt tttttcactg cattctagtt gtggtttgtc caaactcatc aatgtatctt          120
atcatgtctg                                                                 130

<210> SEQ ID NO 35
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ctgtgccttc tagttgccag ccatctgttg tttgccccctc ccccgtgcct tccttgaccc          60
tggaaggtgc cactcccact gtcctttcct aataaaatga ggaaattgca tcgcattgtc         120
tgagtaggtg tcattctatt ctgggggtg gggtggggca ggacagcaag ggggaggatt         180
gggaagacaa tagcaggcat gctgggatg cggtgggctc tatgg                         225

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Met Ala Pro Lys Lys Lys Arg Lys Val
1               5
```

<210> SEQ ID NO 37
<211> LENGTH: 53
<212> TYPE: DNA
<213> ORGANISM: Cricetulus griseus

<400> SEQUENCE: 37
gaatgggaag ttccagaatt taaggcctca tatgaaaata taaagcgctt tct        53

<210> SEQ ID NO 38
<211> LENGTH: 36
<212> TYPE: DNA
<213> ORGANISM: Cricetulus griseus

<400> SEQUENCE: 38
gaatgggaag ttccagaatt taataaagcg ctttct        36

<210> SEQ ID NO 39
<211> LENGTH: 28
<212> TYPE: DNA
<213> ORGANISM: Cricetulus griseus

<400> SEQUENCE: 39
gaatgggaag ttccagaaag cgctttct        28

<210> SEQ ID NO 40
<211> LENGTH: 27
<212> TYPE: DNA
<213> ORGANISM: Cricetulus griseus

<400> SEQUENCE: 40
gaatgggaag ttccagaagc gctttct        27

<210> SEQ ID NO 41
<211> LENGTH: 69
<212> TYPE: DNA
<213> ORGANISM: Cricetulus griseus

<400> SEQUENCE: 41
tctgaaagcc agaagagcct agacagatag atgtcttgca tactctagag actacagatg        60
ccggcccag        69

<210> SEQ ID NO 42
<211> LENGTH: 58
<212> TYPE: DNA
<213> ORGANISM: Cricetulus griseus

<400> SEQUENCE: 42
tctgaaagcc agaagagcct agacatgcat actctagaga ctacagatgc cggcccag        58

<210> SEQ ID NO 43
<211> LENGTH: 49
<212> TYPE: DNA
<213> ORGANISM: Cricetulus griseus

<400> SEQUENCE: 43
tctgaaagcc agaagagcct agacagatag atgtcagatg ccggcccag        49

<210> SEQ ID NO 44
<211> LENGTH: 36
<212> TYPE: DNA

```
<213> ORGANISM: Cricetulus griseus

<400> SEQUENCE: 44
tctgaaagcc agaagagcct acagatgccg gcccag                              36

<210> SEQ ID NO 45
<211> LENGTH: 51
<212> TYPE: DNA
<213> ORGANISM: Cricetulus griseus

<400> SEQUENCE: 45
tctgaaagcc agaagagcct agacagatag atgtcttgca tgccggccca g             51

<210> SEQ ID NO 46
<211> LENGTH: 65
<212> TYPE: DNA
<213> ORGANISM: Cricetulus griseus

<400> SEQUENCE: 46
tctgaaagcc agaagagcct agacagatag atgtcttgct ctagagacta cagatgccgg    60
cccag                                                                65

<210> SEQ ID NO 47
<211> LENGTH: 67
<212> TYPE: DNA
<213> ORGANISM: Cricetulus griseus

<400> SEQUENCE: 47
tctgaaagcc agaagagcct agacagatag atgtcttata ctctagagac tacagatgcc    60
ggcccag                                                              67

<210> SEQ ID NO 48
<211> LENGTH: 38
<212> TYPE: DNA
<213> ORGANISM: Cricetulus griseus

<400> SEQUENCE: 48
tctgaaagcc agaagagcct agacagatgc cggcccag                            38

<210> SEQ ID NO 49
<211> LENGTH: 54
<212> TYPE: DNA
<213> ORGANISM: Cricetulus griseus

<400> SEQUENCE: 49
tctgaaagcc agaagagcct agacagatag atgtctttac agatgccgac ccag          54

<210> SEQ ID NO 50
<211> LENGTH: 65
<212> TYPE: DNA
<213> ORGANISM: Cricetulus griseus

<400> SEQUENCE: 50
tctgaaagcc agaagagcct agacagatag atgtcttgct ctagagacta cagatgccgg    60
cccag                                                                65

<210> SEQ ID NO 51
<211> LENGTH: 69
<212> TYPE: DNA
<213> ORGANISM: Cricetulus griseus

<400> SEQUENCE: 51
```

```
tctgaaagcc agaagagcct agacagatag atgtctttgc atactctaga gactacagat    60
gccggccca                                                            69

<210> SEQ ID NO 52
<211> LENGTH: 75
<212> TYPE: DNA
<213> ORGANISM: Cricetulus griseus

<400> SEQUENCE: 52
gatgctttat tcctagagac caatttaagg cactcgtgta aacggataat ggacatggtg    60
agcaaccagc acccc                                                     75

<210> SEQ ID NO 53
<211> LENGTH: 69
<212> TYPE: DNA
<213> ORGANISM: Cricetulus griseus

<400> SEQUENCE: 53
gatgctttat tcctagagac caatttaagg cactcgtgtg taatggacat ggtgagcaac    60
cagcacccc                                                            69

<210> SEQ ID NO 54
<211> LENGTH: 74
<212> TYPE: DNA
<213> ORGANISM: Cricetulus griseus

<400> SEQUENCE: 54
gatgctttat tcctagagac caatttaagg cactcgtgta acggataatg gacatggtga    60
gcaaccagca cccc                                                      74

<210> SEQ ID NO 55
<211> LENGTH: 71
<212> TYPE: DNA
<213> ORGANISM: Cricetulus griseus

<400> SEQUENCE: 55
gatgctttat tcctagagac caatttaagg cactcaaacg ataatggac atggtgagca     60 accagcaccc c                                                         71

<210> SEQ ID NO 56
<211> LENGTH: 73
<212> TYPE: DNA
<213> ORGANISM: Cricetulus griseus

<400> SEQUENCE: 56
gatgctttat tcctagagac caatttaagg cactcgtaaa cggataatgg acatggtgag    60
caaccagcac ccc                                                       73

<210> SEQ ID NO 57
<211> LENGTH: 74
<212> TYPE: DNA
<213> ORGANISM: Cricetulus griseus

<400> SEQUENCE: 57
gatgctttat tcctagagac caatttaagg cgctgtgtaa acggataatg gacatggtga    60
gcaaccagca cccc                                                      74

<210> SEQ ID NO 58
```

```
<210> SEQ ID NO 58
<211> LENGTH: 75
<212> TYPE: DNA
<213> ORGANISM: Cricetulus griseus

<400> SEQUENCE: 58
gatgctttat tcctagagac caatttaagg cattcgtgta aacggataat ggacatggtg    60
agcaaccagc ccccc                                                    75

<210> SEQ ID NO 59
<211> LENGTH: 75
<212> TYPE: DNA
<213> ORGANISM: Cricetulus griseus

<400> SEQUENCE: 59
gatgctttat tcctagagac caatttaagg cactcatgta aacggataat ggacatggtg    60
agcaaccagc ccccc                                                    75

<210> SEQ ID NO 60
<211> LENGTH: 75
<212> TYPE: DNA
<213> ORGANISM: Cricetulus griseus

<400> SEQUENCE: 60
gatgctttat tcctagagac caatttaagg cgctcgtgta aacggataat ggacatggtg    60
agcaaccagc ccccc                                                    75

<210> SEQ ID NO 61
<211> LENGTH: 75
<212> TYPE: DNA
<213> ORGANISM: Cricetulus griseus

<400> SEQUENCE: 61
gatgctttat tcctagagac caatttaagg cactcgcgta aacggataat ggacatggtg    60
agcaaccagc ccccc                                                    75

<210> SEQ ID NO 62
<211> LENGTH: 75
<212> TYPE: DNA
<213> ORGANISM: Cricetulus griseus

<400> SEQUENCE: 62
gatgctttat tcctagagac caatttaagg cacacgtgta aacggataat ggacatggtg    60
agcaaccagc ccccc                                                    75

<210> SEQ ID NO 63
<211> LENGTH: 74
<212> TYPE: DNA
<213> ORGANISM: Cricetulus griseus

<400> SEQUENCE: 63
gatgctttat tcctagagac caatttaagg cactcgtgtg taaacggata atggacatgg    60
tgagcaacca gcac                                                     74

<210> SEQ ID NO 64
<211> LENGTH: 57
<212> TYPE: DNA
<213> ORGANISM: Cricetulus griseus

<400> SEQUENCE: 64
gatgctttat tcctagagac caatttaagg catggtgagt aaccgagcaa ccagcac      57
```

```
<210> SEQ ID NO 65
<211> LENGTH: 9
<212> TYPE: PRT
<213> ORGANISM: Unknown
<220> FEATURE:
<223> OTHER INFORMATION: Description of Unknown: LAGLIDADG family homing
      endonuclease peptide

<400> SEQUENCE: 65

Leu Ala Gly Leu Ile Asp Ala Asp Gly
1               5
```

METHODS AND PRODUCTS FOR PRODUCING ENGINEERED MAMMALIAN CELL LINES WITH AMPLIFIED TRANSGENES

CROSS REFERENCE TO RELATED APPLICATIONS

This application is a continuation of U.S. patent application Ser. No. 14/091,572, filed Nov. 27, 2013, which is a continuation of International Application No. PCT/US2012/040599, filed Jun. 1, 2012, which claims priority to U.S. Provisional application No. 61/492,174 filed Jun. 1, 2011, the disclosures of all of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Oct. 1, 2015, is named 2000706-00156US3_SL.txt and is 187,384 bytes in size.

FIELD OF THE INVENTION

The invention relates to the field of molecular biology and recombinant nucleic acid technology. In particular, the invention relates to methods of inserting genes into defined locations in the chromosomal DNA of cultured mammalian cell lines which are subject to gene amplification. The invention also relates to meganucleases, vectors and engineered cell lines necessary for performing the methods, cell lines resulting from the application of the methods, and use of the cell lines to produce protein products of interest.

BACKGROUND OF THE INVENTION

Therapeutic proteins are the primary growth driver in the global pharmaceutical market (Kresse, *Eur J Pharm Biopharm* 72, 479 (2009)). In 2001, biopharmaceuticals accounted for $24.3 billion in sales. By 2007, this number had more than doubled to $54.5 billion. The market is currently estimated to reach $78 billion by 2012 (Pickering, *Spectrum Pharmaceutical Industry Dynamics Report, Decision Resources, Inc.*, 5 (2008)). This includes sales of "blockbuster" drugs such as erythropoietin, tissue plasminogen activator, and interferon, as well as numerous "niche" drugs such as enzyme replacement therapies for lysosomal storage disorders. The unparalleled growth in market size, however, is driven primarily by skyrocketing demand for fully human and humanized monoclonal antibodies (Reichert, *Curr Pharm Biotechnol* 9, 423 (2008)). Because they have the ability to confer a virtually unlimited spectrum of biological activities, monoclonal antibodies are quickly becoming the most powerful class of therapeutics available to physicians. Not surprisingly, more than 25% of the molecules currently undergoing clinical trials in the United States and Europe are monoclonal antibodies (Reichert, *Curr Pharm Biotechnol* 9, 423 (2008)).

Unlike more traditional pharmaceuticals, therapeutic proteins are produced in living cells. This greatly complicates the manufacturing process and introduces significant heterogeneity into product formulations (Field, *Recombinant Human IgG Production from Myeloma and Chinese Hamster Ovary Cells*, in *Cell Culture and Upstream Processing*, Butler, ed., (Taylor and Francis Group, New York, 2007)). In addition, protein drugs are typically required at unusually high doses, which necessitates highly scalable manufacturing processes and makes manufacturing input costs a major price determinant. For these reasons, treatment with a typical therapeutic antibody (e.g., the anti-HER2-neu monoclonal Herceptin®) costs $60,000-$80,000 for a full course of treatment (Fleck, *Hastings Center Report* 36, 12 (2006)). Further complicating the economics of biopharmaceutical production is the fact that many of the early blockbuster biopharmaceuticals are off-patent (or will be off-patent soon) and the US and EU governments are expected to greatly streamline the regulatory approval process for "biogeneric" and "biosimilar" therapeutics (Kresse, *Eur J Pharm Biopharm* 72, 479 (2009)). These factors should lead to a significant increase in competition for sales of many prominent biopharmaceuticals (Pickering, *Spectrum Pharmaceutical Industry Dynamics Report, Decision Resources, Inc.*, 5 (2008)). Therefore, there is enormous interest in technologies which reduce manufacturing costs of protein therapeutics (Seth et al., *Curr Opin Biotechnol* 18, 557 (2007)).

Many of the protein pharmaceuticals on the market are glycoproteins that cannot readily be produced in easy-to-manipulate biological systems such as bacteria or yeast. For this reason, recombinant therapeutic proteins are produced almost exclusively in mammalian cell lines, primarily Chinese hamster ovary (e.g., CHO-K1), mouse myeloma (e.g., NS0), baby hamster kidney (BHK), murine C127, human embryonic kidney (e.g., HEK-293), or human retina-derived (e.g., PER-C6) cells (Andersen and Krummen, *Curr Opin Biotechnol* 13, 117 (2002)). Of these, CHO cells are, by far, the most common platform for bioproduction because they offer the best combination of high protein expression levels, short doubling time, tolerance to a wide range of media conditions, established transfection and amplification protocols, an inability to propagate most human pathogens, a paucity of blocking intellectual property, and the longest track record of FDA approval (Field, *Recombinant Human IgG Production from Myeloma and Chinese Hamster Ovary Cells*, in *Cell Culture and Upstream Processing*, Butler, ed. (Taylor and Francis Group, New York, 2007)).

Large-market biopharmaceuticals are typically produced in enormous stirred-tank bioreactors containing hundreds of liters of CHO cells stably expressing the protein product of interest (Chu and Robinson, *Curr Opin Biotechnol* 12, 180 (2001), Coco-Martin and Harmsen, *Bioprocess International* 6, 28 (2008)). Under optimized industrial conditions, such manufacturing processes can yield in excess of 5 g of protein per liter of cells per day (Coco-Martin and Harmsen, *Bioprocess International* 6, 28 (2008)). Because of the large number of cells involved (~50 billion cells per liter), the level of protein expression per cell has a very dramatic effect on yield. For this reason, all of the cells involved in the production of a particular biopharmaceutical must be derived from a single "high-producer" clone, the production of which constitutes one of the most time- and resource-intensive steps in the manufacturing process (Clarke and Compton, Bioprocess International 6, 24 (2008)).

The first step in the large-scale manufacture of a biopharmaceutical is the transfection of mammalian cells with plasmid DNA encoding the protein product of interest under the control of a strong constitutive promoter. Stable transfectants are selected by using a selectable marker gene also carried on the plasmid. Most frequently, this marker is a dihydrofolate reductase (DHFR) gene which, when transfected into a DHFR deficient cell line such as DG44, allows for the selection of stable transfectants using media deficient in hypoxanthine. The primary reason for using DHFR as a selectable marker is that it enables a process called "gene amplification". By growing stable transfectants in gradually increasing concentrations of methotrexate (MTX), a DHFR inhibitor, it is possible to amplify the number of copies of the DHFR gene present in the genome. Because the gene encoding the protein product of interest is physically coupled to the DHFR gene, this results in amplification of both genes with a concomitant increase in the expression level of the therapeutic protein (Butler, *Cell Line Development for Culture Strategies: Future Prospects to Improve Yields*, in *Cell Culture and Upstream Processing*, Butler, ed., (Taylor and Francis Group, New York, 2007)). Related systems for the creation of stable bioproduction lines use the glutamine synthetase (GS) or hypoxanthine phosphoribosyltransferase (HPRT) genes as selectable markers and require the use of GS- or HPRT-deficient cell lines as hosts for transfection (Clarke and Compton, *Bioprocess International* 6, 24 (2008)). In the case of the GS system, gene amplification is accomplished by growing cells in the presence of methionine sulphoximine (MSX) (Clarke and Compton, Bioprocess International 6, 24 (2008)). In the case of the HPRT system, gene amplification is accomplished by growing cells in HAT medium, which contains aminopterin, hypoxanthine, and thymidine (Kellems, ed. *Gene amplification in mammalian cells: a comprehensive guide*, Marcel Dekker, New York, 1993).

In all of these systems, the initial plasmid DNA comprising a biotherapeutic gene expression cassette and a selectable marker integrates into a random location in the genome, resulting in extreme variability in therapeutic protein expression from one stable transfectant to another (Collingwood and Urnov, *Targeted Gene Insertion to Enhance Protein Production from Cell Lines*, in *Cell Culture and Upstream Processing*, Butler, ed. (Taylor and Francis Group, New York, 2007)). For this reason, it is necessary to screen hundreds to thousands of initial transfectants to identify cells which express acceptably high levels of gene product both before and after gene amplification (Butler, *Cell Line Development for Culture Strategies: Future Prospects to Improve Yields*, in *Cell Culture and Upstream Processing*, Butler, ed. (Taylor and Francis Group, New York, 2007)). A second and more problematic consequence of random gene integration is the phenomenon of transgene silencing, in which recombinant protein expression slows or ceases entirely over time (Collingwood and Urnov, *Targeted Gene Insertion to Enhance Protein Production from Cell Lines*, in *Cell Culture and Upstream Processing*, Butler, ed. (Taylor and Francis Group, New York, 2007)). Because these effects often do not manifest themselves for weeks to months following the initial transfection and screening process, it is generally necessary to carry and expand dozens of independent clonal lines to identify one that expresses the protein of interest consistently over time (Butler, *Cell Line Development for Culture Strategies: Future Prospects to Improve Yields*, in *Cell Culture and Upstream Processing*, Butler, ed. (Taylor and Francis Group, New York, 2007)).

This large number of screening and expansion steps results in a very lengthy and expensive process to simply generate the cell line that will, ultimately, produce the therapeutic of interest. Indeed, using conventional methods, a minimum of 10 months (with an average of 18 months) and an upfront investment of tens of millions of dollars in labor and material is required to produce an initial pool of protein-expressing cells suitable for industrial manufacturing (Butler, *Cell Line Development for Culture Strategies: Future Prospects to Improve Yields*, in *Cell Culture and Upstream Processing*, Butler, ed. (Taylor and Francis Group, New York, 2007)). If one takes into account lost time on market for a blockbuster protein therapeutic, inefficiencies in cell line production can cost biopharmaceutical manufacturers hundreds of millions of dollars (Seth et al., *Curr Opin Biotechnol* 18, 557 (2007)).

Much of the time and expense of bioproduction cell line creation can be attributed to random genomic integration of the bioproduct gene resulting in clone-to-clone variability in genotype and, hence, variability in gene expression. One way to overcome this is to target gene integration to a defined location that is known to support a high level of gene expression. To this end, a number of systems have been described which use the Cre, Flp, or ΦC31 recombinases to target the insertion of a bioproduct gene (reviewed in Collingwood and Urnov, *Targeted Gene Insertion to Enhance Protein Production from Cell Lines*, in *Cell Culture and Upstream Processing*, Butler, ed. (Taylor and Francis Group, New York, 2007)). Recent embodiments of these systems, most notably the Flp-In® system marketed by Invitrogen Corp. (Carlsbad, Calif.), couple bioproduct gene integration with the reconstitution of a split selectable marker so that cells with correctly targeted genes can be selected. As expected, these systems result in greatly reduced heterogeneity in gene expression and, in some cases, individual stable transfectants can be pooled, obviating the time and expense associated with expanding a single clone.

The principal drawback to recombinase-based gene targeting systems is that the recombinase recognition sites (loxP, FRT, or attB/attP sites) do not naturally occur in mammalian genomes. Therefore, cells must be pre-engineered to incorporate a recognition site for the recombinase before that site can be subsequently targeted for gene insertion. Because the recombinase site itself integrates randomly into the genome, it is still necessary to undertake extensive screening and evaluation to identify clones which carry the site at a location that is suitable for high level, long-term gene expression (Collingwood and Urnov, *Targeted Gene Insertion to Enhance Protein Production from Cell Lines*, in *Cell Culture and Upstream Processing*, Butler, ed. (Taylor and Francis Group, New York, 2007)). In addition, the biomanufacturing industry is notoriously hesitant to adopt "new" cell lines, such as those that have been engineered to carry a recombinase site, that do not have a track record of FDA approval. For these reasons, recombinase-based cell engineering systems may not readily be adopted by the industry and an approach that allows biomanufacturers to utilize their existing cell lines is preferable.

SUMMARY OF THE INVENTION

The present invention depends, in part, upon the development of mammalian cell lines in which sequences of interest (e.g., exogenous, actively transcribed transgenes) are inserted proximal to an endogenous selectable gene in an amplifiable locus, and the discovery that (a) the insertion of such exogenous sequences of interest does not inhibit amplification of the endogenous selectable gene, (b) the exogenous sequence of interest can be co-amplified with the endogenous selectable gene, and (c) the resultant cell lines, with an amplified region comprising multiple copies of the endogenous selectable gene and the exogenous sequence of interest, are stable for extended periods even in the absence of the selection regime which was employed to induce amplification. Thus, in one aspect, the invention provides a method for producing cell lines which can be used for biomanufacturing of a protein product of interest by specifically targeting the insertion of an exogenous sequence of interest capable of actively expressing the protein product of interest proximal to an endogenous selectable gene. In another aspect, the invention provides engineered cell lines that can be used to produce protein products of interest (e.g., therapeutic proteins such as monoclonal antibodies) at high levels.

It is understood that any of the embodiments described below can be combined in any desired way, and any embodiment or combination of embodiments can be applied to each of the aspects described below, unless the context indicates otherwise.

In one aspect, the invention provides a recombinant mammalian cell comprising an engineered target site stably integrated within selectable gene within an amplifiable locus, wherein the engineered target site disrupts the function of the selectable gene and wherein the engineered target site comprises a recognition sequence for a site specific endonuclease.

In some embodiments, the selectable gene is glutamine synthetase (GS) and the locus is methionine sulphoximine (MSX) amplifiable. In some embodiments, the selectable gene is dihydrofolate reductase (DHFR) and the locus is Methotrexate (MTX) amplifiable.

In some embodiments, the selectable gene is selected from the group consisting of Dihydrofolate Reductase, Glutamine Synthetase, Hypoxanthine Phosphoribosyltransferase, Threonyl tRNA Synthetase, Na,K-ATPase, Asparagine Synthetase, Ornithine Decarboxylase, Inosine-5'-monophosphate dehydrogenase, Adenosine Deaminase, Thymidylate Synthetase, Aspartate Transcarbamylase, Metallothionein, Adenylate Deaminase (1,2), UMP-Synthetase and Ribonucleotide Reductase.

In some embodiments, the selectable gene is amplifiable by selection with a selection agent selected from the group consisting of Methotrexate (MTX), Methionine sulphoximine (MSX), Aminopterin, hypoxanthine, thymidine, Borrelidin, Ouabain, Albizziin, Beta-aspartyl hydroxamate, alpha-difluoromethylornithine (DFMO), Mycophenolic Acid, Adenosine, Alanosine, 2'deoxycoformycin, Fluorouracil, N-Phosphonacetyl-L-Aspartate (PALA), Cadmium, Adenine, Azaserine, Coformycin, 6-azauridine, pyrazofuran, hydroxyurea, motexafin gadolinium, fludarabine, cladribine, gemcitabine, tezacitabine and triapine.

In some embodiments, the engineered target site is inserted into an exon of the selectable gene. In some embodiments, the site specific endonuclease is a meganuclease, a zinc finger nuclease or TAL effector nuclease. In some embodiment, the recombinant cell further comprises the site specific endonuclease.

In one aspect, the invention provides a recombinant mammalian cell comprising an engineered target site stably integrated proximal to a selectable gene within an amplifiable locus, wherein the engineered target site comprises a recognition sequence for a site specific endonuclease.

In some embodiments, the engineered target site is downstream from the 3' regulatory region of the selectable gene. In some embodiments, the engineered target site is 0 to 100,000 base pairs downstream from the 3' regulatory region of the selectable gene. In other embodiments, the engineered target site is upstream from the 5' regulatory region of the selectable gene. In some embodiments, the engineered target site is 0 to 100,000 base pairs upstream from the 5' regulatory region of the selectable gene.

In another aspect, the invention provides a method for inserting an exogenous sequence into an amplifiable locus of a mammalian cell comprising: (a) providing a mammalian cell having an endogenous target site proximal to a selectable gene within the amplifiable locus, wherein the endogenous target site comprises: (i) a recognition sequence for an engineered meganuclease; (ii) a 5' flanking region 5' to the recognition sequence; and (iii) a 3' flanking region 3' to the recognition sequence; and (b) introducing a double-stranded break between the 5' and 3' flanking regions of the endogenous target site; (c) contacting the cell with a donor vector comprising from 5' to 3': (i) a donor 5' flanking region homologous to the 5' flanking region of the endogenous target site; (ii) an exogenous sequence; and (iii) a donor 3' flanking region homologous to the 3' flanking region of the endogenous target site; whereby the donor 5' flanking region, the exogenous sequence and the donor 3' flanking region are inserted between the 5' and 3' flanking regions of the endogenous target site by homologous recombination to provide a modified cell.

In some embodiments, the method further comprises growing the modified cell in the presence of a compound that inhibits the function of the selectable gene to amplify the copy number of the selectable gene. In some embodiments, the exogenous sequence comprises a gene of interest.

In some embodiments endogenous target site is downstream from the 3' regulatory region of the selectable gene. In some embodiments, the endogenous target site is 0 to 100,000 base pairs downstream from the 3' regulatory region of the selectable gene. In other embodiments, the endogenous target site is upstream from the 5' regulatory region of the selectable gene. In some embodiments, the endogenous target site is 0 to 100,000 base pairs upstream from the 5' regulatory region of the selectable gene.

In one aspect, the invention provides a method for inserting an exogenous sequence into an amplifiable locus of a mammalian cell comprising: (a) providing a mammalian cell having an endogenous target site proximal to a selectable gene within the amplifiable locus, wherein the endogenous target site comprises: (i) a recognition sequence for an engineered meganuclease; (ii) a 5' flanking region 5' to the recognition sequence; and (iii) a 3' flanking region 3' to the recognition sequence; and (b) introducing a double-stranded break between the 5' and 3' flanking regions of the endogenous target site; (c) contacting the cell with an engineered target site donor vector comprising from 5' to 3': (i) a donor 5' flanking region homologous to the 5' flanking region of the endogenous target site; (ii) an exogenous sequence comprising an engineered target site; and (iii) a donor 3' flanking region homologous to the 3' flanking region of the endogenous target site; whereby the donor 5' flanking region, the exogenous sequence and the donor 3' flanking region are inserted between the 5' and 3' flanking regions of the endogenous target site by homologous recombination to provide a mammalian cell comprising the engineered target site; (d) introducing a double-stranded break between the 5' and 3' flanking regions of the engineered target site; (e) contacting the cell comprising the engineered target site with a sequence of interest donor vector comprising from 5' to 3': (i) a donor 5' flanking region homologous to the 5' flanking region of the engineered target site; (ii) an exogenous sequence comprising a sequence of interest; and (iii) a donor 3' flanking region homologous to the 3' flanking region of the engineered target site; whereby the donor 5' flanking region, the exogenous sequence comprising the sequence of interest and the donor 3' flanking region are inserted between the 5' and 3' flanking regions of the engineered target site by homologous recombination to provide an engineered mammalian cell comprising the sequence of interest.

In some embodiments, the method further comprises growing the engineered mammalian cell in the presence of a compound that inhibits the function of the selectable gene to amplify the copy number of the selectable gene. In some embodiments, the sequence of interest comprises a gene.

In another aspect, the invention provides a method for inserting an exogenous sequence into an amplifiable locus of a mammalian cell comprising: (a) providing a mammalian cell having an endogenous target site within a selectable gene within the amplifiable locus, wherein the endogenous target site comprises: (i) a recognition sequence for an engineered meganuclease; (ii) a 5' flanking region 5' to the recognition sequence; and (iii) a 3' flanking region 3' to the recognition sequence; and (b) introducing a double-stranded break between the 5' and 3' flanking regions of the endogenous target site; (c) contacting the cell with an engineered target site donor vector comprising from 5' to 3': (i) a donor 5' flanking region homologous to the 5' flanking region of the endogenous target site; (ii) an exogenous sequence comprising an engineered target site; and (iii) a donor 3' flanking region homologous to the 3' flanking region of the endogenous target site; whereby the donor 5' flanking region, the exogenous sequence and the donor 3' flanking region are inserted between the 5' and 3' flanking regions of the endogenous target site by homologous recombination to provide a mammalian cell comprising the engineered target site; (d) introducing a double-stranded break between the 5' and 3' flanking regions of the engineered target site; (e) contacting the cell comprising the engineered target site with a sequence of interest donor vector comprising from 5' to 3': (i) a donor 5' flanking region homologous to the 5' flanking region of the engineered target site; (ii) an exogenous sequence comprising a sequence of interest; and (iii) a donor 3' flanking region homologous to the 3' flanking region of the engineered target site; whereby the donor 5' flanking region, the exogenous sequence comprising the sequence of interest and the donor 3' flanking region are inserted between the 5' and 3' flanking regions of the engineered target site by homologous recombination to provide a engineered mammalian cell comprising the sequence of interest.

In some embodiments, the method further comprises growing the engineered mammalian cell in the presence of a compound that inhibits the function of the selectable gene to amplify the copy number of the selectable gene.

In some embodiments, the sequence of interest comprises a gene.

In some embodiments, the endogenous target site is within an intron of the selectable gene. In other embodiments, the endogenous target site is within an exon of the selectable gene.

In one aspect, the invention provides a recombinant meganuclease comprising a polypeptide having at least 75%, 80%, 85%, 90%, 95%, 97%, 98% or 99% sequence identity to SEQ ID NO: 15.

In another aspect, the invention provides a recombinant meganuclease comprising the amino acid sequence of SEQ ID NO: 15.

In another aspect, the invention provides a recombinant meganuclease which recognizes and cleaves a recognition site having 75%, 85%, 90%, 95%, 97%, 98% or 99% sequence identity to SEQ ID NO: 14. In one embodiment, the meganuclease recognizes and cleaves a recognition site of SEQ ID NO: 14.

In another aspect, the invention provides a recombinant meganuclease comprising a polypeptide having at least 75%, 85%, 90%, 95%, 97%, 98% or 99% sequence identity to SEQ ID NO:9. In one embodiment, the recombinant meganuclease has the sequence of the meganuclease of SEQ ID NO:9.

In another aspect, the invention provides a recombinant meganuclease which recognizes and cleaves a recognition site having at least 75%, 85%, 90%, 95%, 97%, 98% or 99% sequence identity to SEQ ID NO: 7. In one embodiment, the meganuclease recognizes and cleaves a recognition site of SEQ ID NO: 7.

In another aspect, the invention provides a recombinant meganuclease comprising a polypeptide having at least 75%, 80%, 85%, 90%, 95%, 97%, 98% or 99% sequence identity to SEQ ID NO: 10. In one embodiment, the recombinant meganuclease comprises the polypeptide of SEQ ID NO: 10.

In another aspect, the invention provides a recombinant meganuclease which recognizes and cleaves a recognition site having at least 75%, 85%, 90%, 95%, 97%, 98% or 99% sequence identity to SEQ ID NO: 8. In one embodiment, the meganuclease recognizes and cleaves a recognition site of SEQ ID NO: 8.

In another aspect, the invention provides a recombinant meganuclease comprising a polypeptide having at least 75%, 80%, 85%, 90%, 95%, 97%, 98% or 99% sequence identity to SEQ ID NO: 13. In embodiment, the recombinant meganuclease comprises the polypeptide of SEQ ID NO: 13.

In another aspect, the invention provides a recombinant meganuclease which recognizes and cleaves a recognition site having at least 75%, 85%, 90%, 95%, 97%, 98% or 99% sequence identity to SEQ ID NO: 12. In one embodiment, the meganuclease recognizes and cleaves a recognition site of SEQ ID NO: 12.

In another aspect, the invention provides a recombinant meganuclease comprising a polypeptide having at least 75%, 80%, 85%, 90%, 95%, 97%, 98% or 99% sequence identity to SEQ ID NO: 29. In one embodiment, the recombinant meganuclease comprises the polypeptide of SEQ ID NO: 29.

In another aspect, the invention provides a recombinant meganuclease which recognizes and cleaves a recognition site having at least 75%, 85%, 90%, 95%, 97%, 98% or 99% sequence identity to SEQ ID NO: 30. In one embodiment, the meganuclease recognizes and cleaves a recognition site of SEQ ID NO: 30.

In another aspect, the invention provides recombinant mammalian cell lines which continue to express a protein product of interest from an exogenous sequence of interest present in an amplified region of the genome (i.e., present in 2-1,000 copies, co-amplified with a selectable gene in an amplifiable locus) for a period of at least 8, 9, 10, 11, 12, 13, or 14 weeks after removal of the amplification selection agent, and with a reduction of expression levels and/or copy number of less than 20, 25, 30, 35 or 40%.

In another aspect, the invention provides methods of producing recombinant cells with amplified regions including a sequence of interest and a selectable gene by subjecting the above-described recombinant cells to selection with a selection agent which causes co-amplification of the sequence of interest and the selectable gene.

In another aspect, the invention provides methods of producing a protein product of interest by culturing the above-described recombinant cells, or the above-described recombinant cells with amplified regions, and obtaining the protein product of interest from the culture medium or a cell lysate.

DETAILED DESCRIPTION OF THE INVENTION

1.1 Introduction

Figure 1:
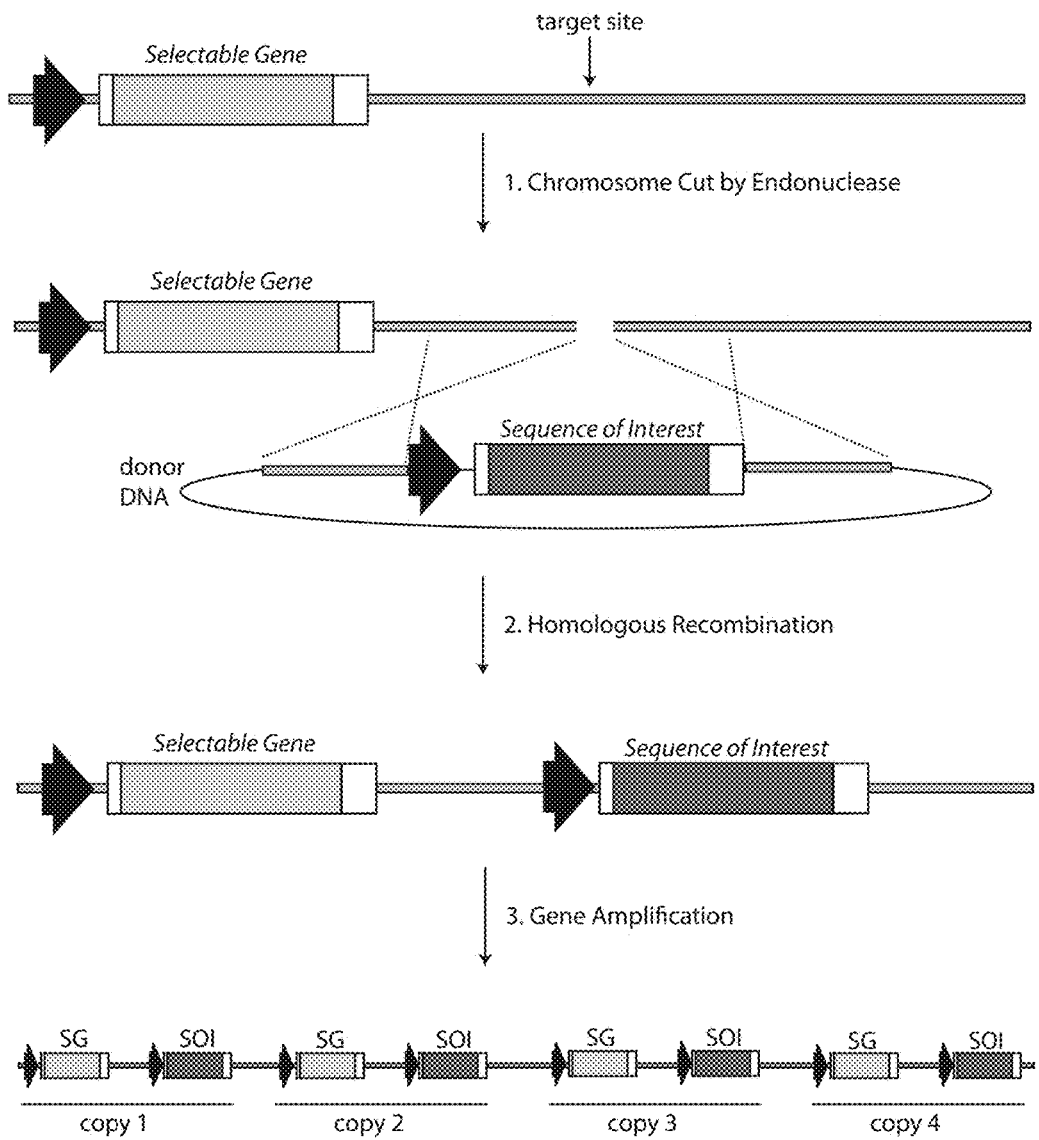
FIG. 1. A general strategy for targeting a sequence of interest to an amplifiable locus.

The present invention depends, in part, upon the development of mammalian cell lines in which exogenous actively transcribed transgenes have been inserted proximal to an endogenous amplifiable locus, and the discovery that (a) the insertion of such exogenous actively transcribed transgenes does not prevent or substantially inhibit amplification of the endogenous amplifiable locus, (b) the exogenous actively transcribed transgene can be co-amplified with the endogenous amplifiable locus, and (c) the resultant cell line, with an amplified region comprising multiple copies of the endogenous amplifiable locus and the exogenous actively transcribed transgene is stable for extended periods even in the absence of the selection regime which was employed to induce amplification. Thus, in one aspect, the invention provides a method for producing cell lines which can be used for biomanufacturing of a protein product of interest by specifically targeting the insertion of an exogenous gene capable of actively expressing the protein product of interest proximal to an endogenous amplifiable locus. In another aspect, the invention provides engineered cell lines that can be used to produce protein products of interest (e.g., therapeutic proteins such as monoclonal antibodies) at high levels.

1.2 References and Definitions

The patent and scientific literature referred to herein establishes knowledge that is available to those of skill in the art. The entire disclosures of the issued U.S. patents, pending applications, published foreign applications, and scientific and technical references cited herein, including protein and nucleic acid database sequences, are hereby incorporated by reference to the same extent as if each was specifically and individually indicated to be incorporated by reference.

As used herein, the term "meganuclease" refers to naturally-occurring homing endonucleases (also referred to as Group I intron encoded endonucleases) or non-naturally-occurring (e.g., rationally designed or engineered) endonucleases based upon the amino acid sequence of a naturally-occurring homing endonuclease. Examples of naturally-occurring meganucleases include I-SceI, I-CreI, I-CeuI, I-DmoI, I-MsoI, I-AniI, etc. Rationally designed meganucleases are disclosed in, for example, WO 2007/047859 and WO 2009/059195, and can be engineered to have modified DNA-binding specificity, DNA cleavage activity, DNA-binding affinity, or dimerization properties relative to a naturally occurring meganuclease. A meganuclease may bind to double-stranded DNA as a homodimer (e.g., wild-type I-CreI), or it may bind to DNA as a heterodimer (e.g., engineered meganucleases disclosed in WO 2007/047859). An engineered meganuclease may also be a "single-chain meganuclease" in which a pair of DNA-binding domains derived from a natural meganuclease are joined into a single polypeptide using a peptide linker (e.g., single-chain meganucleases disclosed in WO 2009/059195).

As used herein, the term "single-chain meganuclease" refers to a polypeptide comprising a pair of meganuclease subunits joined by a linker. A single-chain meganuclease has the organization: N-terminal subunit—Linker—C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. Methods of producing single-chain meganucleases are disclosed in WO 2009/059195.

As used herein, the term "site specific endonuclease" means a meganuclease, zinc-finger nuclease or TAL effector nuclease.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant. As used herein, the term "engineered" is synonymous with the term "recombinant."

As used herein, with respect to a meganuclease, the term "wild-type" refers to any naturally-occurring form of a meganuclease. The term "wild-type" is not intended to mean the most common allelic variant of the enzyme in nature but, rather, any allelic variant found in nature. Wild-type homing endonucleases are distinguished from recombinant or non-naturally-occurring meganucleases.

As used herein, the term "recognition sequence" refers to a DNA sequence that is bound and cleaved by a meganuclease. A recognition sequence comprises a pair of inverted, 9 base pair "half sites" which are separated by four base pairs. In the case of a homo- or heterodimeric meganucleases, each of the two monomers makes base-specific contacts with one half-site. In the case of a single-chain heterodimer meganuclease, the N-terminal domain of the protein contacts a first half-site and the C-terminal domain of the protein contacts a second half-site. In the case if I-CreI, for example, the recognition sequence is 22 base pairs and comprises a pair of inverted, 9 base pair "half sites" which are separated by four base pairs.

As used herein, the term "target site" refers to a region of the chromosomal DNA of a cell comprising a target sequence into which a sequence of interest can be inserted. As used herein, the term "engineered target site" refers to an exogenous sequence of DNA integrated into the chromosomal DNA of a cell comprising an engineered target sequence into which a sequence of interest can be inserted.

As used herein, the term "target sequence" means a DNA sequence within a target site which includes one or more recognition sequences for a nuclease, integrase, transposase, and/or recombinase. For example, a target sequence can include a recognition sequence for a meganuclease. As used herein, an "engineered target sequence" means an exogenous target sequence which is introduced into a chromosome to serve as the insertion point for another sequence.

As used herein, the term "flanking region" or "flanking sequence" refers to a sequence of >3 or, preferably, >50 or, more preferably, >200 or, most preferably, >400 base pairs of DNA which is immediately 5' or 3' to a reference sequence (e.g., a target sequence or sequence of interest).

As used herein, the terms "amplifiable locus" refers to a region of the chromosomal DNA of a cell which can be amplified by selection with one or more compounds (e.g., drugs) in the growth media. An amplifiable locus will typically comprise a gene encoding a protein which, under the appropriate conditions, is necessary for cell survival. By inhibiting the function of such an essential protein, for example with a small molecule drug, the amplifiable locus is duplicated many times over as a means of increasing the copy number of the essential gene. A gene of interest, if integrated into an amplifiable locus, will also become duplicated with the essential gene. Examples of amplifiable loci include the chromosomal regions comprising the DHFR, GS, and HPRT genes.

As used herein, the term "amplified locus" or "amplified gene" or "amplified sequence" refers to a locus, gene or sequence which is present in 2-1,000 copies as a result of gene amplification in response to selection of a selectable gene. An amplified gene or sequence can be a gene or sequence which is co-amplified due to selection of a selectable gene in the same amplifiable locus. In preferred embodiments, a sequence of interest is amplified to at least 3, 4, 5, 6, 7, 8, 9 or 10 copies.

As used herein, the term "selectable gene" refers to an endogenous gene that is essential for cell survival under some specific culture conditions (e.g., presence or absence of a nutrient, toxin or drug). Selectable genes are endogenous to the cell and are distinguished from exogenous "selectable markers" such as antibiotic resistance genes. Selectable genes exist in their natural context in the chromosomal DNA of the cell. For example, DHFR is a selectable gene which is necessary for cell survival in the presence of MTX in the culture medium. The gene is essential for growth in the absence of hypoxanthine and thymidine. If the endogenous DHFR selectable gene is eliminated, cells are able to grow in the absence of hypoxanthine and thymidine if they are given an exogenous copy of the DHFR gene. This exogenous copy of the DHFR gene is a selectable marker but is not a selectable gene. An amplifiable locus comprises a selectable gene and a target site. A target site is found outside of a selectable gene such that a selectable gene does not comprise a target site. Examples of selectable genes are given in Table 1.

As used herein, when used in connection with the position of a target site, recognition sequence, or inserted sequence of interest relative to the position of a selectable gene, the term "proximal" means that the target site, recognition sequence, or inserted sequence of interest is within the same amplifiable locus as the selectable gene, either upstream (5') or downstream (3') of the selectable gene, and preferably between the selectable gene and the next gene in the region (whether upstream (5') or downstream (3')). Typically, a "proximal" target site, recognition sequence, or inserted sequence of interest will be within <100,000 base pairs of the selectable gene, as measured from the first or last nucleotide of the first or last regulatory element of the selectable gene.

As used herein, the term "homologous recombination" refers to the natural, cellular process in which a double-stranded DNA-break is repaired using a homologous DNA sequence as the repair template (see, e.g. Cahill et al. (2006), *Front. Biosci.* 11:1958-1976). The homologous DNA sequence may be an endogenous chromosomal sequence or an exogenous nucleic acid that was delivered to the cell. Thus, for some applications of engineered meganucleases, a meganuclease is used to cleave a recognition sequence within a target sequence in a genome and an exogenous nucleic acid with homology to or substantial sequence similarity with the target sequence is delivered into the cell and used as a template for repair by homologous recombination. The DNA sequence of the exogenous nucleic acid, which may differ significantly from the target sequence, is thereby inserted or incorporated into the chromosomal sequence. The process of homologous recombination occurs primarily in eukaryotic organisms. The term "homology" is used herein as equivalent to "sequence similarity" and is not intended to require identity by descent or phylogenetic relatedness.

As used herein, the term "stably integrated" means that an exogenous or heterologous DNA sequence has been covlently inserted into a chromosome (e.g., by homologous recombination, non-homologous end joining, transposition, etc.) and has remained in the chromosome for a period of at least 8 weeks.&&

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end-joining is error-prone and frequently results in the untemplated addition or deletion of DNA sequences at the site of repair. Thus, for certain applications, an engineered meganuclease can be used to produce a double-stranded break at a meganuclease recognition sequence within an amplifiable locus and an exogenous nucleic acid molecule, such as a PCR product, can be captured at the site of the DNA break by NHEJ (see, e.g. Salomon et al. (1998), *EMBO J.* 17:6086-6095). In such cases, the exogenous nucleic acid may or may not have homology to the target sequence. The process of non-homologous end-joining occurs in both eukaryotes and prokaryotes such as bacteria.

As used herein, the term "sequence of interest" means any nucleic acid sequence, whether it codes for a protein, RNA, or regulatory element (e.g., an enhancer, silencer, or promoter sequence), that can be inserted into a genome or used to replace a genomic DNA sequence. Sequences of interest can have heterologous DNA sequences that allow for tagging a protein or RNA that is expressed from the sequence of interest. For instance, a protein can be tagged with tags including, but not limited to, an epitope (e.g., c-myc, FLAG) or other ligand (e.g., poly-His). Furthermore, a sequence of interest can encode a fusion protein, according to techniques known in the art (see, e.g., Ausubel et al., *Current Protocols in Molecular Biology*, Wiley 1999). In preferred embodiments, a sequence of interest comprises a promoter operably linked to a gene encoding a protein of medicinal value such as an antibody, antibody fragment, cytokine, growth factor, hormone, or enzyme. For some applications, the sequence of interest is flanked by a DNA sequence that is recognized by the engineered meganuclease for cleavage. Thus, the flanking sequences are cleaved allowing for proper insertion of the sequence of interest into genomic recognition sequences cleaved by an engineered meganuclease. For some applications, the sequence of interest is flanked by DNA sequences with homology to or substantial sequence similarity with the target site such that homologous recombination inserts the sequence of interest within the genome at the locus of the target sequence.

As used herein, the term "donor DNA" refers to a DNA molecule comprising a sequence of interest flanked by DNA sequences homologous to a target site. Donor DNA can serve as a template for DNA repair by homologous recombination if it is delivered to a cell with a site-specific nuclease such as a meganuclease, zinc-finger nuclease, or TAL-effector nuclease. The result of such DNA repair is the insertion of the sequence of interest into the chromosomal DNA of the cell. Donor DNA can be linear, such as a PCR product, or circular, such as a plasmid. In cases where a donor DNA is a circular plasmid, it may be referred to as a "donor plasmid."

As used herein, unless specifically indicated otherwise, the word "or" is used in the inclusive sense of "and/or" and not the exclusive sense of "either/or."

2.1 Transgene Targeting to Amplifiable Loci

The present invention provides methods for generating transgenic mammalian cell lines expressing a desired protein product of interest, including "high-producer" cell lines, by targeting the insertion of a gene encoding the protein product of interest (e.g., a therapeutic protein gene expression cassette) to regions of the genome that are amplifiable. Such regions in mammalian cells include the DHFR, GS, and HPRT genes, as well as others shown in Table 1.

The precise mechanism of gene amplification is not known. Indeed, it is very likely that there is no single mechanism by which gene amplification occurs but that a variety of different random chromosomal aberrations, in combination with strong selection for amplification, results in increased gene copy number (reviewed in Omasa (2002), *J. Biosci. Bioeng.* 94:600-605). It is clear that chromosomal location plays a major role in amplification and the stable maintenance of amplified genes (Brinton and Heintz (1995), *Chromosoma* 104:143-51). It has been found that transgenes integrated into chromosomal locations adjacent to telomeres are more easily amplified and, once amplified, tend to be stable at high copy numbers after the selection agent is removed (Yoshikawa et al. (2000), *Cytotechnology* 33:37-46; Yoshikawa et al. (2000), *Biotechnol Frog.* 16:710-715). This is significant because selection agents such as MTX and MSX are toxic and cannot be included in the growth media in a commercial biomanufacturing process. In contrast, transgenes integrated into regions in the CHO genome that are not adjacent to telomeres amplify inefficiently and rapidly lose copy number following the removal of selection agents from the media. For example, Yoshikawa et al. found that randomly-integrated transgenes linked to a DHFR selectable marker amplified to greater than 10-fold higher copy numbers when the integration site was adjacent to a telomere (Yoshikawa et al. (2000), *Biotechnol Frog.* 16:710-715). These researchers also found that an amplified transgene integrated into a non-telomeric region will lose >50% of its copies in only 20 days following the removal of MTX from the growth media. None of the selectable genes identified in Table 1 is adjacent to a telomere in the mouse genome (www.ensembl.com) and the similarity in genome organization between mouse and CHO makes it likely that these genes are in non-telomeric regions in CHO as well (Xu et al. (2011), *Nat. Biotechnol.* 29:735-741). Thus, the prior art instructs that the loci identified in Table 1, including the DHFR and GS loci, are not preferred locations to target transgene insertion if the goal is efficient and stable gene amplification.

In addition, in the case of endogenous gene amplification, it is clear that chromosomal sequences outside of the selectable gene sequence play an important role in facilitating amplification and in defining the length of DNA sequence that is co-amplified with the gene under selection (Looney and Hamlin (1987), *Mol. and Cell. Biol.* 7:569-577). In particular, it has been shown that the sequence and location of the DNA replication origin in relation to the selectable gene plays a major role in amplification. For example, it has been shown that amplification of the endogenous CHO DHFR locus is dependent upon a pair of replication origins found in the region 5,000-60,000 base pairs downstream of the DHFR gene coding sequence (Anachkova and Hamlin (1989), *Mol. and Cell. Biol.* 9:532-540; Milbrandt et al. (1981), *Proc. Natl. Acad. Sci. USA* 78:6042-6047). Further, Brinton and Heintz have shown that these same replication origins fail to promote gene amplification when incorporated randomly into the genome with a transgenic DHFR sequence (Brinton and Heintz (1995), *Chromosoma.* 104:

143-51). This clearly demonstrates the importance of maintaining both the sequence and proper chromosomal context of these replication origins to promote DHFR gene amplification. Thus the art instructs that the region downstream of DHFR is critical to gene amplification and should not be disrupted by, for example, inserting a transgenic gene expression cassette as described in the present invention.

Surprisingly, we have discovered that DNA sequences, including exogenous transcriptionally active sequences, which are inserted proximal to (e.g., within <100,000 base pairs) selectable genes in mammalian cell lines (e.g., CHO-K1) will co-amplify in the presence of appropriate compounds which select for amplification. Thus, the present invention provides methods for reliably and reproducibly producing isogenic cell lines in which transgenes encoding protein products of interest (e.g., biotherapeutic gene expression cassettes) can be amplified but in which it is not necessary to screen a large number of randomly generated cell lines to identify those which express high levels of the protein product of interest and are resistant to gene silencing.

In addition, we have surprisingly found that the mammalian cell lines of the invention, in which a sequence of interest is co-amplified with a selectable gene in an amplifiable locus, are stable with respect to expression of the sequence of interest and/or copy number of the sequence of interest even in the absence of continued selection. That is, whereas the art teaches that amplified sequences will be reduced in copy number over time if selection is not maintained (see, e.g., Yoshikawa et al. (2000), *Biotechnol Prog.* 16:710-715), we have found that cell lines produced according to the methods of the invention continue to produce the protein products of interest (encoded by the sequences of interest) at levels within 20%-25% of the initial levels, even 14 weeks after removal of the selection agent. This is significant, as noted above, because selection agents such as MTX and MSX are toxic, and it would be highly desirable to produce biotherapeutic proteins in cell lines which do not require continued exposure to such selection agents. Therefore, in some embodiments, the invention provides recombinant mammalian cell lines which continue to express a protein product of interest from an exogenous sequence of interest present in an amplified region of the genome (i.e., present in 2-1,000 copies, co-amplified with a selectable gene in an amplifiable locus) for a period of at least 8, 9, 10, 11, 12, 13, or 14 weeks after removal of the amplification selection agent, and with a reduction of expression levels and/or copy number of less than 20, 25, 30, 35 or 40%.

The present invention also provides the products necessary to practice the methods, and to target insertion of sequences of interest into amplifiable loci in mammalian cell lines. A common method for inserting or modifying a DNA sequence involves introducing a transgenic DNA sequence flanked by sequences homologous to the genomic target and selecting or screening for a successful homologous recombination event. Recombination with the transgenic DNA occurs rarely but can be stimulated by a double-stranded break in the genomic DNA at the target site (Porteus et al. (2005), *Nat. Biotechnol.* 23: 967-73; Tzfira et al. (2005), *Trends Biotechnol.* 23: 567-9; McDaniel et al. (2005), *Curr. Opin. Biotechnol.* 16: 476-83). Numerous methods have been employed to create DNA double-stranded breaks, including irradiation and chemical treatments. Although these methods efficiently stimulate recombination, the double-stranded breaks are randomly dispersed in the genome, which can be highly mutagenic and toxic. At present, the inability to target gene modifications to unique sites within a chromosomal background is a major impediment to routine genome engineering.

One approach to achieving this goal is stimulating homologous recombination at a double-stranded break in a target locus using a nuclease with specificity for a sequence that is sufficiently large to be present at only a single site within the genome (see, e.g., Porteus et al. (2005), *Nat. Biotechnol.* 23: 967-73). The effectiveness of this strategy has been demonstrated in a variety of organisms using ZFNs (Porteus (2006), *Mol Ther* 13: 438-46; Wright et al. (2005), *Plant J.* 44: 693-705; Urnov et al. (2005), *Nature* 435: 646-51). Homing endonucleases are a group of naturally-occurring nucleases which recognize 15-40 base-pair cleavage sites commonly found in the genomes of plants and fungi. They are frequently associated with parasitic DNA elements, such as Group I self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG (SEQ ID NO: 65) family, the GIY-YIG family, the His-Cys box family and the HNH family. These families are characterized by structural motifs, which affect catalytic activity and recognition sequence. For instance, members of the LAGLIDADG (SEQ ID NO: 65) family are characterized by having either one or two copies of the conserved LAGLIDADG (SEQ ID NO: 65) motif (see Chevalier et al. (2001), *Nucleic Acids Res.* 29(18): 3757-3774). The LAGLIDADG (SEQ ID NO: 65) homing endonucleases with a single copy of the LAGLIDADG (SEQ ID NO: 65) motif form homodimers, whereas members with two copies of the LAGLIDADG (SEQ ID NO: 65) motif are found as monomers.

Natural homing endonucleases, primarily from the LAGLIDADG (SEQ ID NO: 65) family, have been used to effectively promote site-specific genome modification in plants, yeast, *Drosophila*, mammalian cells and mice, but this approach has been limited to the modification of either homologous genes that conserve the endonuclease recognition sequence (Monnat et al. (1999), *Biochem. Biophys. Res. Commun.* 255: 88-93) or to pre-engineered genomes into which a recognition sequence has been introduced (Rouet et al. (1994), *Mol. Cell. Biol.* 14: 8096-106; Chilton et al. (2003), *Plant Physiol.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622).

Systematic implementation of nuclease-stimulated gene modification requires the use of engineered enzymes with customized specificities to target DNA breaks to existing sites in a genome and, therefore, there has been great interest in adapting homing endonucleases to promote gene modifications at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62).

I-CreI (SEQ ID NO: 1) is a member of the LAGLIDADG (SEQ ID NO: 65) family of homing endonucleases which recognizes and cuts a 22 base pair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). More recently, a method of rationallydesigning mono-LAGLIDADG (SEQ ID NO: 65) homing endonucleases was described which is capable of comprehensively redesigning I-CreI and other homing endonucleases to target widely-divergent DNA sites, including sites in mammalian, yeast, plant, bacterial, and viral genomes (WO 2007/047859).

Thus, in one embodiment, the invention provides engineered meganucleases derived from the amino acid sequence of I-CreI that recognize and cut DNA sites in amplifiable regions of mammalian genomes. These engineered meganucleases can be used in accordance with the invention to target the insertion of gene expression cassettes into defined locations in the chromosomal DNA of cell lines such as CHO cells. This invention will greatly streamline the production of desired cell lines by reducing the number of lines that must be screened to identify a "high-producer" clone suitable for commercial-scale production of a therapeutic glycoprotein.

The present invention involves targeting transgenic DNA "sequences of interest" to amplifiable loci. The amplifiable loci are regions of the chromosomal DNA that contain selectable genes that become amplified in the presence of selection agents (e.g., drugs). For example, the Chinese Hamster Ovary (CHO) cell DHFR locus can be amplified to ~1,000 copies by growing the cells in the presence of methotrexate (MTX), a DHFR inhibitor. Table 1 lists additional examples of selectable genes that can be amplified using small molecule drugs (Kellems, ed. *Gene amplification in mammalian cells: a comprehensive guide*. Marcel Dekker, New York, 1993; Omasa (2002), *J. Biosci. Bioeng.* 94:6 600-605).

TABLE 1

Amplifiable Genes

| Selectable Gene Name | Amplified With |
| --- | --- |
| Dihydrofolate Reductase | Methotrexate (MTX) |
| Glutamine Synthetase | Methionine sulphoximine (MSX) |
| Hypoxanthine Phosphoribosyltransferase | Aminopterin, hypoxanthine, and thymidine |
| Threonyl tRNA Synthetase | Borrelidin |
| Na, K-ATPase | Ouabain |
| Asparagine Synthetase | Albizziin or Beta-aspartyl hydroxamate |
| Ornithine Decarboxylase | alpha-difluoromethylornithine (DFMO) |
| Inosine-5'-monophosphate dehydrogenase | Mycophenolic Acid |
| Adenosine Deaminase | Adenosine, Alanosine, 2'deoxycoformycin |
| Thymidylate Synthetase | Fluorouracil |
| Aspartate Transcarbamylase | N-Phosphonacetyl-L-Aspartate (PALA) |
| Metallothionein | Cadmium |
| Adenylate Deaminase (1,2) | Adenine, Azaserine, Coformycin |
| UMP-Synthetase | 6-azauridine, pyrazofuran |
| Ribonucleotide Reductase | hydroxyurea, motexafin gadolinium, fludarabine, cladribine, gemcitabine, tezacitabine, triapine. |

Several considerations must be taken into account when selecting a specific target site for the insertion of a sequence of interest within an amplifiable locus. First, the selected insertion site must be co-amplified with the gene under selection. In many cases, experimental data already exists in the art which delimits the amount of flanking chromosomal sequence that co-amplifies with a selectable gene of interest. This data, which precisely defines the extent of the amplifiable locus, exists for CHO DHFR (Ma et al. (1988), *Mol Cell Biol.* 8(6):2316-27), human DHFR (Morales et al. (2009), *Mol Cancer Ther.* 8(2):424-432), and CHO GS (Sanders et al. (1987), *Dev Biol Stand.* 66:55-63). Where such data does not already exist in the art, we predict that chromosomal DNA sequences <100,000 base pairs upstream or downstream of the selectable gene coding sequence are likely to co-amplify. Hence, these regions could be suitable sites for targeting the insertion of a sequence of interest.

Second, target sites should be selected which will not greatly impact the function of the selectable gene (e.g., the endogenous DHFR, GS, or HPRT gene). Because amplification requires a functional copy of the selectable gene, insertion sites within the promoter, exons, introns, polyadenylation signals, or other regulatory sequences that, if disrupted, would greatly impact transcription or translation of the selectable gene, should be avoided. For example, WO 2008/059317 discloses meganucleases which cleave DNA target sites within the HPRT gene. To the extent WO 2008/059317 discloses the insertion of genes into the HPRT locus, it teaches that the HPRT gene coding sequence should be disrupted in the process of transgene insertion to facilitate selection for proper targeting using 6-thioguanine. 6-thioguanine is a toxic nucleotide analog that kills cells having functional HPRT activity. Because cells produced in accordance with WO 2008/059317 will not have HPRT activity, they will not amplify an inserted transgene in response to treatment with an HPRT inhibitor and, so, cannot be used in the present invention. For the present invention, unless the precise limits of all regulatory sequences are already known for a particular selectable gene, insertion sites >1,000 base pairs, >2,000 base pairs, >3,000 base pairs, >4,000 base pairs, or, preferably, >5,000 base pairs, upstream or downstream of the gene coding sequence should be selected. However, if the location of the regulatory sequences are known, the sequence of interest can be inserted immediately adjacent to the either the most 5' or 3' regulatory sequence (e.g., immediately 3' to the polyadenylation signal).

Lastly, target sites should be selected which do not disrupt other chromosomal genes which may be important for normal cell physiology. In general, gene insertion sites should be >1,000 base pairs, >2,000 base pairs, >3,000 base pairs, >4,000 base pairs, or, preferably, >5,000 base pairs, away from any gene coding sequence.

Various methods of the invention are described schematically in the figures as follows:

FIG. 1 depicts a general strategy for targeting a sequence of interest to an amplifiable locus. In the first step, a site-specific endonuclease introduces a double-stranded break in the chromosomal DNA of a cell at a site that is proximal to an endogenous selectable gene. The cleaved chromosomal DNA then undergoes homologous recombination with a donor DNA molecule comprising a sequence of interest flanked by DNA sequences homologous to sequences flanking the endonuclease recognition sequence in the target site. As a result, the sequence of interest is inserted into the chromosomal DNA of the cell adjacent to the endogenous selectable gene. The modified cell is then grown in the presence of one or more compounds that inhibit the function of the selectable gene to induce an increase in the copy number (i.e., amplification) of the selectable gene. The sequence of interest, which is genetically linked to the selectable gene, will co-amplify with the selectable gene. The result is a stable transgenic cell line comprising multiple copies of the sequence of interest.

Figure 2:
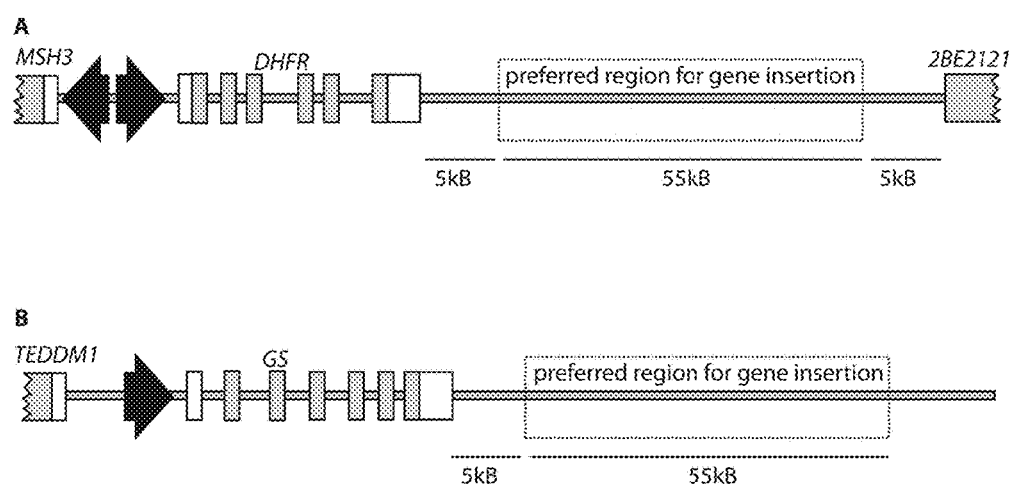
FIGS. 2A and 2B. (A) Schematic of the CHO DHFR locus showing a preferred region for targeting a sequence of interest 5,000-60,000 base pairs downstream of the DHFR gene. (B) Schematic of the CHO GS locus showing a preferred region for targeting a sequence of interest 5,000-55,000 base pairs downstream of the GS gene.

FIG. 2(A) depicts a schematic of the CHO DHFR locus showing a preferred region for targeting a sequence of interest 5,000-60,000 base pairs downstream of the DHFR gene. FIG. 2(B) depicts a schematic of the CHO GS locus showing a preferred region for targeting a sequence of interest 5,000-55,000 base pairs downstream of the GS gene.

Promoters are shown as arrows. Exons are shown as rectangles, with non-coding exons in white and protein coding exons in gray.

Figure 3:
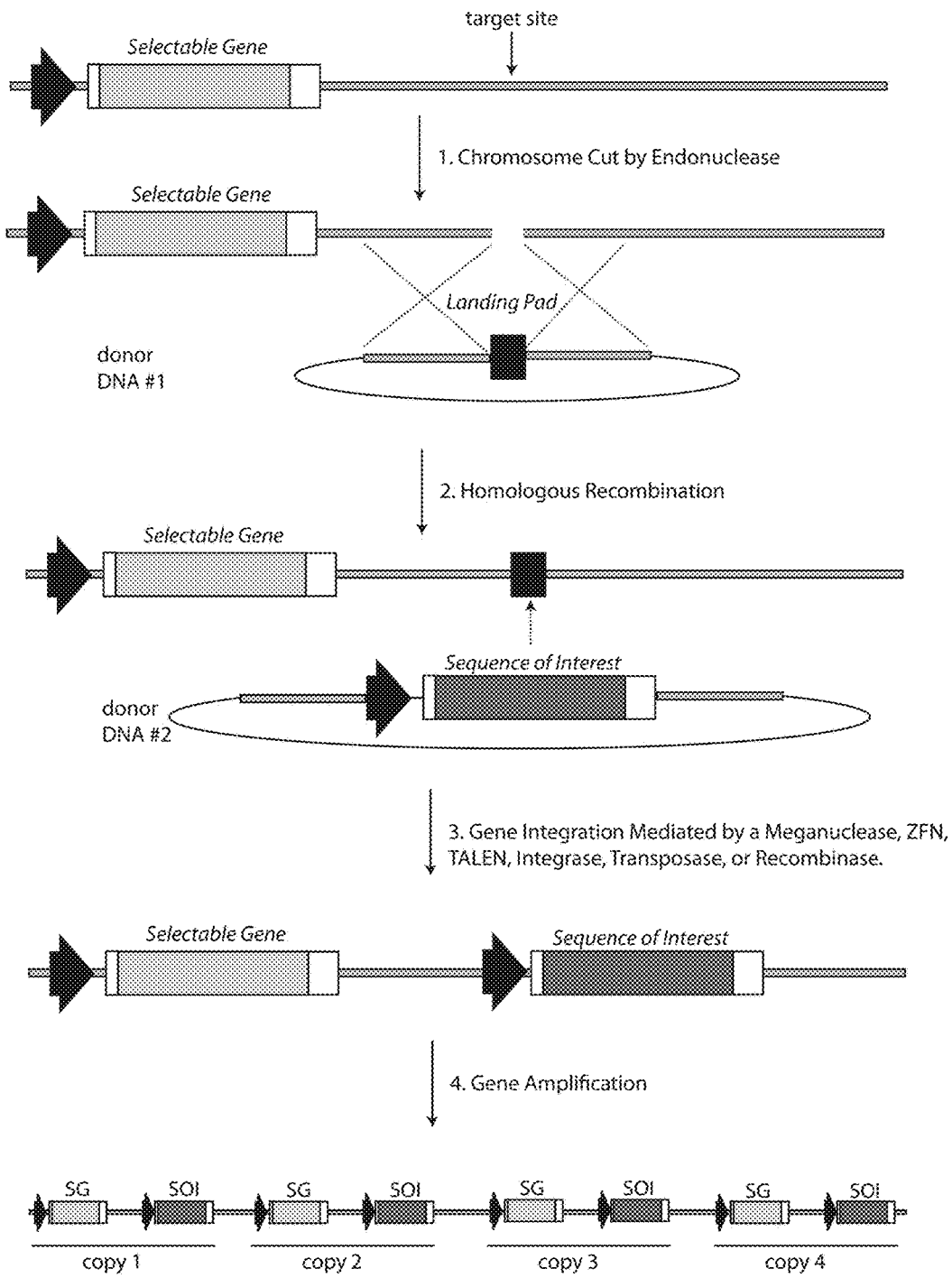
FIG. 3. Strategy for inserting a sequence of interest into an amplifiable locus in a two-step process involving a pre-integrated engineered target sequence.

FIG. 3 depicts a strategy for inserting a sequence of interest into an amplifiable locus in a two-step process involving a pre-integrated target sequence. In the first step, the chromosomal DNA of a cell is cleaved by a site-specific endonuclease at a site that is proximal to a selectable gene. The cleaved chromosomal DNA then undergoes homologous recombination with a donor DNA molecule comprising an exogenous target sequence flanked by DNA sequences homologous to the sequences flanking the endogenous target site. This results in the insertion of the new engineered target sequence into the chromosomal DNA of the cell proximal to the selectable gene. A sequence of interest can subsequently be targeted proximal to the same selectable gene using a nuclease, integrase, transposase, or recombinase that specifically recognizes the pre-integrated engineered target sequence. The modified cell is then grown in the presence of one or more compounds that co-amplify the selectable gene and the sequence of interest.

Figure 4:
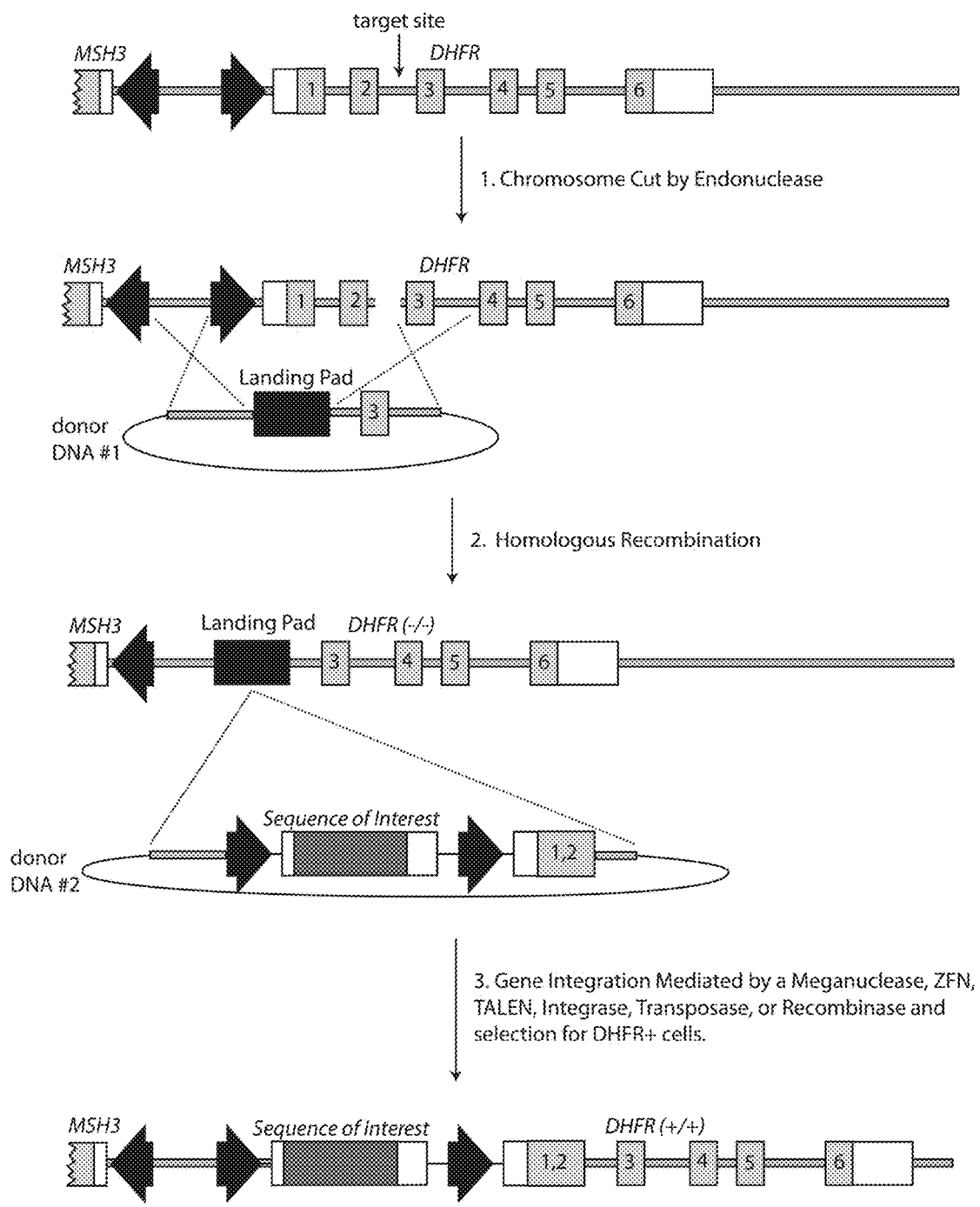
FIG. 4. Strategy for inserting an engineered target sequence into an amplifiable locus with concomitant removal of a portion of the selectable gene, followed by insertion of a sequence of interest and reconstitution of the selectable gene.

FIG. 4 depicts a strategy for inserting an engineered target sequence into a selectable gene (e.g., DHFR) with concomitant removal of a portion of the selectable gene. A site-specific endonuclease is first used to cleave the chromosomal DNA of the cell proximal to or within the selectable gene sequence. As shown in the figure, the endogenous target site is between exons 2 and 3 of the CHO DHFR gene (although the target site could be within any intron or exon, and the selectable gene could be any gene subject to amplification). The chromosomal DNA then undergoes homologous recombination with a first donor DNA ("donor DNA #1") such that the sequence of the first donor DNA is inserted into the chromosomal DNA of the cell. As shown in the figure, this results in the replacement of the promoter and first two exons of DHFR by the new engineered target sequence (although the first donor DNA could replace more or less of the chromosomal DNA, such as only a portion of one exon). If such a replacement is made to all DHFR alleles in a cell, the resultant cell line is DHFR (−/−). A sequence of interest can subsequently be targeted proximal to the selectable gene in the cell line using an endonuclease, integrase, transposase, or recombinase that recognizes the engineered target sequence. As shown in the figure, the second donor DNA ("donor DNA #2") comprises a sequence of interest as well as a promoter and the first two exons of DHFR. Proper targeting of this second donor DNA molecule results in the insertion of the sequence of interest at the engineered target sequence while simultaneously reconstituting a functional DHFR gene. Thus, properly targeted cell lines will be DHFR+ and can be selected using media deficient in hypoxanthine/thymidine. In addition, the sequence of interest can be co-amplified with the DHFR gene using MTX selection. The strategy diagrammed here for DHFR can be applied to any selectable gene in an amplifiable locus.

Figure 5:
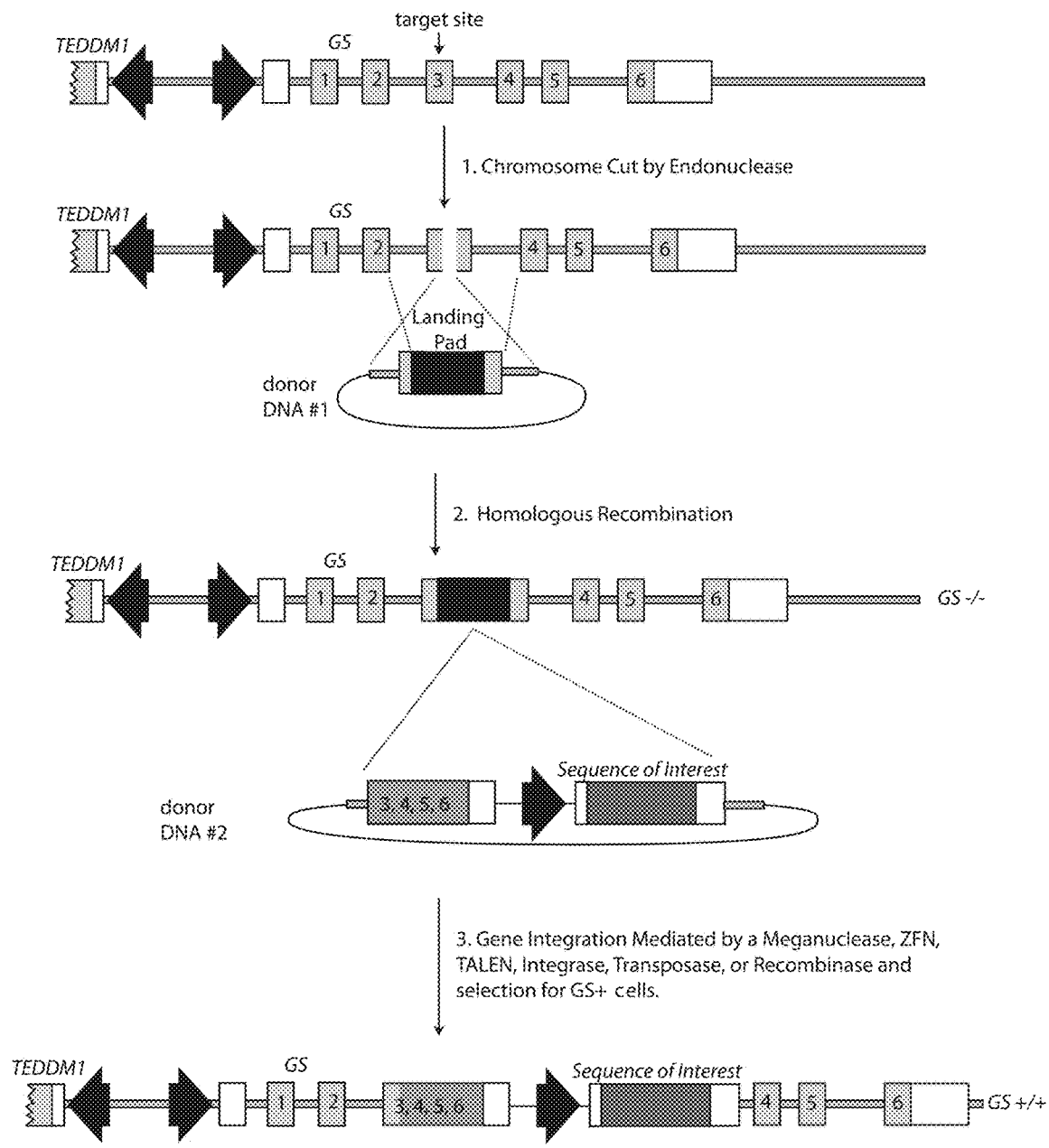
FIG. 5. Strategy for inserting an engineered target sequence into an amplifiable locus with concomitant disruption of the coding sequence of a selectable gene, followed by insertion of a sequence of interest and reconstitution of the selectable gene.

FIG. 5 depicts a strategy for inserting an engineered target sequence into an amplifiable locus with concomitant disruption of the coding sequence of a selectable gene. A site-specific endonuclease is first used to cleave the chromosomal DNA of the cell within the selectable gene coding sequence. As shown in the figure, the endogenous target site is in the third exon of the CHO GS gene. The chromosomal DNA then undergoes homologous recombination with a first donor DNA ("donor DNA #1") such that the sequence of the first donor DNA is inserted into the chromosomal DNA of the cell. This results in the insertion of a new engineered target sequence into the GS coding sequence. If such an insertion occurs in both alleles of the GS gene and results in a frameshift mutation or otherwise disrupts the function of the GS gene, the resultant cell line will be GS (−/−). A sequence of interest can subsequently be targeted proximal to the amplifiable locus in the cell line using an endonuclease, integrase, transposase, or recombinase that recognizes the engineered target sequence. As shown in the figure, a second donor DNA ("donor DNA #2") comprises a sequence of interest operably linked to a promoter as well as the 3' portion of the GS coding sequence comprising exons 3, 4, 5, and 6. (The figure shows exons 3, 4, 5, and 6 joined into a single nucleotide sequence (i.e., with introns removed), but a sequence including either the naturally-occurring introns or one or more artificial introns could also be employed). Proper targeting of the second donor DNA molecule results in the insertion of the sequence of interest at the engineered target sequence while simultaneously reconstituting a functional GS gene. Thus, properly targeted cell lines will be GS+ and can be selected using media deficient in L-glutamine. In addition, the sequence of interest can be co-amplified with the GS gene using MSX selection. The strategy diagrammed here for GS can be applied to any selectable gene in an amplifiable locus.

Figure 6:
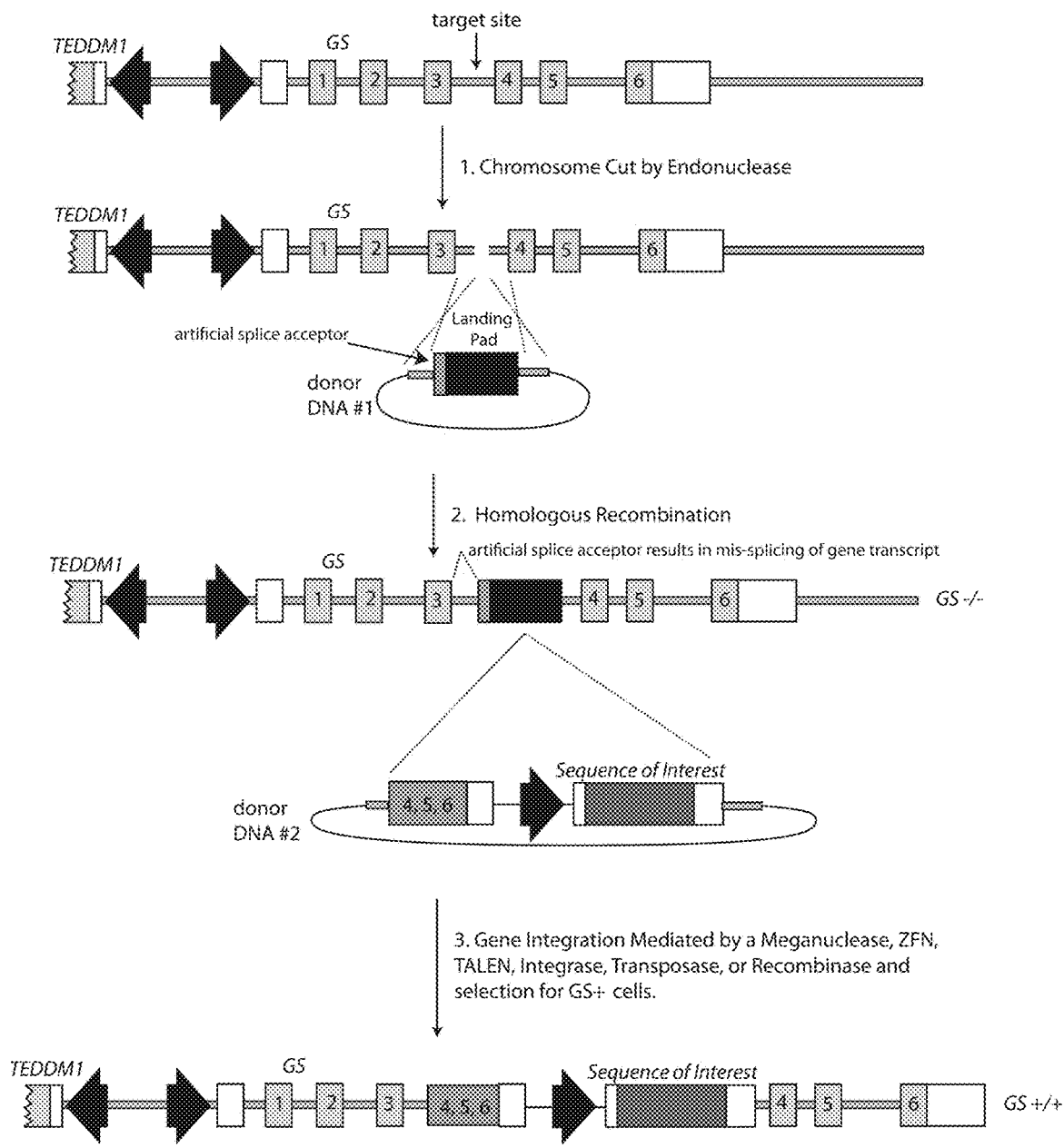
FIG. 6. Strategy for inserting an engineered target sequence into an amplifiable locus with concomitant disruption of the mRNA processing, followed by insertion of a sequence of interest and reconstitution of the selectable gene.

FIG. 6 depicts a strategy for inserting an engineered target sequence into an amplifiable locus with concomitant disruption of the mRNA processing of a selectable gene. A site-specific endonuclease is first used to cleave the chromosomal DNA of the cell within an intron in the selectable gene. As drawn, the endogenous target site is in the intron between the third and fourth coding exons of the CHO GS gene. The chromosomal DNA then undergoes homologous recombination with a donor DNA #1 such that the sequence of the donor DNA is inserted in the chromosomal DNA of the cell. This results in the insertion of a new engineered target sequence into the GS coding sequence with an additional sequence that causes the GS mRNA to be processed incorrectly. As drawn, this additional sequence comprises a strong splice acceptor. If such an insertion occurs in both alleles of the GS gene, the artificial splice acceptor will cause the GS mRNA to splice incorrectly, resulting in a loss of GS expression and a requirement for growth in media containing L-glutamine. A sequence of interest can subsequently be targeted to the amplifiable locus in the cell line using an endonuclease, integrase, transposase, or recombinase that recognizes the engineered target sequence. As diagrammed, donor DNA #2 comprises a sequence of interest operably linked to a promoter as well as the 3' portion of the GS coding sequence comprising exons 4, 5, and 6 joined into a single nucleotide sequence. (The figure shows exons 4, 5, and 6 joined into a single nucleotide sequence (i.e., with introns removed), but a sequence including either the naturally-occurring introns or one or more artificial introns could also be employed). Proper targeting of this donor DNA #2 molecule results in the insertion of the sequence of interest at the engineered target sequence while simultaneously reconstituting a functional GS gene. Thus, properly targeted cell lines will be GS+ and can be selected using media deficient in L-glutamine and the sequence of interest can be co-amplified with the GS gene using MSX selection. The strategy diagrammed here for GS can be applied to any selectable gene in an amplifiable locus.

Figures 7A, 7B, 7C, 7D:
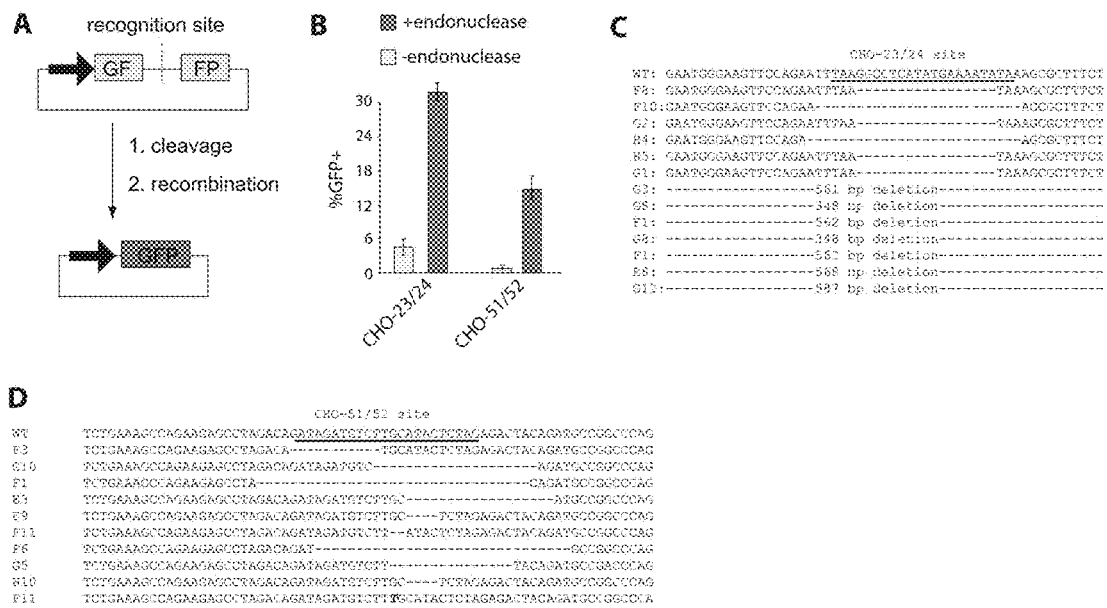
FIGS. 7A through 7D. (A) A direct-repeat recombination assay for site-specific endonuclease activity. (B) Results of the assay in (A) applied to the CHO-23/24 and CHO-51/52 meganucleases. (C) Alignment of sequences obtained from CHO cells transfected with mRNA encoding the CHO-23/24 meganuclease (SEQ ID NOS 37-39, 38, 40, 38, and 38, respectively, in order of appearance). (D) Alignment of sequences obtained from CHO cells transfected with mRNA encoding the CHO-51/52 meganuclease (SEQ ID NOS 41-51, respectively, in order of appearance).

FIG. 7(A) depicts a direct-repeat recombination assay for site-specific endonuclease activity. A reporter plasmid is produced comprising the 5' two-thirds of the GFP gene ("GF"), followed by an endonuclease recognition sequence, followed by the 3' two-thirds of the GFP gene ("FP").

Mammalian cells are transfected with this reporter plasmid as well as a gene encoding an endonuclease. Cleavage of the recognition sequence by the endonuclease stimulates homologous recombination between direct repeats of the GFP gene to restore GFP function. GFP+ cells can then be counted and/or sorted on a flow cytometer.

FIG. 7(B) depicts the results of the assay of FIG. 7(A) as applied to the CHO-23/24 and CHO-51/52 meganucleases. Light bars indicate the percentage of GFP+ cells when cells are transfected with the reporter plasmid alone (−endonuclease). Dark bars indicate the percentage of GFP+ cells when cells are co-transfected with a reporter plasmid and the corresponding meganuclease gene (+endonuclease). The assay was performed in triplicate and the standard deviation is shown.

FIG. 7(C) depicts alignment of sequences obtained from CHO cells transfected with mRNA encoding the CHO-23/24 meganuclease. The top sequence is from a wild-type (WT) CHO cell with the recognition sequence for CHO-23/24 underlined.

FIG. 7(D) depicts alignment of sequences obtained from CHO cells transfected with mRNA encoding the CHO-51/52 meganuclease. The top sequence is from a wild-type (WT) CHO cell with the recognition sequence for CHO-51/52 underlined.

Figure 8:
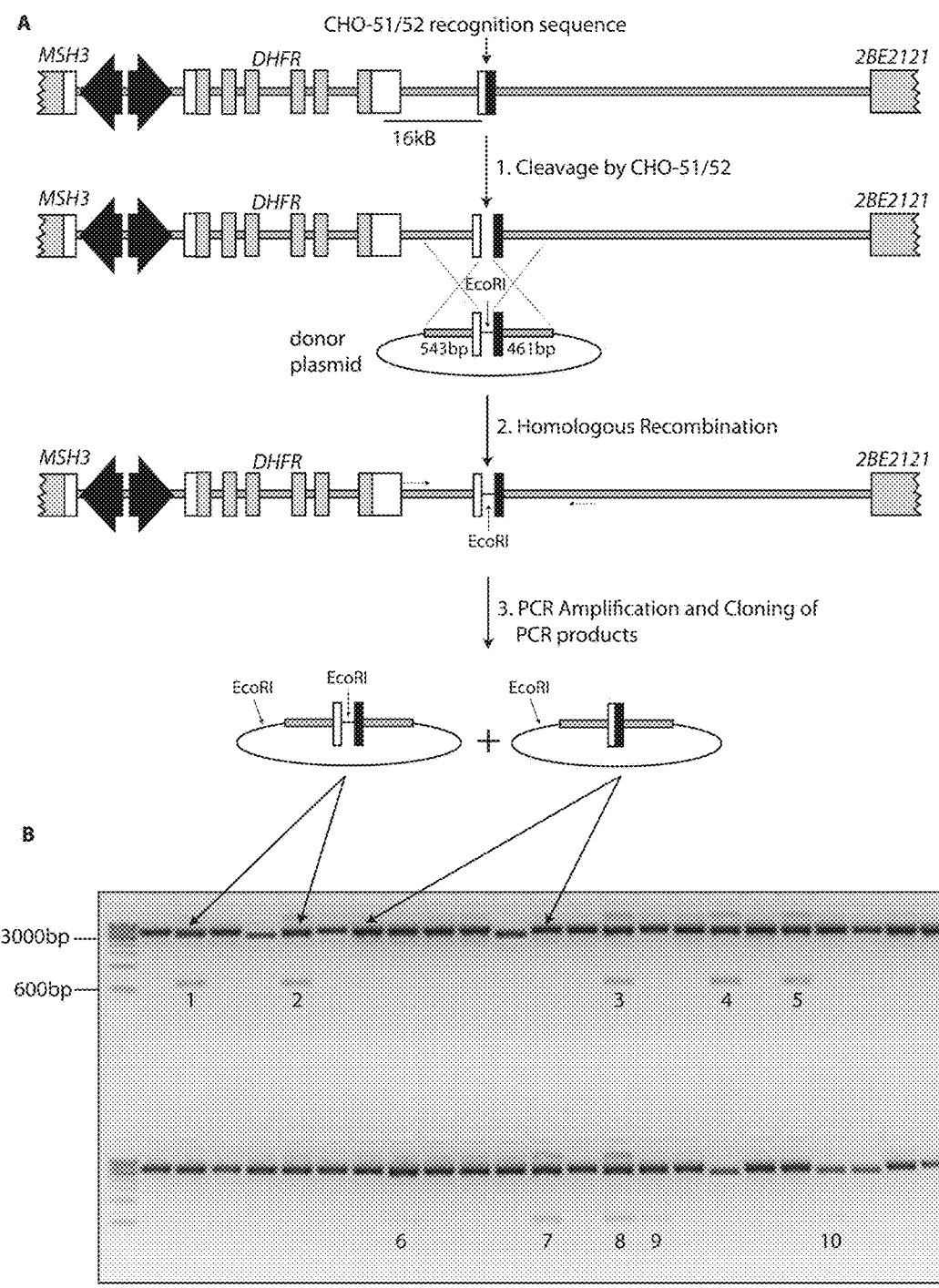
FIGS. 8A and 8B. (A) Strategy for inserting an exogenous DNA sequence into the CHO DHFR locus using the CHO-51/52 meganuclease. (B) PCR products demonstrating insertion of an engineered target sequence.

FIG. 8(A) depicts a strategy for inserting an exogenous DNA sequence into the CHO DHFR locus using the CHO-51/52 meganuclease. CHO cells were co-transfected with mRNA encoding CHO-51/52 and a donor plasmid comprising an EcoRI site flanked by 543 base pairs of DNA sequence homologous to the region upstream of the CHO-51/52 recognition site and 461 base pairs of DNA sequence homologous to the region downstream of the CHO-51/52 recognition site. 48 hours post-transfection, genomic DNA was isolated and subjected to PCR using primers specific for the downstream region of the DHFR locus (dashed arrows).

FIG. 8(B) depicts PCR products that were cloned into pUC-19 and 48 individual plasmid clones and were digested with EcoRI and visualized on an agarose gel. 10 plasmids (numbered lanes) yielded a 647 base pair restriction fragment, consistent with cleavage of a first EcoRI site within the pUC-19 vector and a second EcoRI site in the cloned PCR fragment. These 10 plasmids were sequenced to confirm that they harbor a PCR fragment comprising a portion of the downstream DHFR locus with an EcoRI restriction site inserted into the CHO-51/52 recognition sequence. This restriction pattern was not observed when CHO cells were transfected with the donor plasmid alone.

FIG. 9(A) depicts a strategy for inserting an engineered target sequence into the CHO DHFR locus using the CHO-23/24 meganuclease. CHO cells were co-transfected with mRNA encoding CHO-23/24 and a donor plasmid comprising, in 5' to 3' orientation, an SV40 promoter, an ATG start codon, an FRT site, and a ZEOCIN™-resistance (Zeo) gene. ZEOCIN™-resistant cells were cloned by limiting dilution and screened by PCR to identify a clonal cell line in which the donor plasmid sequence integrated into the CHO-23/24 recognition site. After expansion, this cell line was co-transfected with a first plasmid encoding Flp recombinase operably linked to a promoter and second plasmid (donor plasmid #2) comprising a GFP gene under the control of a CMV promoter, an FRT site, and a hygromycin-resistance (Hyg) gene lacking a start codon. Flp-mediated recombination between FRT sites resulted in the integration of the donor plasmid #2 sequence into the engineered target sequence (i.e., the FRT site) such that a functional Hyg gene expression cassette was produced. FIG. 9(B) depicts PCR products from hygromycin-resistant clones produced as in (A) that were cloned by limiting dilution. Genomic DNA was extracted from 24 individual clones and PCR amplified using a first primer in the DHFR locus and a second primer in the Hyg gene (dashed lines). All 24 clones yielded a PCR product consistent with Hyg gene insertion into the engineered target sequence. FIG. 9(C) depicts GFP expression by the 24 clones produced in (B) using flow cytometry. All clones were found to express high levels of GFP with relatively little clone-to-clone variability.

Figure 9:
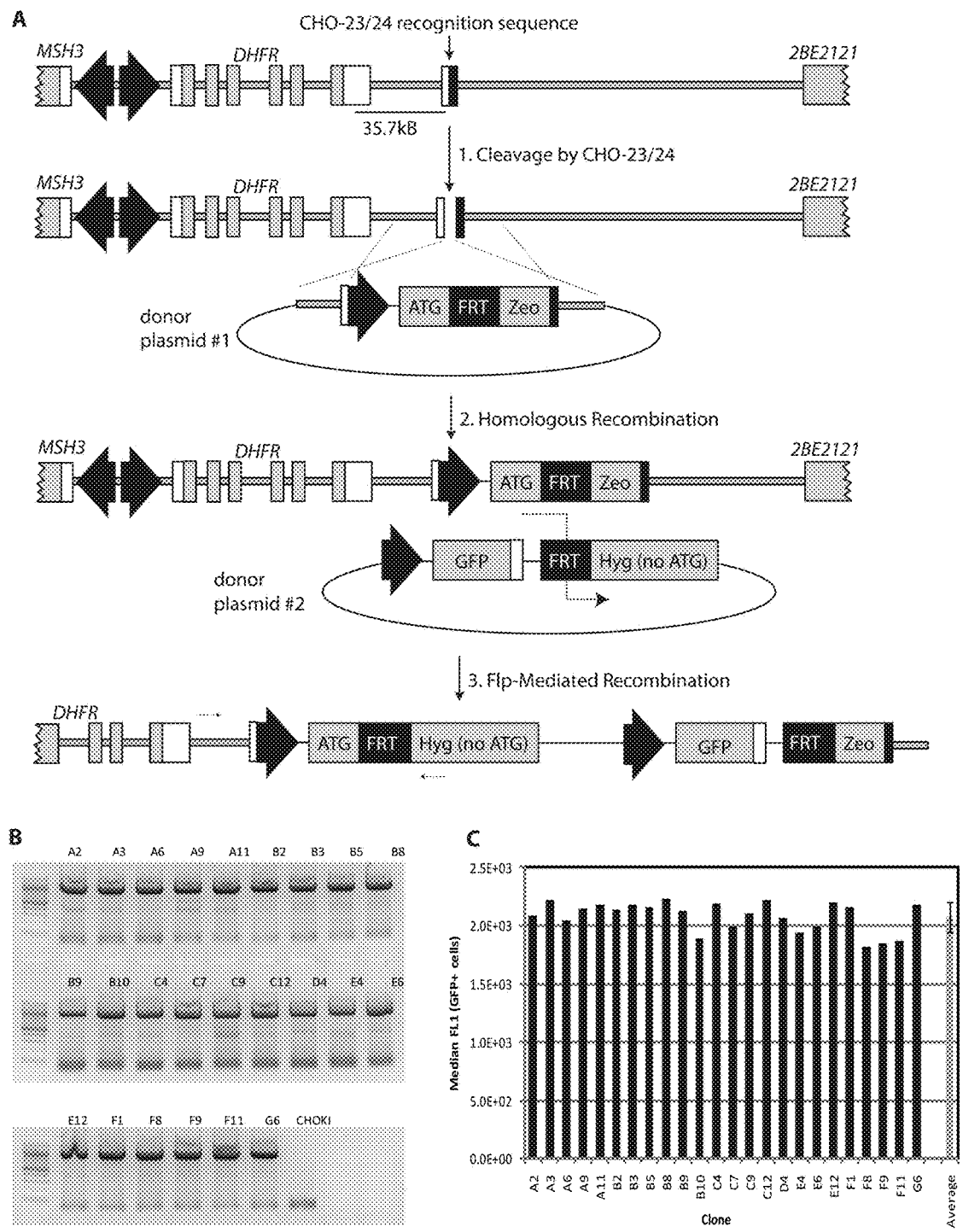
FIGS. 9A through 9C. (A) Strategy for inserting an engineered target sequence into the CHO DHFR locus using the CHO-23/24 meganuclease, followed by Flp recombinase-mediated insertion of a sequence of interest. (B) PCR products from hygromycin-resistant clones produced in (A). (C) GFP expression by the 24 clones produced in (B).
Figure 10:
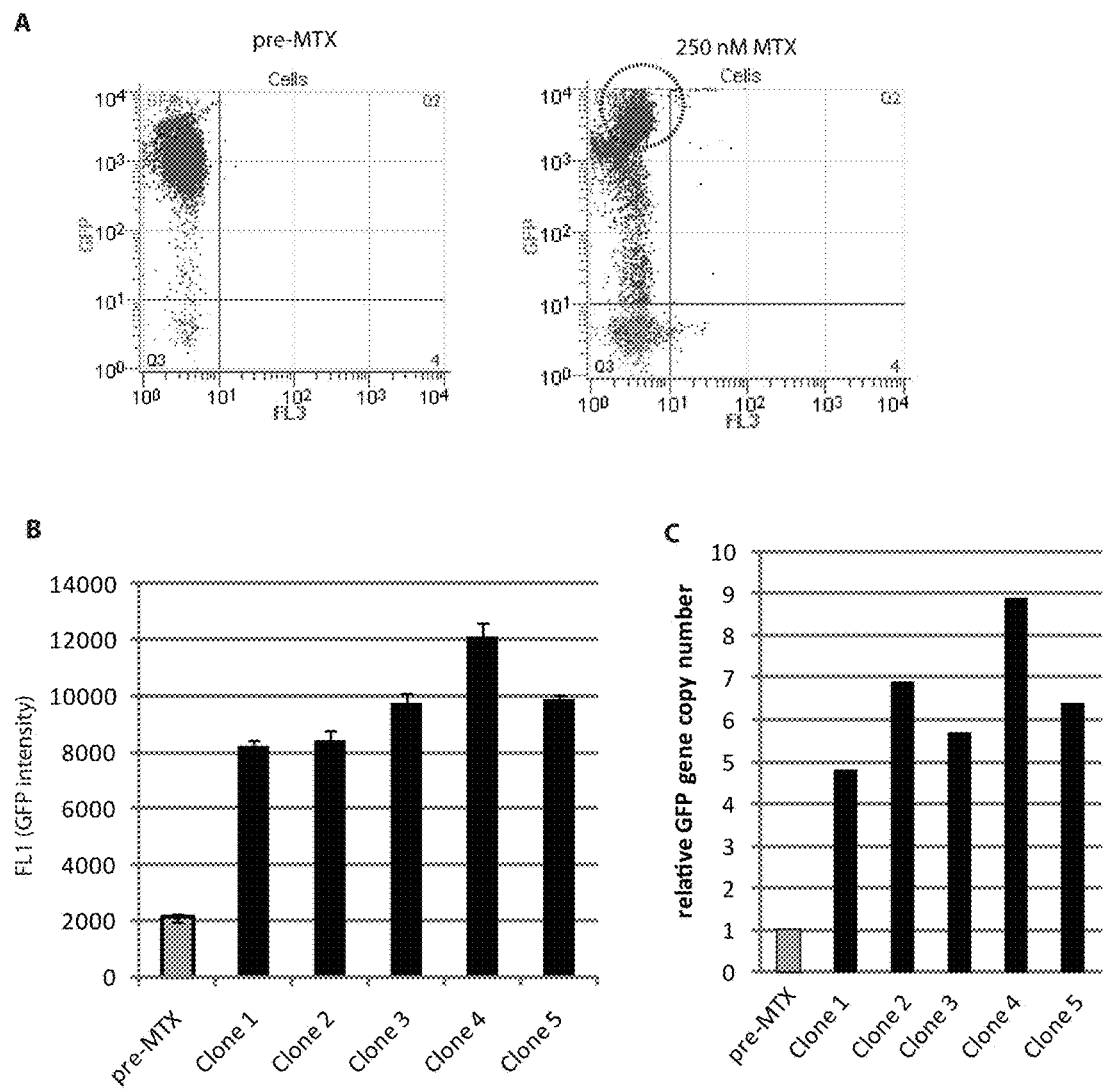
FIGS. 10A through 10C. Results of experiments with a GFP-expressing CHO line produced by integrating a GFP gene expression cassette into the DHFR locus using a target sequence strategy as shown in FIG. 9.

FIG. 10. A GFP-expressing CHO line was produced by integrating a GFP gene expression cassette into the DHFR locus using an engineered target sequence strategy as shown in FIG. 9. This cell line was then grown in MTX as described in Example 2 to amplify the integrated GFP gene. (A) Flow cytometry plots showing GFP intensity on the Y-axis. In the pre-MTX cell line, GFP intensity averages approximately $2 \times 10^3$ whereas in the cell line grown in 250 nM MTX, a distinct sub-population is visible (circled) in which GFP intensity approaches $10^4$. (B) MTX treated cell lines were sorted by FACS to identify individual cells expressing higher amounts of GFP. Five such high-expression cells were expanded and GFP intensity was determined by flow cytometry. All five clones were found to have significantly increased GFP expression relative to the pre-MTX cell line. (C) Genomic DNA was isolated from the five clonal cell lines produced in (B) and subjected to quantitative PCR using a primer pair specific for the GFP gene. It was found that the five high-expression clones had significantly more copies of the GFP gene than the pre-MTX cell line. These results demonstrate that the copy number and expression level a transgene integrated downstream of CHO DHFR can amplify in response to MTX treatment.

Figures 11A, 11B, 11C:
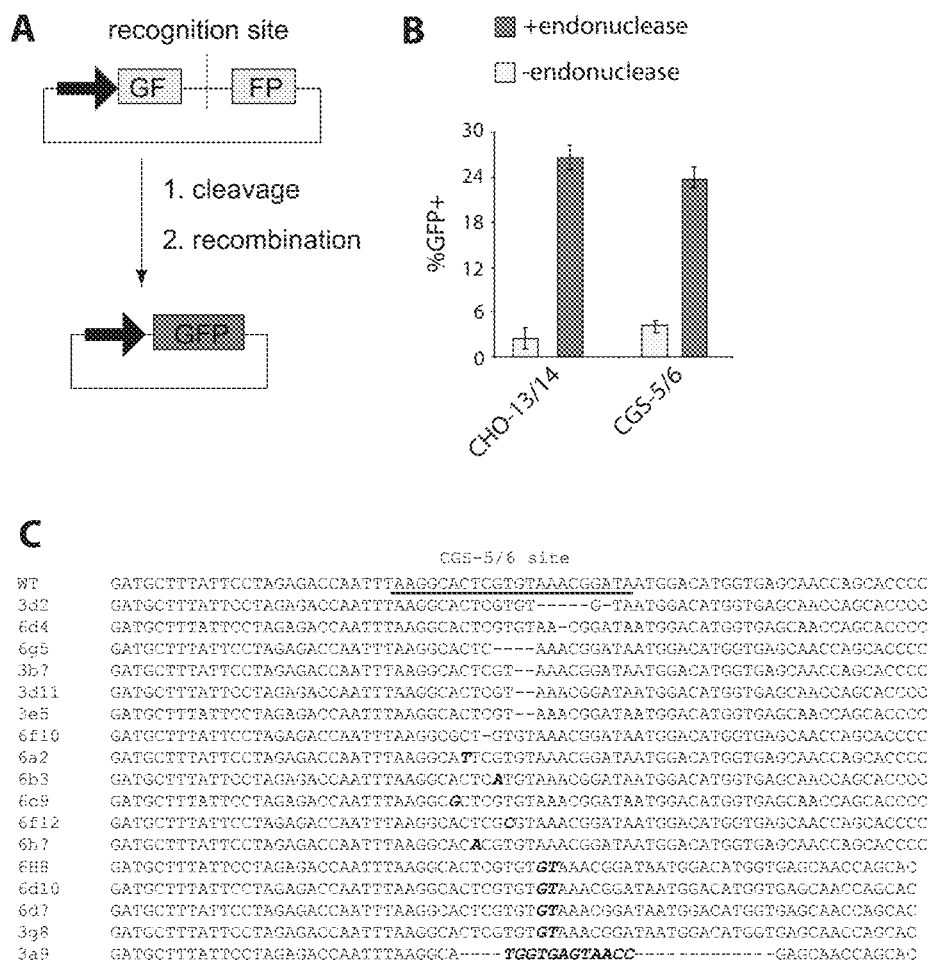
FIGS. 11A through 11C. (A) A direct-repeat recombination assay, as in FIG. 5A. (B) The assay in (A) applied to the CHO-13/14 and CGS-5/6 meganucleases. (C) Alignment of sequences obtained from CHO cells transfected with mRNA encoding the CGS-5/6 meganuclease (SEQ ID NOS 52-56, 56, 56-63, 63, 63, and 63-64, respectively, in order of appearance).

FIG. 11. (A) A direct-repeat recombination assay, as in FIG. 5A. (B) The assay in (A) applied to the CHO-13/14 and CGS-5/6 meganucleases. Light bars indicate the percentage of GFP+ cells when cells are transfected with the reporter plasmid alone (−endonuclease). Dark bars indicate the percentage of GFP+ cells when cells are co-transfected with a reporter plasmid and the corresponding meganuclease gene (+endonuclease). The assay was performed in triplicate and standard deviation is shown. (C) Alignment of sequences obtained from CHO cells transfected with mRNA encoding the CGS-5/6 meganuclease. The top sequence is from a wild-type (WT) CHO cell with the recognition sequence for CGS-5/6 underlined. Dashes indicate deleted bases. Bases that are italicized and in bold are point mutations or insertions relative to the wild-type sequence. Note that the mutations observed in at least clones 6d4, 6g5, 3b7, 3d11, 3e5, 6f10, 6hH8, 6d10, 6d7, 3g8, and 3a9 are expected to knockout GS gene function.

2.1.1 Gene Targeting to the CHO DHFR Locus

The CHO DHFR locus is diagrammed in FIG. 2A. The locus comprises the DHFR gene coding sequence in 6 exons spanning ~24,500 base pairs. The Msh3 gene is located immediately upstream of DHFR and is transcribed divergently from the same promoter as DHFR. A hypothetical gene, 2BE2121, can be found ~65,000 base pairs downstream of the DHFR coding sequence. Thus, there is a ~65,000 base pair region downstream of the DHFR gene that does not harbor any known genes and is a suitable location for targeting the insertion of sequences of interest. Target sites for insertion of a sequence of interest generally should not be selected which are <1,000 base pairs, and preferably not <5,000 base pairs from either the DHFR or 2BE2121 genes. This limits the window of preferred target sites to the region 1,000-60,000 base pairs, or 5,000-60,000 base pairs downstream of the DHFR coding sequence. The sequence of this region is provided as SEQ ID NO: 2.

The human and mouse DHFR loci have an organization similar to CHO locus. In both cases, the Msh3 gene is immediately upstream of DHFR but there is a large area devoid of coding sequences downstream of DHFR. In humans, the ANKRD34B gene is ~55,000 base pairs downstream of DHFR while the ANKRD34B gene is ~37,000 base pairs downstream of DHFR in mouse. Therefore, the genomic region downstream of DHFR is an appropriate location to insert genes of interest in CHO, human, and mouse cells and cell lines. Further, gene expression cassettes inserted into this region will be expressed at a high level, resistant to gene silencing, and capable of being amplified by treatment with MTX. Methods for amplifying the CHO cell DHFR locus are known in the art (see, e.g., Kellems, ed., *Gene amplification in mammalian cells: a comprehensive guide*. Marcel Dekker, New York, 1993) and typically involve gradually increasing the concentration of MTX in the growth media from 0 to as high as 0.8 mM over a period of several weeks.

2.1.2 Gene Targeting to the GS Locus

The CHO, human, and mouse glutamine synthetase (also known as "glutamate-ammonia ligase" or "GluL") loci share a common organization (FIG. 2B). The TEDDM1 gene is immediately upstream of GS in all species (~5,000 bp upstream in the case of human, ~7,000 bp upstream in the case of mouse and CHO). The closest downstream gene, however, is ~46,000 away in the case of human and ~117,000 bp away in the case of mouse and CHO. Therefore, we predict that the chromosomal region 1,000-41,000 bp, or 5,000-41,000 bp downstream of GS in human cells and 1,000-100,000 bp, or 5,000-100,000 bp downstream of GS in mouse and CHO cells are appropriate locations to target the insertion of sequences of interest. Because DNA sites distal to the GS coding sequence are more likely to be susceptible to gene silencing, the chromosomal region 5,000-60,000 bp downstream of GS is a preferred location to target the insertion of a sequence of interest even in mouse or CHO cells. The sequence of this region from the CHO genome is provided as SEQ ID NO: 3. Gene expression cassettes inserted into this region will be expressed at a high level, resistant to gene silencing, and capable of being amplified by treatment with MSX. Less-preferred regions include the chromosomal region between the TEDDM1 and GS genes or the region <10,000 bp downstream of TEDDM1 (see FIG. 2B). Methods for amplifying the GS locus are known in the art (Bebbington et al. (1992), *Biotechnology* (N Y). 10(2):169-75).

2.2 Engineered Endonucleases for Gene Targeting

A sequence of interest may be inserted into an amplifiable locus using an engineered site-specific endonuclease. Methods for generating site-specific endonucleases which can target DNA breaks to pre-determined loci in a genome are known in the art. These include zinc-finger nucleases (Le Provost et al. (2010), *Trends Biotechnol*. 28(3):134-41), TAL-effector nucleases (Li et al. (2011), *Nucleic Acids Res*. 39(1):359-72), and engineered meganucleases (WO 2007/047859; WO 2007/049156; WO 2009/059195). In one embodiment, the invention provides engineered meganucleases derived from I-CreI that can be used to target the insertion of a gene of interest to an amplifiable locus. Methods to produce such engineered meganucleases are known in the art (see, e.g., WO 2007/047859; WO 2007/049156; WO 2009/059195). In preferred embodiments, a "single-chain" meganuclease is used to target gene insertion to an amplifiable region of the genome. Methods for producing such "single-chain" meganucleases are known in the art (see, e.g., WO 2009/059195 and WO 2009/095742). In some embodiments, the engineered nuclease is fused to a nuclear localization signal (NLS) to facilitate nuclear uptake. Examples of nuclear localization signals include the SV40 NLS (amino acid sequence MAPKKKRKV (SEQ ID NO: 36)) which can be fused to the C- or, preferably, the N-terminus of the protein. In addition, an engineered nuclease may be tagged with a peptide epitope (e.g., an HA, FLAG, or Myc epitope) to monitor expression levels or localization or to facilitate purification.

2.3 Engineered Cell Lines with Sequences of Interest Targeted to Amplifiable Loci In some embodiments, the invention provides methods for using engineered nucleases to target the insertion of transgenes into amplifiable loci in cultured mammalian cells. This method has two primary components: (1) an engineered nuclease; and (2) a donor DNA molecule comprising a sequence of interest. The method comprises contacting the DNA of the cell with the engineered nuclease to create a double strand DNA break in an endogenous recognition sequence in an amplifiable locus followed by the insertion of the donor DNA molecule at the site of the DNA break. Such insertion of the donor DNA is facilitated by the cellular DNA-repair machinery and can occur by either the non-homologous end-joining pathway or by homologous recombination (FIG. 1).

The engineered nuclease can be delivered to the cell in the form protein or, preferably, as a nucleic acid encoding the engineered nuclease. Such nucleic acid can be DNA (e.g., circular or linearized plasmid DNA or PCR products) or RNA. For embodiments in which the engineered nuclease coding sequence is delivered in DNA form, it should be operably linked to a promoter to facilitate transcription of the engineered nuclease gene. Mammalian promoters suitable for the invention include constitutive promoters such as the cytomegalovirus early (CMV) promoter (Thomsen et al. (1984), *Proc Natl Acad Sci USA*. 81(3):659-63) or the SV40 early promoter (Benoist and Chambon (1981), *Nature*. 290 (5804):304-10) as well as inducible promoters such as the tetracycline-inducible promoter (Dingermann et al. (1992), *Mol Cell Biol*. 12(9):4038-45).

In some embodiments, mRNA encoding the engineered nuclease is delivered to the cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methyl-guanosine. In some embodiments, the mRNA may be poly-adenylated.

Purified engineered nuclease proteins can be delivered into cells to cleave genomic DNA, which allows for homologous recombination or non-homologous end-joining at the cleavage site with a sequence of interest, by a variety of different mechanisms known in the art. For example, the recombinant nuclease protein can be introduced into a cell by techniques including, but not limited to, microinjection or liposome transfections (see, e.g., Lipofectamine™, Invitrogen Corp., Carlsbad, Calif.). The liposome formulation can be used to facilitate lipid bilayer fusion with a target cell, thereby allowing the contents of the liposome or proteins associated with its surface to be brought into the cell. Alternatively, the enzyme can be fused to an appropriate uptake peptide such as that from the HIV TAT protein to direct cellular uptake (see, e.g., Hudecz et al. (2005), *Med. Res. Rev*. 25: 679-736).

Alternatively, gene sequences encoding the engineered nuclease protein are inserted into a vector and transfected into a eukaryotic cell using techniques known in the art (see, e.g., Ausubel et al., *Current Protocols in Molecular Biology*, Wiley 1999). The sequence of interest can be introduced in the same vector, a different vector, or by other means known in the art. Non-limiting examples of vectors for DNA transfection include virus vectors, plasmids, cosmids, and YAC vectors. Transfection of DNA sequences can be accomplished by a variety of methods known to those of skill in the art. For instance, liposomes and immunoliposomes are used to deliver DNA sequences to cells (see, e.g., Lasic et al. (1995), *Science* 267: 1275-76). In addition, viruses can be utilized to introduce vectors into cells (see, e.g., U.S. Pat. No. 7,037,492). Alternatively, transfection strategies can be utilized such that the vectors are introduced as naked DNA (see, e.g., Rui et al. (2002), *Life Sci.* 71(15): 1771-8).

General methods for delivering nucleic acids into cells include: (1) chemical methods (Graham et al. (1973), *Virology* 54(2):536-539; Zatloukal et al. (1992), *Ann. N.Y. Acad. Sci.*, 660:136-153; (2) physical methods such as microinjection (Capecchi (1980), *Cell* 22(2):479-488, electroporation (Wong et al. (1982), *Biochim. Biophys. Res. Commun.* 107(2):584-587; Fromm et al. (1985), *Proc. Nat'l Acad. Sci. USA* 82(17):5824-5828; U.S. Pat. No. 5,384,253) and ballistic injection (Johnston et al. (1994), *Methods Cell. Biol.* 43(A): 353-365; Fynan et al. (1993), *Proc. Nat'l Acad. Sci. USA* 90(24): 11478-11482); (3) viral vectors (Clapp (1993), *Clin. Perinatol.* 20(1): 155-168; Lu et al. (1993), *J. Exp. Med.* 178(6):2089-2096; Eglitis et al. (1988), *Avd. Exp. Med. Biol.* 241:19-27; Eglitis et al. (1988), *Biotechniques* 6(7): 608-614); and (4) receptor-mediated mechanisms (Curiel et al. (1991), *Proc. Nat'l Acad. Sci. USA* 88(19):8850-8854; Curiel et al. (1992), *Hum. Gen. Ther.* 3(2):147-154; Wagner et al. (1992), *Proc. Nat'l Acad. Sci. USA* 89 (13):6099-6103). In some preferred embodiments, 7-methyl-guanosine capped mRNA encoding the engineered nuclease is delivered to cells using electroporation.

The donor DNA molecule comprises a gene of interest operably linked to a promoter. In many cases, a donor molecule may comprise multiple genes operably linked to the same or different promoters. For example, donor molecules comprising monoclonal antibody expression cassettes may comprise a gene encoding the antibody heavy chain and a second gene encoding the antibody light chain. Both genes may be under the control of different promoters or they may be under the control of the same promoter by using, for example, an internal-ribosome entry site (IRES). Donor molecules may also comprise a selectable marker gene operably linked to a promoter to facilitate the identification of transgenic cells. Such selectable markers are known in the art and include neomycin phosphotransferase (NEO), hypoxanthine phosphoribosyltransferase (HPRT), glutamine synthetase (GS), dihydrofolate reductase (DHFR), and hygromycin phosphotransferase (HYG) genes.

In some embodiments, donor DNA molecules will additionally comprise flanking sequences homologous to the target sequences in the DNA of the cell. Such homologous flanking sequences comprise >3 or, preferably, >50 or, more preferably, >200 or, most preferably, >400 base pairs of DNA that are identical or nearly identical in sequence to the chromosomal locus recognized by the engineered nuclease (FIG. 1). Such homologous DNA sequences facilitate the integration of the donor DNA sequence into the amplifiable locus by homologous recombination.

The "donor" DNA molecule can be circular (e.g., plasmid DNA) or linear (e.g., linearized plasmid or PCR products). Methods for delivering DNA molecules are known in the art, as discussed above.

In some embodiments, the engineered nuclease gene and donor DNA are carried on separate nucleic acid molecules which are co-transfected into cells or cell lines. For example, the engineered nuclease gene operably linked to a promoter can be transfected in plasmid form simultaneously with a separate donor DNA molecule in plasmid or PCR product form. In an alternative embodiment, the engineered nuclease can be delivered in mRNA form with a separate donor DNA molecule in plasmid or PCR product form. In a third embodiment, the engineered nuclease gene and donor DNA are carried on the same DNA molecule, such as a plasmid. In a fourth embodiment, cells are co-transfected with purified engineered nuclease protein and a donor DNA molecule in plasmid or PCR product form.

Following transfection with the engineered nuclease and donor DNA, cells are typically allowed to recover from transfection (24-72 hours) before being cloned using methods known in the art. Common methods for cloning a genetically engineered cell line include "limiting dilution" in which transfected cells are transferred to tissue culture plates (e.g., 48 well, 96 well plates) at a concentration of <1 cell per well and expanded into clonal populations. Other cloning strategies include robotic clone identification/isolation systems such as ClonePix™ (Genetix, Molecular Devices, Inc., Sunnyvale, Calif.). Clonal cell lines can then be screened to identify cell lines in which the sequence of interest is integrated into the intended target site. Cell lines can easily be screened using molecular analyses known in the art such as PCR or Southern Blot. For example, genomic DNA can be isolated from a clonal cell line and subjected to PCR amplification using a first (sense-strand) primer that anneals to a DNA sequence in the sequence of interest and a second (anti-sense strand) primer that anneals to a sequence in the amplifiable locus. If the donor DNA molecule comprises a DNA sequence homologous to the target site, it is important that the second primer is designed to anneal to a sequence in the amplifiable locus that is beyond the limits of homology carried on the donor molecule to avoid false positive results. Alternatively, cell lines can be screened for expression of the sequence of interest. For example, if the sequence of interest encodes a secreted protein such as an antibody, the growth media can be sampled from isolated clonal cell lines and assayed for the presence of antibody protein using methods known in the art such as Western Blot or Enzyme-Linked Immunosorbant Assay (ELISA). This type of functional screen can be used to identify clonal cell lines which carry at least one copy of the sequence of interest integrated into the genome. Additional molecular analyses such as PCR or Southern blot can then be used to determine which of these transgenic cell lines carry the sequence of interest targeted to the amplifiable locus of interest, as described above.

The method of the invention can be used on any culturable and transfectable cell type such as immortalized cell lines and stem cells. In preferred embodiments, the method of the invention is used to genetically modify immortalized cell lines that are commonly used for biomanufacturing. This includes:

1. Hamster cell lines such as baby hamster kidney (BHK) cells and all variants of Chinese Hamster Ovary (CHO) cells, e.g., CHO-K1, CHO-S (Invitrogen Corp., Carlsbad, Calif.), DG44, or Potelligent™ (Lonza Group Ltd., Basel, Switzerland). Because the genome sequences of different hamster cell lines are very nearly identical, an engineered meganuclease which can be used to practice the invention in one hamster cell type (e.g., BHK cells) can generally be used to practice the invention in another hamster cell type (e.g., CHO-K1).

2. Mouse cell lines such as mouse hybridoma or mouse myeloma (e.g., NS0) cells. Because the genome sequences of different mouse cell lines are very nearly identical, an engineered meganuclease which can be used to practice the invention in one mouse cell type (e.g., mouse hybridoma cells) can generally be used to practice the invention in another mouse cell type (e.g., NS0).

3. Human cell lines such as human embryonic kidney cells (e.g., HEK-293 or 293S) and human retinal cells (e.g., PER.C6). Because the genome sequences of different human cell lines are very nearly identical, an engineered meganuclease which can be used to practice the invention in one human cell type (e.g., HEK-293 cells) can generally be used to practice the invention in another human cell type (e.g., PER.C6).

2.6 Pre-Engineered Cell Lines with Engineered Target Sequences in Amplifiable Loci.

In one embodiment, the invention provides cell lines which are pre-engineered to comprise a targetable "engineered target sequence" for gene insertion in an amplifiable locus in a mammalian cell line (FIG. 3). An engineered target sequence comprises a recognition sequence for an enzyme which is useful for inserting transgenic nucleic acids into chromosomal DNA sequences. Such engineered target sequences can include recognition sequences for engineered meganucleases derived from I-CreI (e.g., SEQ ID NO 37-87 from WO 2009/076292), recognition sequences for zinc-finger nucleases, recognition sequences for TAL effector nucleases (TALENs), the LoxP site (SEQ ID NO 4) which is recognized by Cre recombinase, the FRT site (SEQ ID NO: 5) which is recognized by FLP recombinase, the attB site (SEQ ID NO: 6) which is recognized by lambda recombinase, or any other DNA sequence known in the art that is recognized by a site specific endonuclease, recombinase, integrase, or transpose that is useful for targeting the insertion of nucleic acids into a genome. Thus, the invention allows one skilled in the art to use an engineered nuclease (e.g., a meganuclease, zinc-finger nuclease, or TAL effector nuclease) to insert an engineered target sequence into an amplifiable locus in a mammalian cell line. The resulting cell line comprising such an engineered target sequence at an amplifiable locus can then be contacted with the appropriate enzyme (e.g., a second engineered meganuclease, a second zinc-finger nuclease, a second TAL effector nuclease, a recombinase, an integrase, or a transposase) to target the insertion of a gene of interest into the amplifiable locus at the engineered target sequence. This two-step approach can be advantageous because the efficiency of gene insertion that can be achieved using an optimal meganuclease, zinc-finger nuclease, recombinase, integrase, or transposase might be higher than what can be achieved using the initial endonuclease (e.g., meganuclease or zinc-finger nuclease) that cleaves the endogenous target site to promote insertion of the engineered target sequence.

In an alternative embodiment, a cell line is produced by inserting an engineered target sequence into an amplifiable locus with the concomitant removal of all or a portion of the adjacent endogenous marker gene (FIG. 4). For example, an engineered meganuclease, zinc-finger nuclease, or TAL-effector nuclease can be used to remove the first two exons of both alleles of the CHO DHFR gene and replace them with an engineered target sequence for a different engineered meganuclease, ZFN, TALEN, recombinase, integrase, or transposase. The resulting cell line will be DHFR deficient and unable to grow in the absence of hypoxanthine/thymidine. Alternatively, for example, an engineered meganuclease, ZFN or TALEN can be used to remove the first exon of both alleles of the CHO GS gene and replace it with an engineered target sequence for a different engineered meganuclease, ZFN, TALEN, recombinase, integrase, or transposase (FIG. 4). The resulting cell line will be GS deficient and unable to grow in the absence of L-glutamine. Such a cell line is useful because a gene of interest can be inserted into the engineered target sequence in the pre-engineered cell line while simultaneously reconstituting the selectable gene (e.g., DHFR or GS). Thus, it is possible to select for transfectants harboring the gene of interest at the amplifiable locus using media conditions that select for DHFR+ or GS+ cells.

In an alternative embodiment, a cell line is produced in which an engineered target sequence is inserted into an amplifiable locus with disruption of the selectable gene (FIGS. 5, 6). This can be accomplished, for example, using a meganuclease which recognizes a DNA site in the coding sequence of the selectable gene. Such a meganuclease can be used to target the insertion of an engineered target sequence into the selectable gene coding sequence resulting in disruption of gene function by, for example, introducing a frameshift (FIG. 5). Alternatively, for example, an engineered target sequence can be inserted into an intron in the selectable gene sequence with an additional sequence that promotes improper processing of the selectable gene transcript (FIG. 6). Such sequences that promote improper processing include, for example, artificial splice acceptors or polyadenylation signals. Splice acceptor sequences are known in the art (Clancy (2008), "RNA Splicing: Introns, Exons and Spliceosome," *Nature Education* 1:1) and typically comprise a 20-50 base pair pyrimidine-rich sequence followed by a sequence (C/T)AG(A/G). SEQ ID NO: 33 is an example of a splice acceptor sequence. Likewise, polyadenylation signals are known in the art and include, for example, the SV40 polyadenylation signal (SEQ ID NO: 34) and the BGH polyadenylation signal (SEQ ID NO: 35). In some embodiments, the resulting cell line harboring the new engineered target sequence in all alleles of the selectable gene will be deficient in the function of the gene due to mis-transcription or mis-translation and will be able to grow only under permissive conditions. For example, an engineered target sequence can be inserted into the GS gene sequence using a meganuclease resulting in a cell line that is GS−/− that can grow only in the presence of L-glutamine in the growth media. In a subsequent step, a gene of interest can be inserted into the engineered target sequence while simultaneously reconstituting the selectable gene (e.g., DHFR or GS). Thus, it is possible to select for transfectants harboring the gene of interest at the amplifiable locus using media conditions that select for DHFR+ or GS+ cells.

2.5 Transgenic Cell Lines for Biomanufacturing.

In some embodiments, the invention provides transgenic cell lines suitable for the production of protein pharmaceuticals. Such transgenic cell lines comprise a population of cells in which a gene of interest, operably linked to a promoter, is inserted into the genome of the cell at an amplifiable locus wherein the gene of interest encodes a protein therapeutic. Examples of protein therapeutics include: monoclonal antibodies, antibody fragments, erythropoietin, tissue-type plasminogen activator, Factor VIII, Factor IX, insulin, colony stimulating factors, interferons (e.g., interferon-α, interferon-β, and interferon-γ), interleukins (e.g., interleukin-2), vaccines, tumor necrosis factor, and glucocerebrosidase. Protein therapeutics are also referred to as "biologics" or "biopharmaceuticals."

To be used for biomanufacturing, a transgenic cell line of the invention should undergo: (1) adaptation to serum-free growth in suspension; and (2) amplification of the gene of interest. In some embodiments, the invention is practiced on adherent cell lines which can be adapted to growth in suspension to facilitate their maintenance in shaker-flasks or stirred-tank bioreactors as is typical of industrial biomanufacturing. Methods for adapting adherent cells to growth in suspension are known in the art (*Cell Culture and Upstream Processing*, Butler, ed. (Taylor and Francis Group, New York, 2007)). For regulatory reasons, it is generally necessary to further adapt biomanufacturing cell lines to chemically-defined media lacking animal-derived components (i.e., "serum-free" media). Methods for preparing such media and adapting cell lines to it are known in the art (*Cell Culture and Upstream Processing*, Butler, ed. (Taylor and Francis Group, New York, 2007)). Such media can also be purchased commercially (e.g., CD-3 media for maintenance of CHO cells, available from Sigma-Aldrich, St. Louis, Mo.) and cells can be adapted to it by following the manufacturers' instructions. In some embodiments, the cell line is adapted to growth in suspension and/or serum-free media prior to being transfected with the engineered nuclease.

Lastly, methods for gene amplification are known in the art (*Cell Culture and Upstream Processing*, Butler, ed. (Taylor and Francis Group, New York, 2007)). In general, the process involves adding an inhibitor of a selectable gene product to the growth media to select for cells that express abnormally high amounts of the gene product due to gene-duplication events. In general, the concentration of inhibitor added to the growth media is increased slowly over a period of weeks until the desired level of gene amplification is achieved Inhibitor is then generally removed from the media prior to initiating a bioproduction run to avoid the possibility of the inhibitor contaminating the protein therapeutic formulation. For example, the CHO DHFR locus can be amplified by slowly increasing the concentration of MTX in the growth media from 0 mM to as high as 0.8 mM over a period of several weeks. The GS locus can, likewise, be amplified by slowly increasing the concentration of MSX in the media from 0 μM to as high as 100 μM over a period of several weeks. Methods for evaluating gene amplification are known in the art and include Southern Blot and quantitative real-time PCR (rtPCR). In addition, or as an alternative, expression levels of the sequence of interest, which are generally correlated to gene copy number, can be evaluated by determining the concentration of protein therapeutic in the growth media using conventional methods such as Western Blot or ELISA.

Following cell line production, adaptation, and amplification, protein therapeutics can be produced and purified using methods that are standard in the biopharmaceutical industry.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1 refers to engineered meganucleases that can be used to target the insertion of a gene of interest downstream of the DHFR gene in CHO cells. Example 2 refers to engineered meganucleases that can be used to target the insertion of an engineered target sequence into the CHO DHFR gene with concomitant removal of DHFR exons 1 and 2. Example 2 also refers to engineered meganucleases that can be used to target the insertion of an engineered target sequence into the CHO GS gene. Example 3 refers to meganucleases that can be used to target the insertion of a gene of interest downstream of the GS gene in CHO cells.

Example 1

Targeted Gene Insertion into the CHO DHFR Locus Using Engineered Meganucleases

The CHO genomic DNA sequence 10,000-55,000 base pairs downstream of the DHFR gene was searched to identify DNA sites amenable to targeting with engineered meganucleases. Two sites (SEQ ID NO: 7 and SEQ ID NO: 8) were selected which are, respectively, 35,699 and 15,898 base pairs downstream of the DHFR coding sequence (Table 2).

TABLE 2

Example Recognition Sites For Engineered Meganucleases in the CHO DHFR Locus.

| SEQ ID NO: | Target Site Sequences | Location Relative to CHO DHFR Coding Sequence |
|---|---|---|
| 7 | 5'-TAAGGCCTCATATGAAAATATA-3' | 35,699 bp downstream |
| 8 | 5'-ATAGATGTCTTGCATACTCTAG-3' | 15,898 bp downstrea |

1. Meganucleases that Recognize SEQ ID NO: 7 and SEQ ID NO: 8

An engineered meganuclease (SEQ ID NO: 9) was produced which recognizes and cleaves SEQ ID NO: 7. This meganuclease is called "CHO-23/24". A second engineered meganuclease (SEQ ID NO: 10) was produced which recognizes and cleaves SEQ ID NO: 8. This meganuclease is called "CHO-51/52." Each meganuclease comprises an N-terminal nuclease-localization signal derived from SV40, a first meganuclease subunit, a linker sequence, and a second meganuclease subunit.

2. Site-Specific Cleavage of Plasmid DNA by Meganucleases CHO-23/24 and CHO-51/52

CHO-23/24 and CHO-51/52 were evaluated using a direct-repeat recombination assay as described previously (Gao et al. (2010), Plant J. 61(1):176-87, FIG. 7A). A defective GFP reporter cassette was generated by first cloning a 5' 480 bp fragment of the GFP gene into NheI/HindIII-digested pcDNA™5/FRT mammalian expression vector (Invitrogen Corp., Carlsbad, Calif.) resulting in the plasmid pGF. Next, a 3' 480 bp fragment of the GFP gene (including a 240 bp sequence duplicated in the 5' 480 bp fragment) was cloned into BamHI/XhoI-digested pGF. The resulting plasmid, pGFFP, consists of the 5' two-thirds of the GFP gene followed by the 3' two-thirds of the GFP gene, interrupted by 24 bp of the pcDNA5/FRT polylinker. To insert the meganuclease recognition sites, complementary oligonucleotides comprising the sense and anti-sense sequence of each recognition site were annealed and ligated into Hind III/BamHI-digested pGFFP.

The coding sequences of the engineered meganucleases were inserted into the mammalian expression vector pCP under the control of a constitutive (CMV) promoter. Chinese hamster ovary (CHO) cells at approximately 90% confluence were transfected in 96-well plates with 150 ng pGFFP reporter plasmid and 50 ng of meganuclease expression vector or, to determine background, 50 ng of empty pCP, using LIPOFECTAMINE® 2000 transfection reagent according to the manufacturer's instructions (Invitrogen Corp., Carlsbad, Calif.). To determine50 ng of empty pCP, using LIPOFECTAMINE® 2000 transfection reagent according to the manufacturer's instructions (Invitrogen Corp., Carlsbad, Calif.). To determine transfection efficiency, CHO cells were transfected with 200 ng pCP GFP. Cells were washed in PBS 24 h post-transfection, trypsinized and resuspended in PBS supplemented with 3% fetal bovine serum. Cells were assayed for GFP activity using a CELL LAB QUANTA™ SC MPL flow cytometer and the accompanying CELL LAB QUANTA™ analysis software (Beckman Coulter, Brea, Cailf.).

Results are shown in FIG. 7B. It was found that both of the engineered meganucleases were able to cleave their intended recognition sites significantly above background within the context of a plasmid-based reporter assay.

3. Site-Specific Cleavage of CHO DHFR Locus by Meganucleases CHO-23/24 and CHO-51/52

To determine whether or not CHO-23/24 and CHO-51/52 are capable of cleaving their intended target sites in the CHO DHFR locus, we screened genomic DNA from CHO cells expressing either CHO-23/24 or CHO-51/52 to identify evidence of chromosome cleavage at the intended target site. This assay relies on the fact that chromosomal DNA breaks are frequently repaired by NHEJ in a manner that introduces mutations at the site of the DNA break. These mutations, typically small deletions or insertions (collectively known as "indels") leave a telltale scar that can be detected by DNA sequencing (Gao et al. (2010), *Plant J.* 61(1):176-87).

CHO cells were transfected with mRNA encoding CHO-23/24 or CHO-51/52. mRNA was prepared by first producing a PCR template for an in vitro transcription reaction (SEQ ID NO: 20 and SEQ ID NO: 21). Each PCR product included a T7 promoter and 609 bp of vector sequence downstream of the meganuclease gene. The PCR product was gel purified to ensure a single template. Capped (m7G) RNA was generated using the T7 RIBOMAX™ in vitro transcription kit (Promega Corp., Fitchburg, Wis.) according to the manufacturer's instructions and Ribo m7G cap analog (Promega Corp., Fitchburg, Wis.) was included in the reaction and 0.5 μg of the purified meganuclease PCR product served as the DNA template. Capped RNA was purified using the SV Total RNA Isolation System (Promega Corp., Fitchburg, Wis.) according to the manufacturer's instructions.

$1.5 \times 10^6$ CHO-K1 cells were nucleofected with $3 \times 10^{12}$ copies of CHO-23/24 or CHO-51/52 mRNA ($2 \times 10^6$ copies/cell) using an Amaxa Nucleofector II device (Lonza Group Ltd., Basel, Switzerland) and the U-23 program according to the manufacturer's instructions. 48 hours post-transfection, genomic DNA was isolated from the cells using a FlexiGene kit (Qiagen, Hilden, Germany) according to the manufacturer's instructions. The genomic DNA was then subjected to PCR to amplify the corresponding target site. In the case of cells transfected with mRNA encoding CHO-23/24, the forward and reverse PCR primers were SEQ ID NO: 16 and SEQ ID NO: 17. In the case of cells transfected with mRNA encoding CHO-51/52, the forward and reverse PCR primers were SEQ ID NO: 18 and SEQ ID NO: 19. PCR products were gel purified and cloned into pUC-19. 40 plasmids harboring PCR products derived from cells transfected with CHO-23/24 mRNA were sequenced, 13 of which were found to have mutations in the CHO-23/24 target site (FIG. 7C). 44 plasmids harboring PCR products derived from cells transfected with CHO-51/52 mRNA were sequenced, 10 of which were found to have mutations in the CHO-51/52 target site (FIG. 7D). These results indicate that CHO-23/24 and CHO-51/52 are able to cut their intended target sites downstream of the CHO DHFR gene.

4. Site-Specific Integration into the CHO DHFR Locus Using an Engineered Meganuclease To evaluate the efficiency of DNA insertion into the CHO DHFR locus using an engineered meganuclease, we prepared a donor plasmid (SEQ ID NO: 11) comprising an EcoRI restriction enzyme site flanked by DNA sequence homologous to the CHO-51/52 recognition site (FIG. 8A). Specifically, the donor plasmid of SEQ ID NO: 11 comprises a pUC-19 vector harboring a homologous recombination cassette inserted between the KpnI and HindIII restriction sites. The homologous recombination cassette comprises, in 5'- to 3'-order: (i) 543 base pairs of DNA identical to the sequence immediately upstream of the CHO-51/52 cut site, including the upstream half-site of the CHO-51/52 recognition sequence and the four base pair "center sequence" separating the two half-sites comprising the CHO-51/52 recognition sequence; (ii) an EcoRI restriction enzyme site (5'-GAATTC-3'); and iii) 461 base pairs of DNA identical to the sequence immediately downstream of the CHO-51/52 cut site, including the downstream half-site of the CHO-51/52 recognition sequence and the four base pair "center sequence" separating the two half-sites comprising the CHO-51/52 recognition sequence. Note that this results in a duplication of the four base pair "center sequence" (5'-TTGC-3') to maximize the likelihood of strand invasion by the 3' overhangs generated by CHO-51/52 cleavage. We have discovered that donor plasmids comprising such a duplication of the center sequence are optimal substrates for gene targeting by homologous recombination.

mRNA encoding CHO-51/52 was prepared as described above. $1.5 \times 10^6$ CHO-K1 cells were nucleofected with $3 \times 10^{12}$ copies of CHO 51-52 mRNA ($2 \times 10^6$ copies/cell) and 1.5 μg of the donor plasmid (SEQ ID NO: 11). Nucleofection was performed using an Amaxa Nucleofector II device (Lonza Group Ltd., Basel, Switzerland) and the U-23 program according to the manufacturer's instructions. 48 hours post-transfection, genomic DNA was isolated from the cells using a FlexiGene kit (Qiagen, Hilden, Germany) according to the manufacturer's instructions. The DNA was subjected to PCR using primers flanking the CHO-51/52 recognition site (SEQ ID NO: 18 and SEQ ID NO: 19). Importantly, these primers are beyond the limits of homologous sequence carried in the donor plasmid and, therefore, will amplify only the chromosomal DNA sequence and not the donor plasmid. PCR products were cloned into a pUC-19 plasmid and 48 clones were purified and digested with EcoRI (FIG. 8B). 10 plasmids yielded a restriction pattern consistent with the insertion of an EcoRI site into the CHO-51/52 recognition sequence. These data demonstrate that it is possible to use CHO-51/52 to precisely insert DNA downstream of the CHO DHFR gene at SEQ ID NO: 8.

5. Site-Specific Integration of an Engineered Target Sequence into the CHO DHFR Locus A donor plasmid (SEQ ID NO: 25) was produced comprising an FRT sequence (SEQ ID NO: 5) adjacent to a zeocin resistance gene under the control of an SV40 early promoter (FIG. 9A). This cassette was flanked by DNA sequence homologous to the CHO DHFR locus immediately upstream or downstream of the CHO-23/24 recognition sequence. CHO cells were co-transfected with this donor plasmid and mRNA encoding CHO-23/24 as described above. 72 hours post-transfection, ZEOCIN™-resistant cells were cloned by limiting dilution and expanded for approximately 3 weeks. Clonal populations were then screened by PCR using a first primer in the SV40 promoter (SEQ ID NO: 26) and a second primer in the DHFR locus (SEQ ID NO: 16) to identify cell lines carrying the FRT/ ZEOCIN™ sequence downstream of the DHFR gene. One such cell line carrying the integrated FRT Insertion target sequence was subsequently co-transfected with a second donor plasmid (SEQ ID NO: 27) and a plasmid encoding Flp recombinase. SEQ ID NO: 27 comprises a GFP gene under the control of a CMV promoter, a FRT sequence, and a non-functional hygromycin resistance gene lacking an ATG start codon. Flp-stimulated recombination between FRT sites in the genome and the plasmid resulted in the (9A). This cassette was flanked by DNA sequence homologous to the CHO DHFR locus immediately upstream or downstream of the CHO-23/24 recognition sequence. CHO cells were co-transfected with this donor plasmid and mRNA encoding CHO-23/24 as described above. 72 hours post-transfection, ZEOCIN™-resistant cells were cloned by limiting dilution and expanded for approximately 3 weeks. Clonal populations were then screened by PCR using a first primer in the SV40 promoter (SEQ ID NO: 26) and a second primer in the DHFR locus (SEQ ID NO: 16) to identify cell lines carrying the FRT/ ZEOCIN™ sequence downstream of the DHFR gene. One such cell line carrying the integrated FRT Insertion target sequence was subsequently co-transfected with a second donor plasmid (SEQ ID NO: 27) and a plasmid encoding Flp recombinase. SEQ ID NO: 27 comprises a GFP gene under the control of a CMV promoter, a FRT sequence, and a non-functional hygromycin resistance gene lacking an ATG start codon. Flp-stimulated recombination between FRT sites in the genome and the plasmid resulted in the incorporation of the entire plasmid sequence into the CHO genome at the site of the engineered target sequence. Such recombination restored function to the hygromycin-resistance gene by orientating it downstream of an ATG start codon integrated as part of the engineered target sequence. As such, successful integrations could be selected using hygromycin.

Hygromycin-resistant cells were cloned by limiting dilution and 24 individual clonal lines were assayed by PCR using a first primer in the hygromycin-resistance gene (SEQ ID NO: 28). All 24 clones yielded the expected PCR product (FIG. 9B), indicating that the GFP gene expression cassette was successfully inserted into the DHFR engineered target sequence in all cases. The 24 cell lines were then evaluated by flow cytometry and were found to express consistent levels of GFP (FIG. 9C).

6. Transgene Amplification

A GFP-expressing CHO line produced as described above was seeded at a density of $3 \times 10^5$ cells/mL in 30 mL of media containing 50 nM MTX. Cells were cultured for 14 days before being re-seeded at the same density in media containing 100 nM MTX. Cells were cultured for another 14 days before being re-seeded in media containing 250 nM MTX. Following 14 days in culture, GFP expression in the treated cells was evaluated by flow cytometry and compared to GFP expression in the parental (pre-MTX) cell population (FIG. 10A). It was found that the MTX-treated cells had a distinct sub-population in which GFP expression was significantly increased. Individual high-expression cells from the MTX-treated population were then isolated using a cell sorter and 5 clones were expanded for 14 days in the absence of MTX. GFP expression in the 5 clonal cell populations was then evaluated by flow cytometry and compared with the parental (pre-MTX) cell population. It was found that the MTX-treated clones had approximately 4-6 times the GFP intensity as the pre-MTX cells. Quantitative PCR was then performed using a primer set specific for the GFP gene and it was found that the MTX-treated clones all had approximately 5-9 times as many copies of the GFP gene as the pre-MTX population. These data provide conclusive evidence that a transgene inserted downstream of the CHO DHFR gene can be amplified by treatment with MTX.

7. Stability of Gene Amplification

The five clonal cell lines expressing high levels of GFP that were produced in (6) above were then passaged for a period of 14 weeks in media with or without 250 nM MTX to evaluate the stability of gene amplification. GFP intensity was determined on a weekly basis and the quantitative PCR assay used to determine GFP gene copy number described above was repeated at the end of the 14 week evaluation period. As expected, the clones passaged in media with MTX maintained a high level of GFP expression with no clone deviating more than 20% from the GFP intensity determined in week 1. Quantitative PCR revealed that gene copy number likewise deviated by less than 20% for all clones. Surprisingly, gene amplification was equally stable in cell lines grown in media lacking MTX. Contrary to what would have been predicted based on the existing art, GFP gene expression was not reduced by more than 18% in any of the five cell lines over the 14 week evaluation period. Gene copy number determined by quantitative PCR was also stable with less than 24% deviation over time for all of the cell lines. These results indicate that a transgene amplified in the CHO DHFR locus is stable for an extended period of time, obviating the need to grow the cells in toxic selection agents that that could contaminate bioproduct formulations.

Example 2

Insertion of an Engineered Target Sequence into the CHO DHFR or GS Gene Coding Regions As diagrammed in FIG. 4, an alternative method for targeting a sequence of interest to an amplifiable locus involves the production of a cell line in which a portion of a selectable gene is replaced by an engineered target sequence. The advantage of this approach is that the subsequent insertion of a sequence of interest can be coupled with reconstitution of the selectable gene so that cell lines harboring the properly targeted sequence of interest can be selected using the appropriate media conditions. A cell line harboring such an engineered target sequence can be produced using nuclease-induced homologous recombination. In this case, a site-specific endonuclease which cuts a recognition sequence near or within the selectable gene sequence is preferred.

1. Engineered Meganucleases that Cut within the DHFR or GS Genes.

A meganuclease called "CHO-13/14" (SEQ ID NO: 12) was produced which cuts a recognition sequence in the CHO DHFR gene (SEQ ID NO: 13). The recognition sequence is in an intron between Exon 2 and Exon 3 of CHO DHFR. A meganuclease called "CGS-5/6" (SEQ ID NO: 14) was produced which cuts a recognition sequence in the CHO GS gene (SEQ ID NO: 15). Each meganuclease comprises an N-terminal nuclease-localization signal derived from SV40, a first meganuclease subunit, a linker sequence, and a second meganuclease subunit.

2. Site-Specific Cleavage of Plasmid DNA by Meganucleases CHO-13/14 and CGS-5/6

CHO-13/14 and CGS-5/6 were evaluated using a direct-repeat recombination assay as described in Example 1 (FIG. 7A). Both meganucleases were found to efficiently cleave their intended recognition sequences within the context of a plasmid-based reporter assay (FIG. 7B).

3. Site-Specific Cleavage of the CHO GS Gene by CGS-5/6

CHO cells were transfected with mRNA encoding CGS-5/6. mRNA was prepared by first producing a PCR template for an in vitro transcription reaction (SEQ ID NO: 22). Each PCR product included a T7 promoter and 609 bp of vector sequence downstream of the meganuclease gene. The PCR product was gel purified to ensure a single template. Capped (m7G) RNA was generated using the T7 RIBOMAX™ in vitro transcription kit (Promega Corp., Fitchburg, Wis.) according to the manufacturer's instructions and. Ribo m7G cap analog (Promega Corp., Fitchburg, Wis.) was included in the reaction and 0.5 μg of the purified meganuclease PCR product served as the DNA template. Capped RNA was purified using the SV Total RNA Isolation System (Promega Corp., Fitchburg, Wis.) according to the manufacturer's instructions.

$1.5 \times 10^6$ CHO-K1 cells were nucleofected with $3 \times 10^{12}$ copies of CGS-5/6 using an Amaxa NUCLEOFECTOR™ II device (Lonza Group Ltd., Basel, Switzerland) and the U-23 program according to the manufacturer's instructions. 48 hours post-transfection, genomic DNA was isolated from the cells using a FLEXIGENET™ DNA kit (Qiagen, Hilden, Germany) according to the manufacturer's instructions. The genomic DNA was then subjected to PCR to amplify the CGS-5/6 target site using the primers of SEQ ID NO: 23 and SEQ ID NO: 24. The PCR products were cloned into a pUC-19 plasmid and 94 plasmids harboring PCR products were digested with the BssSI restriction enzyme, which recognized and cuts the sequence 5'-CTCGTG-3' found within the CGS-5/6 recognition sequence. 17 plasmids were found to be resistant to BssSI, suggesting that the CGS-5/6 recognition site was mutated. These 17 plasmids were sequenced to confirm the existence of indels or point mutations within the CGS-5/6 recognition sequence (FIG. 7C).

These results indicate that CGS-5/6 is able to cut its intended target site within the CHO GS gene. Because the CGS-5/6 recognition sequence is within an exon in the GS coding sequence, many of the mutations introduced by CGS-5/6 are expected to frameshift the GS gene. Therefore, CGS-5/6 is useful for knocking-out CHO GS to produce GS (−/−) cell lines. Such cell lines are 7C). These results indicate that CGS-5/6 is able to cut its intended target site within the CHO GS gene. Because the CGS-5/6 recognition sequence is within an exon in the GS coding sequence, many of the mutations introduced by CGS-5/6 are expected to frameshift the GS gene. Therefore, CGS-5/6 is useful for knocking-out CHO GS to produce GS (−/−) cell lines. Such cell lines are useful because they are amenable to GS selection and amplification for producing biomanufacturing cell lines.

Example 3

Meganucleases for Targeting Gene Insertion to the CHO GS Locus

1. Engineered Meganucleases that Cut Downstream of the CHO GS Gene.

An engineered meganuclease called "CHOX-45/46" (SEQ ID NO: 29) was produced which recognizes a DNA sequence (SEQ ID NO: 30) approximately 7700 base pairs downstream of the CHO GS coding sequence. CHO cells were transfected with mRNA encoding CHOX-45/46 as described in Example 2. 72 hours post transfection, genomic DNA was extracted from the transfected cell pool and the region downstream of the CHO GS gene was PCR amplified using a pair of primers (SEQ ID NO: 31 and SEQ ID NO: 32) flanking the CHOX-45/46 recognition sequence. PCR products were then cloned and 24 cloned products were sequenced. It was found that 14 of the 24 clones PCR products (58.3%) had large mutations in the sequence consistent with meganuclease-induced genome cleavage followed by mutagenic repair by non-homologous end-joining From these data, we conclude that the CHOX-45/46 meganuclease is able to specifically cleave a DNA site downstream of the CHO GS gene coding sequence and will likely be able to target the insertion of transgenes to this amplifiable locus in the genome.

The invention claimed is:

1. A method for inserting an exogenous sequence into an amplifiable locus of a mammalian cell comprising:
   (a) providing a mammalian cell having an endogenous target site proximal to a selectable gene within the amplifiable locus, wherein the endogenous target site comprises:
      (i) a recognition sequence for an engineered meganuclease;
      (ii) a 5' flanking region 5' to the recognition sequence; and
      (iii) a 3' flanking region 3' to the recognition sequence;
   (b) introducing a double-stranded break between the 5' and 3' flanking regions of the endogenous target site; and
   (c) contacting the cell with a donor vector comprising from 5' to 3':
      (i) a donor 5' flanking region homologous to the 5' flanking region of the endogenous target site;
      (ii) an exogenous sequence; and
      (iii) a donor 3' flanking region homologous to the 3' flanking region of the endogenous target site;
   whereby the donor 5' flanking region, the exogenous sequence and the donor 3' flanking region are inserted between the 5' and 3' flanking regions of the endogenous target site by homologous recombination to provide a modified cell, wherein the engineered meganuclease comprises a polpeptide having at least 90%, 95%, 97%, 98%, or 99% sequence identity to SEQ ID NO: 9, and wherein the engineered meganuclease recognizes and cleaves a recognition site of SEQ ID NO: 7.

2. The method of claim 1, further comprising growing the modified cell in the presence of a compound that inhibits the function of the selectable gene to amplify the copy number of the selectable gene.

3. The method of claim 1, wherein the exogenous sequence comprises a gene of interest.

4. The method of claim 1, wherein the endogenous target site is downstream from the 3' regulatory region of the selectable gene.

5. The method of claim 4, wherein the endogenous target site is 0 to 100,000 base pairs downstream from the 3' regulatory region of the selectable gene.

6. The method of claim 1, wherein the endogenous target site is upstream from the 5' regulatory region of the selectable gene.

7. The method of claim 6, wherein the endogenous target site is 0 to 100,000 base pairs upstream from the 5' regulatory region of the selectable gene.

8. The method of claim 1, wherein the selectable gene is glutamine synthetase (GS) and the locus is methionine sulphoximine (MSX) amplifiable.

9. The method of claim 1, wherein the selectable gene is dihydrofolate reductase (DHFR) and the locus is Methotrexate (MTX) amplifiable.

10. The method of claim 1, wherein the selectable gene is selected from the group consisting of Dihydrofolate Reductase, Glutamine Synthetase, Hypoxanthine Phosphoribosyltransferase, Threonyl tRNA Synthetase, Na,K-ATPase, Asparagine Synthetase, Ornithine Decarboxylase, Inosine-5'-monophosphate dehydrogenase, Adenosine Deaminase, Thymidylate Synthetase, Aspartate Transcarbamylase, Metallothionein, Adenylate Deaminase (1,2), UMP-Synthetase and Ribonucleotide Reductase.

11. The method of claim 10, wherein the selectable gene is amplifiable by selection with a selection agent selected from the group consisting of Methotrexate (MTX), Methionine sulphoximine (MSX), Aminopterin, hypoxanthine, thymidine, Borrelidin, Ouabain, Albizziin, Beta-aspartyl hydroxamate, alpha-difluoromethylornithine (DFMO), Mycophenolic Acid, Adenosine, Alanosine, 2'deoxycoformycin, Fluorouracil, N-Phosphonacetyl-L-Aspartate (PALA), Cadmium, Adenine, Azaserine, Coformycin, 6-azauridine, pyrazofuran, hydroxyurea, motexafin gadolinium, fludarabine, cladribine, gemcitabine, tezacitabine and triapine.

* * * * *

UNITED STATES PATENT AND TRADEMARK OFFICE
CERTIFICATE OF CORRECTION

PATENT NO. : 9,822,381 B2
APPLICATION NO. : 14/806175
DATED : November 21, 2017
INVENTOR(S) : Derek Jantz et al.

It is certified that error appears in the above-identified patent and that said Letters Patent is hereby corrected as shown below:

In the Claims

At Column 167, Claim 1, please amend Line 45 as indicated below:
nuclease comprises a polypeptide having at least 90%, Signed and Sealed this
Nineteenth Day of June, 2018

Andrei Iancu
*Director of the United States Patent and Trademark Office*